(12) United States Patent
Lemmo et al.

(10) Patent No.: US 7,061,605 B2
(45) Date of Patent: Jun. 13, 2006

(54) APPARATUS AND METHOD FOR HIGH-THROUGHPUT PREPARATION AND SPECTROSCOPIC CLASSIFICATION AND CHARACTERIZATION OF COMPOSITIONS

(75) Inventors: Anthony V. Lemmo, Sudbury, MA (US); Javier P. Gonzalez-Zugasti, N. Billerica, MA (US); Michael J. Cima, Winchester, MA (US); Douglas A. Levinson, Sherborn, MA (US); Alasdair Y. Johnson, Newburyport, MA (US); Örn Almarsson, Shrewsbury, MA (US); Christopher McNulty, Minneapolis, MN (US)

(73) Assignee: Transform Pharmaceuticals, Inc., Lexington, MA (US)

( * ) Notice: Subject to any disclaimer, the term of this patent is extended or adjusted under 35 U.S.C. 154(b) by 47 days.

(21) Appl. No.: 11/051,517

(22) Filed: Jan. 31, 2005

(65) Prior Publication Data

US 2005/0130220 A1    Jun. 16, 2005

Related U.S. Application Data

(63) Continuation of application No. 10/235,922, filed on Sep. 6, 2002, now Pat. No. 6,977,723, said application No. 10/235,922 and a continuation-in-part of application No. 10/103,983, filed on Mar. 22, 2002, is a continuation-in-part of application No. 09/756,092, filed on Jan. 8, 2001, said application No. 10/103,983 and a continuation-in-part of application No. 09/994,585, filed on Nov. 27, 2001, is a continuation-in-part of application No. 09/756,092, filed on Jan. 8, 2001, said application No. 10/103,983 and a continuation-in-part of application No. PCT/US01/44818, filed on Nov. 28, 2001, , said application No. 09/994,585 and a continuation-in-part of application No. PCT/US01/00531, filed on Jan. 8, 2001, , said application No. 10/235,922 and a continuation-in-part of application No. 09/756,092, filed on Jan. 8, 2001, , said application No. 10/235,922 and a continuation-in-part of application No. 09/994,585, filed on Nov. 27, 2001, is a continuation-in-part of application No. 09/756,092, filed on Jan. 8, 2001, said application No. 09/994,585 and a continuation-in-part of application No. PCT/US01/00531, filed on Jan. 8, 2001, , said application No. 10/235,922 and a continuation-in-part of application No. 10/142,812, filed on May 10, 2002, is a continuation-in-part of application No. 10/103,983, filed on Mar. 22, 2002, which is a continuation-in-part of application No. 09/756,092, filed on Jan. 8, 2001, said application No. 10/103,983 and a continuation-in-part of application No. 09/994,585, filed on Nov. 27, 2001, is a continuation-in-part of application No. 09/756,092, filed on Jan. 8, 2001, said application No. 09/994,585 and a continuation-in-part of application No. PCT/US01/00531, filed on Jan. 8, 2001, , said application No. 10/103,983 and a continuation-in-part of application No. PCT/US01/44818, filed on Nov. 28, 2001.

(60) Provisional application No. 60/318,157, filed on Sep. 7, 2001, provisional application No. 60/318,152, filed on Sep. 7, 2001, provisional application No. 60/318,138, filed on Sep. 7, 2001, provisional application No. 60/290,320, filed on May 11, 2001, provisional application No. 60/235,629, filed on Nov. 28, 2000, provisional application No. 60/221,539, filed on Jul. 28, 2000, provisional application No. 60/196,821, filed on Apr. 13, 2000, provisional application No. 60/175,047, filed on Jan. 7, 2000.

(51) Int. Cl.
*G01J 3/42* (2006.01)
*G01J 3/44* (2006.01)
*G01N 21/17* (2006.01)

(52) U.S. Cl. .................. 356/300; 356/301; 356/326
(58) Field of Classification Search ................ 356/300, 356/301, 326, 328
See application file for complete search history.

(56) References Cited

U.S. PATENT DOCUMENTS

| | | |
|---|---|---|
| 3,422,268 A | 1/1969 | Meinig |
| 3,899,011 A | 8/1975 | Curtiss |
| 3,932,131 A | 1/1976 | Rolfo-Fontana |
| 4,399,687 A | 8/1983 | Collins |
| 4,693,377 A | 9/1987 | Gerrard et al. |
| 4,835,711 A | 5/1989 | Hutchins et al. |
| 4,877,745 A | 10/1989 | Hayes et al. |
| 5,206,699 A | 4/1993 | Stewart et al. |
| 5,324,483 A | 6/1994 | Cody et al. |
| 5,417,923 A | 5/1995 | Bojanic et al. |
| 5,424,037 A | 6/1995 | Zimmermann et al. |
| 5,445,934 A | 8/1995 | Fodor et al. |
| 5,463,564 A | 10/1995 | Agrafiotis et al. |
| 5,574,656 A | 11/1996 | Agrafiotis et al. |
| 5,658,802 A | 8/1997 | Hayes et al. |
| 5,684,711 A | 11/1997 | Agrafiotis et al. |
| 5,705,333 A | 1/1998 | Shah et al. |
| 5,744,305 A | 4/1998 | Fodor et al. |
| 5,763,278 A | 6/1998 | Sickinger et al. |
| 5,807,522 A | 9/1998 | Brown et al. |
| 5,832,182 A | 11/1998 | Zhang et al. |
| 5,843,767 A | 12/1998 | Beattie |
| 5,859,703 A | 1/1999 | Aldridge et al. |
| 5,901,069 A | 5/1999 | Agrafiotis et al. |
| 5,928,952 A | 7/1999 | Hutchins et al. |
| 5,956,137 A | 9/1999 | Lim et al. |
| 5,985,214 A | 11/1999 | Stylli et al. |
| 5,999,255 A | 12/1999 | Dupee et al. |
| 6,003,029 A | 12/1999 | Agrawal et al. |
| 6,100,901 A | 8/2000 | Mohda et al. |
| 6,140,643 A | 10/2000 | Brown et al. |
| 6,175,816 B1 | 1/2001 | Flavin et al. |
| 6,180,060 B1 | 1/2001 | Green et al. |
| 6,265,226 B1 | 7/2001 | Petro et al. |
| 6,267,935 B1 | 7/2001 | Hol et al. |
| 6,296,673 B1 | 10/2001 | Santarsiero et al. |
| 6,327,334 B1 | 12/2001 | Murray et al. |
| 6,331,440 B1 | 12/2001 | Nordstedt et al. |
| 6,333,501 B1 | 12/2001 | Labrenz |
| 6,421,553 B1 | 7/2002 | Costa et al. |
| 6,434,490 B1 | 8/2002 | Agrafiotis et al. |
| 6,460,014 B1 | 10/2002 | Waldman et al. |
| 6,487,523 B1 | 11/2002 | Jarman et al. |
| 6,642,060 B1 | 11/2003 | Morris et al. |
| 6,750,064 B1 | 6/2004 | Stahly et al. |
| 2001/0016631 A1 | 8/2001 | Freitag et al. |
| 2001/0036640 A1 | 11/2001 | D'Amico |
| 2001/0055775 A1 | 12/2001 | Schultz et al. |
| 2002/0023507 A1 | 2/2002 | Haiduk et al. |
| 2002/0029621 A1 | 3/2002 | Hajduk et al. |
| 2002/0032531 A1 | 3/2002 | Mansky et al. |
| 2002/0037647 A1 | 3/2002 | Hwang et al. |
| 2002/0048610 A1 | 4/2002 | Cima et al. |
| 2002/0049771 A1 | 4/2002 | Nagashima |
| 2002/0061599 A1 | 5/2002 | Elling et al. |
| 2002/0183938 A1 | 12/2002 | Kobylecki et al. |
| 2003/0022234 A1 | 1/2003 | Cawse et al. |
| 2003/0033088 A1 | 2/2003 | Agrafiotis et al. |
| 2003/0106492 A1 | 6/2003 | Levinson et al. |
| 2003/0119060 A1 | 6/2003 | Desrosiers et al. |
| 2003/0123057 A1 | 7/2003 | Lemmo et al. |
| 2003/0124028 A1 | 7/2003 | Carlson et al. |
| 2003/0124610 A1 | 7/2003 | Kvalheim et al. |
| 2003/0162226 A1 | 8/2003 | Cima et al. |
| 2003/0219906 A1 | 11/2003 | Giaquinta et al. |
| 2005/0089923 A9 | 4/2005 | Levinson et al. |
| 2005/0095696 A9 | 5/2005 | Lemmo et al. |
| 2005/0118636 A9 | 6/2005 | Levinson et al. |
| 2005/0118637 A9 | 6/2005 | Levinson et al. |

FOREIGN PATENT DOCUMENTS

| | | |
|---|---|---|
| EP | 0553 539 | 8/1993 |
| EP | 0 807 811 | 11/1997 |
| EP | 0 882 500 | 12/1998 |
| EP | 0 921 396 | 6/1999 |
| EP | 1174 183 | 1/2002 |
| EP | 1174 185 | 1/2002 |
| EP | 1186 892 | 3/2003 |
| WO | WO 94/11489 | 5/1994 |
| WO | WO 96/06842 | 3/1996 |
| WO | WO 96/16078 | 5/1996 |
| WO | WO 98/40159 | 9/1998 |
| WO | WO 98/47613 | 10/1998 |
| WO | WO 98/52614 | 11/1998 |
| WO | WO 99/04247 | 1/1999 |
| WO | WO 99/06814 | 2/1999 |
| WO | WO 99/08112 | 2/1999 |
| WO | WO 99/45379 | 9/1999 |
| WO | WO 99/45389 | 9/1999 |
| WO | WO 00/03240 | 1/2000 |
| WO | WO 00/29987 | 5/2000 |
| WO | WO 00/59627 | 10/2000 |
| WO | WO 01/034290 | 5/2001 |
| WO | WO 01/51919 | 7/2001 |
| WO | WO 02/31477 | 4/2002 |
| WO | WO 02/077772 | 10/2002 |
| WO | WO 02/093297 | 11/2002 |
| WO | WO 03/014732 | 2/2003 |
| WO | WO 03/023409 | 3/2003 |

OTHER PUBLICATIONS

Addadi (1985) "Growth and dissolution of organic crystals in the presence of organic crystals in the presence of additives stereochemistry and material science" *Angew Chem.* 97:476-496.

Aldridge, P.K. et al. (1995) "A robotic dissolution system with on-line fiber-optic UV analysis" *J. Pharm. Sci.* 84:8.

Almarsson, M.B. et al. (2003) "High-throughput surveys of crystal form diversity of highly polymorphic pharmaceutical compounds" *Crystal Growth and Design* 3(6):927-933.

Andersen, G. et al. (1996) "A spreadsheet approach to automated protein crystallization" *J. Appl. Cryst.* 29:236-240.

Anquetil, P.A. et al. (2003) "Laser Raman spectroscopic analysis of polymorphic forms in microliter fluid volumes" *J. Pharm. Sci.* 92(1):149-160.

Beckmann, W. et al. (1990) "The effect of additives on nucleation: A low cost automated apparatus" *J. Crystal Growth* 99: 1061-1064.

Beiswanger et al. (1989) "The prevalence and incidence of dental calculus in adults" *J. Clin. Dent.* 1:55-58.

Berkovitch-Yellin et al. (1985) "Morphology engineering of organic crystals with the assistance of 'tailor-made' growth inhibitors" *North Western Branch Papers* 2:49-50.

Botwell, D. (1999) "Options available—From start to finish—For obtaining expression data by microarray" *Nat. Genet.* 21(Suppl):25-32.

Brodersen, D. et al. (1999) "XAct: A program for construction, automated setup and bookkeeping of crystallization experiments" *J. Appl. Crystal.* 32:1012-1016.

Bugay, D.E. (2001) "Characterization of the solid-state: Spectroscopic techniques" *Adv. Drug. Delivery Rev.* 48:43-65.

Bullock, E. and Pyatt, E.C. (1972) "Apparatus for the growth of crystals from small volumes of solution" *J. Physics E-Scientific Instruments* 5:412-413.

Carrie, T.R. et al. (1983) "An automated sampling device for dissolution testing" *J. Pharm. Sci.* 72(8):Aug.

Casay, G. et al. (1992) "Laser scattering in a hanging drop vapor diffusion apparatus for protein crystal growth in a microgravity environment" *J. Crystal Growth* 122:95-101.

Chayen, N. et al. (1990) "An automated system for microbatch protein crystallization and screening" *J. Appl. Cryst.* 23:297-302.

Chayen, N. et al. (1994) "New developments of the IMPAX small-volume automated crystallization system" *Acta Cryst.* D50:456-458.

Chayen, N. et al. (1992) "Microbatch crystallization under oil—A new technique allowing many small-volume crystallization trials" *J. Crystal Growth* 122:176-180.

Cheung, V.G. et al. (1999) "Making and reading microarrays" *Nature Genetics Supplement* 21: Jan.

Cox, J. et al. (1987) "Experiments with automated protein crystallization" J. Appl. Cryst. 20:366-373.

Cox and Weber (1988) "An investigation of protein crystallization parameters using successive automated grid searches (SAGS)" *J. Crystal Growth* 90:318-324.

Craw et al. (1998) "Case Based Design for Tablet Formulation" IN: *Proc. 4th Eur. Workshop on Case Based Reasoning*, pp. 358-369.

Creese (1985) "Receptor Binding as a Primary Drug Screen" IN: *Neurotransmitter Receptor Binding, 2nd Ed.*, Chapter 9, pp. 189-233.

Cudney, B. et al. (1994) "Screening and optimization strategies for macromolecular crystal growth" *Acta Cryst.* D50:414-423.

Davis, G.F. et al. (2002) "Comparison of high throughput screening technologies for luminescence cell-based reporter screens" *J. Biomolec. Screening* 7(1).

De Castro, M.D. et al. (1998) "Automation of pharmaceutical dissolution testing by flow injection analysis" *J. Pharm. Biomed. Anal.* 8(4):329-336.

Eckstein et al. (1986) "Unattended, robotoc drug-release testing of enterically coated aspirin" Anal. Chem. 58:2316-2320.

Ferwerda R. et al. (1997) "The Use of FT-Raman Scpectoscopy and Chemometric Procedures in the Analysis of Pharmaceuticals" Nicolet Instrument Corporation, Madision,WI, May.

Findlay, P.F. et al. (1998) "Utilization of Fourier transform-Raman Spectroscopy for the study of pharmaceutical crystal forms" *J. Pharm Biomed. Anal.* 16:921-930.

Fleisch et al. (1968) "Influence of pyrophosphate on the transformation of amorphous to crystalline calcium phosphate" Calc. Tiss. Res. 2:49-59.

Fodor, S. P. A. (1997) "Massively parallel genomics" *Science* 277:393-394.

Fodor, S.P. et al. (1991) "Light-directed, spatially addressable parallel chemical synthesis" *Science* 251(4995):767-773.

Food and Drug Administration (1997) "International Conference on Harmonisation: Draft guidelines on impurities: Residual solvents: Availability" *Federal Register* 62:24302-24309.

Frank, R. (1995) "Simultaneous and combinatorial chemical synthesis techniques for the generation and screening of molecular diversity" *J. Biotechnol.* 41:259-272.

Gadamasetti, K.G., Ed. (1999) *Process CHemistry in the Pharmaceutical Industry*, Marcel Dekker, Inc., NY., NY, pp. 372-388.

Gardner, C.R. et al. (2003) "Application of high throughput technologies to drug substance and drug product development" *Computers and Chemical Engineering* 28:943-953.

George, et al. (1988) "Automated dissolution testing of sustained release tablets" *Am. Lab.* 20:106-112.

Gilliland, G. et al. (1994) "Screening for crystallization conditions and robotics" *Acta Cryst.* D50:408-413.

Gold, et al. (1964) "Effects of selective U.S. P. talcs on acetylsalicylic acid stability in tablets" *J. Pharm. Sci.* 53(1):52-54.

Gonzalez, F. et al. (1991) "Crocodile: An automated apparatus for organic crystal growth from solution" *Acta Astronautica* 25(12):775-784.

Gordon, et al. (1994) "Combinatorial organic synthesis, library screening strategies, and future directions" *J. Med. Chem.* 37(10:1384-1401.

Henry, C.E. (2004) "New wrinkles in drug discovery" *C&E News* 82(9).

Jancarik, J. et al. (1991) "Fast communications" *J. Appl. Cryst.* 24:409-411.

Kelders, H. et al. (1987) "Automated protein crystallization and a new crystal form of a substilisin: eglin complex" *Protein Engineering* 1(4):301-303.

Kuball, M. (2001) "Raman spectroscopy of GaN, AlGaN and AIN for process and growth monitoring/control" *Surface and Interface Anal.* 31:987-999.

Lamparter, E. et al. (1992) "The automation of dissolution testing of solid oral dosage forms" *J. Pharm. Biomed. Anal.* 10(10-12):727-733.

Lenczewski and LaFonna (1998) "Automated screening methods for determining optimum preservative systems for personal and home care products" *J. AOAC Intl.* 81:534-539.

Lennernas (1998) "Human intestinal permeability" *J. Pharm. Sci.* 87:403-410.

Leskovar, P. et al. (1985) *Urolithiasis Relat. Clin. Res.*, [Proc. Int. Symp.] 5th Meeting Date 1984, pp. 627-630.

Lindsey, J. et al. (1998) "Robotic work station for microscale synthetic chemistry: On-line absorption spectroscopy, quantitative automated thin-layer chromatography, and multiple reactions in parallel" *Rev. Sci. Instrum.* 59:940-950.

Littlechild, et al. (1991) "Protein crystallization: Magical or logical: Can we establish some general rules?" *J. Physics* 111-118.

Lo, S. et al. (1993) "Automated drug dissolution monitor that uses a UV-visible diode array spectrophotometer" *J. Pharm. Sci.* 82(4):Apr.

Longmire, M.L. et al. (Polymorph Analysis by Dispersive Raman Spectroscopy Nicolet Spectroscopy Research Center, Madision, WI, undated.

Mandel and Gaffar (1986) "Calculus revisited: A review" J. Clin. Periodontol. 13:249-257.

Mann, M. (1998) "Quantitative proteomics?" *Nature Biotechnol.* 17:Oct.

Martin, et al. (1986) "Automation of microtiter plate-chromogenic substrate LAL endotoxin assay method by use of a modified Cetus Pro/Pette Express system" *J. Parenteral Sci. Technol.* 4:61-66.

Marshall, A. et al. (1998) "DNA chips: An array of possibilities" *Nature Biotechnol.* 18:Jan.

Matousek P. et al. (2001) "Fluorescence suppression in resonance Raman spectroscopy using a high-performance picosecond Kerr gate" *J. Raman Spectroscopy* 32:983-988.

McFarland, et al. (1999) "Combinatorial approaches to materials discovery" *Trends Biotechnol.* 17(3):107-115.

McPherson, A. (1992) "Two approaches to the rapid screening of crystallization conditions" *J. Crystal Growth* 122:161-167.

Morris, K.R. et al. (2001) "Theoretical approaches to physical transformations of active pharmaceutical ingredients during manufacturing processes" *Adv. Drug Delivery Rev.* 48:91-114.

Morris, D. et al. (1989) "Automation of protein crystallization trials: Use of a robot to deliver reagents to a novel multi-chamber vapor diffusion place" *Biotechniques* 75(5):522-527.

Morris, K.R. et al. (1994) "An integrated approach to the selection of optimal salt form for a new drug candidate" *Intl. J. Pharmaceutics* 105:209-217.

Morris, K. R. et al. (2001) "Theoretical approaches to physical transformations of active pharmaceutical ingredients during manufacturing processes" *Adv. Drug Delivery Rev.* 48:91-114.

Morissette, S.L. et al. (2003) "Elucidation of crystal form diversity of the HIV protease inhibitor ritonavir by high-throughput crystallization" *Proc. Natl. Acad. Sci.* 100(5):2180-2184.

Morissette, S.L. et al. (2004) "High-throughput crystallization: polymorphs, salts, co-crystals and solvates of pharmaceutical solids" *Advanced Drug Delivery Reviews* 56:275-300.

Newman, A. (1990) "Send in the robots" *Anal. Chem.* 62(1):29-34.

Oldfield, T. et al. (1991) "A flexible approach to automated protein crystallization" *J. Appl. Cryst.* 24:255-260.

Otsuka, et al. (1999) "Physicochemical characterization of glybuzole polymorphs and their pharmaceutical properties" *Drug. Devel. Ind. Pharm.* 25(2):197-203.

Papas, A.N. et al. (1985) "Evaluation of robot automated drug dissolution measurement" *Am. Chem. Soc.* 67:1408-1411.

Peterson, M.L. et al. (2003) "Crystallization and transformation of acetaminophen trihydrate" *Crystal Growth and Design*, 3(5): 761-765.

Persidis, A. (1998) "Proteomics" *Nature Biotechnol.* 16:Apr.

Petty, C.J. et al. "Applications of FT-RAMAN Spectroscopy in the Pharmaceutical Industry" Nicolet Instrument Corporation, New Jersey, undated.

Petty, C. et al. (1995) "The use of FT-Raman Spectroscopy in the Study of Formulated Pharmaceuticals" Nicolet Instrument Corporation, New Jersey, May.

Popovitz-Biro et al. (1996) "Self-organization of molecules en route to crystal formation" IN: *From Simplicity Complexity Chem.—Beyond*, Pt. 1, pp. 85-98.

Ramsey, G. (1998) "DNA chips: State-of-the-art" *Nature Biotechnol.* 16:Jan.

Reixach et al. (2000) "Inhibition of β-amyloid-induced neurotoxicity by imadzopyridoindoles derived from a synthetic combinatorial library" *J. Struct. Biol.* 130:247-258.

Remenar, J.F. et al. (2003) "Selection and simultaneous polymorphism assessment via high-throughput crystallization: The case of sertraline" *Organic Process R&D* 7(6):990-996.

Remenar, J.F. (2003) "Crystal engineering of novel cocrystals of a triazole drug with 1,4-dicarboxylic acids" *J. Am. Chem. Soc.* 125:8456-8457.

Rivas, L. et al. (2001) "Conformational study of AZT in aqueous solution and adsorbed on a silver surface by means of Raman spectroscopy" *J. Raman Spectroscopy* 33:6-9.

Rosch, P. et al. (2002) "Chemotaxonomy of mints of genus Mentha by applying Raman spectroscopy" *Wiley InterScience*—www.interscience.wiley.com DOI:10.1002/bip.10099.

Rubin, B. et al. (1991) "Minimal intervention robotic protein crystallization" *J. Crystal Growth* 110:156-163.

Shah, K.P. et al. (1994) "Automated analytical systems for drug development studies. II-A System for dissolution testing" *J. Pharm. Biomed. Anal.* 12(12):1519-1527.

Shah, K.P. (1995) "Automated analytical systems for drug development studies 3. Multivessel dissolution testing system based on microdialysis sampling" *J. Pharm. Biomed. Anal.* 13:1235-1244.

Shaw, P. et al. (1999) "Practical experimental design techniques forautomatic and manual protein crystallization" *J. Crystal Growth* 196:665-673.

Sobriano, T.M. et al. (1993) "ASTEC: An automated system for sitting-drop protein crystallization" *J. Appl. Cryst.* 26:558-562.

Song, et al. (1997) "Controlled release of U-86983 from double-layer biodegradable matrices: Effect of additives on release mechanisms and kinetics" *J. Cont. Rel.* (45(2): 177-192.

Stephenson, G. A. et al. (2001) "Characterization of the solid state: Quantitative issues" *Adv. Drug Delivery Rev.* 48:67-90.

Stewart, P. et al. (1999) "Practical experimental design techniques for automatic and manual protein crystallization" *J. Crystal Growth* 196:665-673.

Suomi et al. (1974) "A clinical trial of a calculus-inhibitory dentifrice" *J. Periodontol.* 45(3):139-145.

Tabak et al. (1982) "Role of salivary mucins in the protection of the oral cavity" *J. Oral. Pathol.* 11:1-17.

Tisone, T. (1998) "Dispensing Systems for Miniaturized Diagnostics" *IVD Technology*.

Toto and Rapp (1972) "A clinical comparison of a new low abrasive dentifrice with intermediate and high abrasive dentifrices" *J. Periodontol.* 43(8):492-494.

Van De Poll, S.W.E. et al. (2002) "*In situ* investigation of the chemical composition of ceroid in human atherosclerosis by Raman spectroscopy" *J. Raman Spectroscopy* 33:544-551.

Vippagunta, S.R. et al. (2001) "Crystalline solids" *Adv. Drug Delivery Rev.* 48:3-26.

Ward et al. (1988) "Automatic preparation of protein crystals using laboratory robotics and automated visual inspection" *J. Crystal Growth* (90:325-339.

Wehrens, R. et al. (2002) "Mixture modeling of medical magnetic resonance data" *J. Chemometrics* 16:274-282.

Weissbuch et al. (1999) "Towards an understanding and control of nucleation, growth, habit, dissolution, and structure of crystals using 'tailor-made' auxiliaries" IN: *Molecular Modeling Applications in Crystallization*, edited by Allan S. Myerson, Cambridge University Press, pp. 166-227.

Weissbuch et al. (1993) "Application of cryo-electron microscopy to self-assembled mixed monolayers for studying crystallinity and twinning" *J. Phys. Chem.* 97:8692-8695.

Weissbuch et al. (1993) "Mixed monolayers for the design of structured surfaces to induce oriented 3-D crystallization" *J. Phys. Chem.* 97:12848-12857.

Weissbuch et al. (1990) "Structural changes in amphiphillic aggregates at the air-solution interfaces as studied by oriented crystallization and nonlinear optics" *J. Am. Chem. Soc.* 112:5874-5875.

Weissbuch et al. (1986) "'Tailormade' auxiliaries for nucleation, growth and dissolution of organic crystals" *Pure and Appl. Chem.* 58:947-954.

Weissbuch et al. "Oriented crystallization and non-linear optics: Tools for studying structural changes of amphiphillic aggregates at the air-solution interface" IN: *Oriented Crystallization and Non-linear Optics*, pp. 82-88.

Yakovlev, Y. et al. (1998) "A laboratory apparatus for crystal growth from solution" *Instruments and Exp. Techniques* 41(2):292-296.

Yu, L. (2001) "Amorphous pharmaceutical solids: Preparation, characterization and stabilization" *Adv. Drug.Delivery Rev.* 48:27-42.

Zander et al. (1960) "Mineralization of dental calculus" IN: *Proc. Soc. Exp. Biol. Med.* 103(2):257-261.

Zeelen, J. et al. (1994) "Crystallization experiments with 2-enoyl-CoA hydratase, using an automated 'fast screening' crystallization protocol" *Acta Cryst.* D50:443-447.

Zhu, H. (1996) "Influence of water activity in organic solvent + water mixtures on the nature of the crystallizing drug phase. 1. Theophylline" *Int. J. Pharm.* 135:151-160.

Pending U.S. Appl. No. 11/051,698, filed Jan. 31, 2005, Cima et al.

*Primary Examiner*—F. L. Evans
(74) *Attorney, Agent, or Firm*—Saliwanchik, Lloyd & Saliwanchik

(57) ABSTRACT

Systems and methods are described that allow the high-throughput preparation, processing, and study of arrays of samples, each of which comprises at least one compound. Particular embodiments of the invention allow a large number of experiments to be performed in parallel on samples that comprised of one or more compounds on the milligram or microgram quantities of compounds. Other embodiments of the invention encompass methods and devices for the rapid screening of the results of such experiments, as well as methods and devices for rapidly determining whether or not similarities exist among groups of samples in an array. Particular embodiments of the invention encompass methods and devices for the high-throughput preparation of different forms of compounds (e.g., different crystalline forms), for the discovery of new forms of old compounds, and for the discovery of new methods of producing such forms. Embodiments of the invention also allow for the high-throughput determination of how specific compounds or forms of compounds behave when exposed to other chemicals or environmental conditions.

23 Claims, 44 Drawing Sheets ic the compound, and other uses. Indeed, large numbers of
APPARATUS AND METHOD FOR HIGH-THROUGHPUT PREPARATION AND SPECTROSCOPIC CLASSIFICATION AND CHARACTERIZATION OF COMPOSITIONS This application is a continuation of U.S. patent application Ser. No. 10/235,922, filed Sep. 6, 2002 now U.S. Pat. No. 6,977,723, which claims benefit of U.S. Provisional Patent Applications 60/318,152, 60/318,157, and 60/318,138, each of which was filed on Sep. 7, 2001; each of which is incorporated herein in its entirety.

This application is also a continuation of U.S. patent application Ser. No. 10/235,922, filed Sep. 6, 2002, which is a continuation-in-part of U.S. patent application Ser. No. 10/103,983, filed Mar. 22, 2002 which is a continuation-in-part of U.S. patent application Ser. No. 09/756,092, filed Jan. 8, 2001 (which claims the benefit of U.S. Provisional Patent Application 60/221,539, filed Jul. 28, 2000, U.S. Provisional Patent Application 60/196,821, filed Apr. 13, 2000, and U.S. Provisional Patent Application 60/175,047, filed Jan. 7, 2000), said Ser. No. 10/103,983 is also a continuation-in-part of Ser. No. 09/994,585, filed Nov. 27, 2001, which is a continuation-in-part of U.S. patent application Ser. No. 09/756,092, filed Jan. 8, 2001 (which claims the benefit of U.S. Provisional Patent Application 60/175,047, filed Jan. 7, 2000; U.S. Provisional Patent Application 60/196,821, filed Apr. 13, 2000; and U.S. Provisional Patent Application 60/221,539, filed Jul. 28, 2000), said Ser. No. 09/994,585, filed Nov. 27, 2001, also being a continuation-in-part of International Application PCT/US01/00531, filed Jan. 8, 2001 (which claims the benefit of U.S. Provisional Patent Application 60/175,047, filed Jan. 7, 2000; U.S. Provisional Patent Application 60/196,821, filed Apr. 13, 2000; and U.S. Provisional Patent Application 60/221,539, filed Jul. 28, 2000), said Ser. No. 10/103,983 is also a continuation-in-part of International Application PCT/US01/44818, filed Nov. 28, 2001, which claims the benefit of U.S. Provisional Patent Application 60/253,629, filed Nov. 28, 2000.

This application is also a continuation of U.S. patent application Ser. No. 10/235,922, filed Sep. 6, 2002, which is a continuation-in-part of U.S. patent application Ser. No. 09/756,092, filed Jan. 8, 2001, which claims the benefit of U.S. Provisional Patent Application 60/221,539, filed Jul. 28, 2000, U.S. Provisional Patent Application 60/196,821, filed Apr. 13, 2000, and U.S. Provisional Patent Application 60/175,047, filed Jan. 7, 2000.

This application is also a continuation of U.S. patent application Ser. No. 10/235,922, filed Sep. 6, 2002, which is a continuation-in-part of U.S. patent application Ser. No. 09/994,585, filed Nov. 27, 2001, which is a continuation-in-part of U.S. patent application Ser. No. 09/756,092, filed Jan. 8, 2001 (which claims the benefit of U.S. Provisional Patent Application 60/175,047, filed Jan. 7, 2000; U.S. Provisional Patent Application 60/196,821, filed Apr. 13, 2000; and U.S. Provisional Patent Application 60/221,539, filed Jul. 28, 2000), said Ser. No. 09/994,585, filed Nov. 27, 2001, also being a continuation-in-part of International Application PCT/US01/00531, filed Jan. 8, 2001 (which claims the benefit of U.S. Provisional Patent Application 60/175,047, filed Jan. 7, 2000; U.S. Provisional Patent Application 60/196,821, filed Apr. 13, 2000; and U.S. Provisional Patent Application 60/221,539, filed Jul. 28, 2000).

This application is also a continuation of U.S. patent application Ser. No. 10/235,922, filed Sep. 6, 2002, which is a continuation-in-part of U.S. patent application Ser. No. 10/142,812, filed May 10, 2002 (which claims the benefit of U.S. Provisional Patent Application 60/290,320, filed May 11, 2001), which is a continuation-in-part of U.S. patent application Ser. No. 10/103,983, filed Mar. 22, 2002, which is a continuation-in-part of U.S. patent application Ser. No. 09/756,092, filed Jan. 8, 2001 (which claims the benefit of U.S. Provisional Patent Application 60/221,539, filed Jul. 28, 2000, U.S. Provisional Patent Application 60/196,821, filed Apr. 13, 2000, and U.S. Provisional Patent Application 60/175,047, filed Jan. 7, 2000), said Ser. No. 10/103,983 is also a continuation-in-part of Ser. No. 09/994,585, filed Nov. 27, 2001, which is a continuation-in-part of U.S. patent application Ser. No. 09/756,092, filed Jan. 8, 2001 (which claims the benefit of U.S. Provisional Patent Application 60/175,047, filed Jan. 7, 2000; U.S. Provisional Patent Application 60/196,821, filed Apr. 13, 2000; and U.S. Provisional Patent Application 60/221,539, filed Jul. 28, 2000), said Ser. No. 09/994,585, filed Nov. 27, 2001, also being a continuation-in-part of International Application PCT/US01/00531, filed Jan. 8, 2001 (which claims the benefit of U.S. Provisional Patent Application 60/175,047, filed Jan. 7, 2000; U.S. Provisional Patent Application 60/196,821, filed Apr. 13, 2000; and U.S. Provisional Patent Application 60/221,539, filed Jul. 28, 2000), said Ser. No. 10/103,983 is also a continuation-in-part of International Application PCT/US01/44818, filed Nov. 28, 2001, which claims the benefit of U.S. Provisional Patent Application 60/253,629, filed Nov. 28, 2000.

1. FIELD OF THE INVENTION

This invention generally relates to devices, systems, and methods for conducting and evaluating multiple small-scale experiments. Particular embodiments of the invention encompass methods and devices for the high-throughput preparation and study of a variety of compounds, compositions, and forms of compounds and compositions.

2. BACKGROUND OF THE INVENTION

In recent years, chemical discovery has seen an explosion of new science, such as genomics, proteomic and bioinformatics, as well as high-throughput technologies for identifying and/or creating new compounds or chemical entities, such as combinational chemistry. Such technologies allow the researcher to rapidly synthesize and/or identify large numbers of compounds. At the same time, these technologies have led to the development of more compounds that are larger, greasier and more hydrophobic, and thus more challenging to develop into products.

Conducting large numbers of experiments results in the need to inspect or otherwise analyze hundreds or thousands of samples, e.g., for the presence of the desired result. And, a large number of the pre-selected samples require continuing analysis. The resulting voluminous data must then be processed effectively and efficiently, e.g., within a reasonable amount of time.

The physical form of a compound, particularly that of an active pharmaceutical ingredient (API), plays a role in a number of areas. For example, in order to be developed into a drug, a compound must be able to be delivered to the patient via some suitable device or formulation, and it must also pass criteria in several categories, such as safety, metabolic profile, pharmacokinetics, cost and reliability of synthetic process, stability, and bioavailability.

High-throughput technologies, when possible, enable the discovery of various physical forms of a compound, some of which may be particularly useful as pharmaceuticals, for formulating pharmaceuticals, intermediates for manufacturing drugs, foods, food additives and the like. (See, e.g., International Application Nos. WO00/59627, WO01/09391, and WO01/51919). Such technologies can result in extraordinary numbers of experiments being conducted very rapidly thereby creating large amounts of data and results that must be reviewed and analyzed by the scientist in order to identify a desired form of the compound. For example, in order to discover various solid forms of a compound, often thousands of experiments, using many different conditions, solvents, additives, pH, thermal cycles, and the like must be conducted. Dozens or even hundreds of the forms must be analyzed before a desired form of the compound can be identified and chosen for further development as a potential product.

Some devices for facilitating large numbers of experiments simultaneously are known. In addition, there are systems consisting of blocks with multiple wells for performing reactions for different applications such as combinatorial chemistry. Examples of such system include the TITAN™ Reactor Clamp and TITAN™ PTFE MicroPlates (both available from Radleys, Shire Hill, Saffron Walden, Essex CBII 3AZ, United Kingdom). A multiple-well tray for crystallization reactions is described in U.S. Pat. No. 6,039,804. There also exist systems of block, tubes, and seals, such as the Radleys TITAN™ Glass Micro Reactor Tube System and the WebSeal System (available from Radleys, Shire Hill, Saffron Walden, Essex CBII 3AZ, United Kingdom). Many tubes or vials of different geometries also exist, including many with crimp, threaded, or snap-on caps.

Spectroscopic techniques such as infrared (IR) and Raman spectroscopy are useful for detecting changes in structure and/or order. In addition, techniques such as Nuclear Magnetic Resonance (NMR), Differential Scanning Calorimetry, ultra-violet (UV) spectroscopy, circular dichroism (CD), linear dichroism (LD), and X-ray diffraction are powerful techniques. However, each of these techniques must be coupled with data analysis and handling techniques to enable data collection and processing of hundred or thousands of samples. All these techniques are not easily adaptable for high-throughput analysis of structural information and order. Indeed, high-throughput analysis still remains a challenge due to the high degree of automation desired in both physical sample handling and in analysis of the collected data. These and many other difficulties are overcome by the system and methods disclosed herein. The invention disclosed herein further extends the reach of high-throughput analysis with a high degree of sensitivity and specificity. Moreover, the disclosed techniques also efficiently use limited test material quantities to enable effective screening at a low cost.

3. SUMMARY OF THE INVENTION

This invention is directed, in part, to methods and systems for determining conditions that when applied to a particular compound or composition provide a particular result (e.g., a compound or composition having particular chemical and/or physical properties). The invention is further directed to methods and systems for the generation, synthesis, and/or identification of various forms of a compound or composition, such as, but not limited to, polymorphs, salts, hydrates, solvates, desolvates, and amorphous forms. The invention is also directed to methods and systems for the generation, synthesis, and/or identification of various forms of solids such as, but not limited to, crystal habit and particle size distribution.

The invention encompasses a complete system for planning and conducting high-throughput experiments, e.g., experiments on one or more arrays of samples. The system encompasses apparatuses and methods that can be used to prepare and process samples, apparatuses and methods that can be used to inspect, process, and screen samples, apparatuses and methods that can be used to collect spectroscopic and other data from one or more of the samples, and apparatuses and methods that can be used to process, interpret, and analyze the data. The system includes robotics, computers, spectral techniques, and various mechanical devices, each designed to conduct high-throughput experiments on large or preferably small amounts of material, including materials on the milligram and microgram scales.

In particular, this invention encompasses methods and devices for the high-throughput preparation, processing, screening, and/or analyzing of samples. Particular methods of the invention utilize arrays of samples, each of which comprises the compound or composition of interest (referred to herein as the "compound-of-interest") in optional contact with one or more solvents or excipients. In specific embodiments of the invention, each sample is held in a container that can be manipulated separately from other samples in the array.

One embodiment of the invention encompasses a high throughput system for evaluating experiments, which comprises: a) a plurality of containers, each of which contains a compound-of-interest and optionally one or more additional compounds; b) a block containing an array of holes for receiving said containers; and c) an imaging device capable of producing images of the samples while in the containers.

Another embodiment of the invention encompasses a method of evaluating experiments which comprises: a) providing a system for evaluating experiments comprising: i) a plurality of containers, each of which contains a compound-of-interest and optionally one or more additional compounds; ii) a block containing an array of holes for receiving the containers; and iii) an imaging device; b) positioning the block near the imaging device; c) producing images of the contents of each of the containers; d) analyzing the images for the presence of a desired experimental result; and e) identifying containers with the desired experimental result.

Another embodiment of the invention encompasses an automated high throughput method for screening for solid forms of a compound-of-interest, wherein the compound-of-interest is a biologically active small organic molecule, which comprises: a) preparing an array of samples, each of which comprises the compound-of-interest and optionally one or more additional compounds; b) processing the array so as to generate solid forms; c) prescreening the array for solid formation using a digital imaging camera; d) identifying samples with solid formations for further analysis; e) rearranging and reprocessing samples with solids, and optionally repeating steps (b) to (d).

Another embodiment of the invention encompasses a high-throughput system for processing samples and screening for solid forms of a compound-of-interest, which comprises: a) removable containers, each of which contains a compound-of-interest and optionally one or more additional compounds; b) a block made of a thermally conductive material having an array of holes, each hole having a top and a bottom, the top having an opening for receiving the removable container and the bottom having an access hole; c) a thermal processing system for heating and cooling multiple blocks simultaneously; and d) an imaging device (e.g., a camera, preferably a digital video camera) for detecting solid forms.

Another embodiment of the invention encompasses a method for the high-throughput processing and screening of samples, which comprises: a) providing a system for processing a sample comprising: i) removable containers; ii) a block having an array of holes, each hole having a top and a bottom, the top having an opening for receiving a container and the bottom having an access hole; b) placing the containers in the holes; c) dispensing a controlled amount of a compound-of-interest and optionally one or more additional compounds in each container to provide an array of samples; d) processing the array; and e) screening the samples for the presence or absence of solid forms using an imaging device.

Another embodiment of the invention encompasses a method of screening an array of samples which comprises obtaining a Raman spectrum of each sample and determining which, if any, of the spectra share a spectral feature.

Another embodiment of the invention encompasses a method of screening an array of samples for the presence of a particular form of a compound-of-interest, which comprises obtaining a Raman spectrum of each sample.

Another embodiment of the invention encompasses a method of screening an array of samples for the absence of a particular form of a compound-of-interest, which comprises obtaining a Raman spectrum of each sample.

Another embodiment of the invention encompasses a system for detecting similarities among a plurality of samples, which comprises: a) a device for obtaining a spectrum for each sample; and b) a computer configured to analyze each of the spectra and to generate a plurality of bins, wherein each bin corresponds to samples sharing at least one spectral feature.

Another embodiment of the invention encompasses a method of detecting similarities among a plurality of samples, which comprises: a) collecting a spectrum for each of the plurality of samples; b) calculating a similarity metric between the spectrum of one sample and that of at least one other of the plurality; c) clustering, based on the similarity metric, the spectra into bins, each bin containing similar spectra; and d) presenting the clustered spectra with similar spectra located close to each other.

Another embodiment of the invention encompasses a method of analyzing a plurality of samples, which comprises: a) analyzing the samples with a spectrometer to produce spectral data; b) under processor control, identifying similarities between the spectra; and c) grouping the spectra into bins of similarity.

Another embodiment of the invention encompasses a database containing a plurality of spectral samples organized into a plurality of bins, the bins corresponding to a hierarchical organization of the plurality of spectral samples based on pair-wise similarity scores calculated in accordance with a similarity metric.

3.1. BRIEF DESCRIPTION OF THE DRAWINGS

Features and advantages of the invention can be understood with reference to the attached figures. The drawings are not necessarily to scale, emphasis instead being placed upon illustrating the principles of the invention.

In FIG. 10, the laser light is at an angle that is not normal to the camera lens.

3.2. DEFINITIONS

Figure 1:
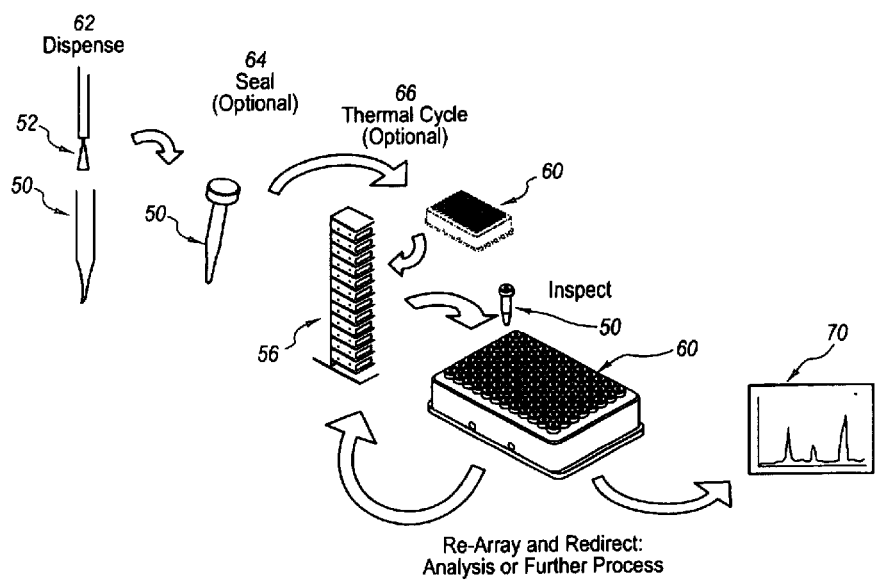
FIG. 1 is a schematic diagram of steps associated with a specific embodiment of the invention, wherein tubes are filled with a compound-of-interest and optional other compounds, processed, and inspected.

As used herein and unless otherwise indicated, the term "array," when used to refer to a plurality of objects (e.g., samples), means a plurality of objects that are organized physically or indexed in some manner (e.g., with a physical map or within the memory of a computer) that allows the ready tracking and identification of specific members of the plurality. Typical arrays of samples comprise at least 6, 12, 24, 94, 96, 380, 384, 1530, or 1536 samples.

As used herein and unless otherwise indicated, the term "compound-of-interest" refers to the substance, compound, molecule, or chemical studied, formulated, or otherwise manipulated using methods or devices of the invention. Examples of compounds-of-interest include, but are not limited to, pharmaceuticals, veterinary compounds, dietary supplements, alternative medicines, nutraceuticals, sensory compounds, agrochemicals, the active components of consumer products, and the active components of industrial formulations. A preferred compound-of-interest is the active component of a pharmaceutical, also referred to as the active pharmaceutical ingredient (API). Specific APIs are suitable for administration to humans. Specific APIs are small organic molecules that are not polypeptides, proteins, oligonucleotides, nucleic acids, or other macromolecules. Small organic molecules include, but are not limited to, molecules with molecular weights of less than about 1000, 750, or 500 grams/mol.

As used herein and unless otherwise indicated, the term "controlled amount" refers to an amount of a compound that is weighed, aliquotted, or otherwise dispensed in a manner that attempts to control the amount of the compound. Preferably, a controlled amount of a compound differs from a predetermined amount by less than about 10, 5, or 1 percent of the predetermined amount. For example, if one were to dispense, handle, or otherwise use 100 µg of a compound-of-interest, a controlled amount of that compound-of-interest would preferably weight from about 90 µg to about 110 µg, from about 95 µg to about 105 µg, or from about 99 µg to about 101 µg.

As used herein and unless otherwise indicated, the term "form" refers to the physical form of a compound or composition. Examples of forms include solid and liquid. Examples of forms of solids, or "solid forms," include, but are not limited to, salts, solvates (e.g., hydrates), desolvates, clathrates, amorphous and crystalline forms, polymorphs, crystal habits (e.g., needles, plates, particles, and rhomboids), crystal color, crystal size, crystal size distribution, co-crystals, and complexes.

As used herein and unless otherwise indicated, the term "pharmaceutical" refers to a substance, compound, or composition that has a therapeutic, disease or condition preventive, disease or condition management, diagnostic, or prophylactic effect when administered to an animal or human, and includes prescription and over-the-counter pharmaceuticals. Examples of pharmaceuticals include, but are not limited to, macromolecules, oligonucleotides, oligonucleotide conjugates, polynucleotides, polynucleotide conjugates, proteins, peptides, peptidomimetics, polysaccharides, hormones, steroids, nucleotides, nucleosides, amino acids, small molecules, vaccines, contrasting agents, and the like.

As used herein and unless otherwise indicated, the term "sample" refers to an isolated amount of a compound or composition. A typical sample comprises a controlled amount of a compound-of-interest, and may also contain one or more excipients, solvents, additives (e.g., stabilizers and antioxidants), or other compounds or materials (e.g., materials that facilitate crystal growth). Specific samples comprise a compound-of-interest in an amount less than about 100 mg, 25 mg, 1 mg, 500 µg, 250 µg, 100 µg, 50 µg, 25 µg, 10 µg, 5 µg, 2.5 µg, 1 µg, or 0.5 µg.

4. DETAILED DESCRIPTION OF THE INVENTION

This invention is based, in part, on the discovery of various methods and devices that can facilitate the rapid and efficient preparation and analysis of compounds, compositions, and various forms of compounds and compositions. For the sake of convenience, methods and devices of the invention may be described with reference to four general aspects of it, which are referred to herein as "Sample Containment and Preparation," "Sample Handling and Processing," "Sample Imaging," and "Spectroscopic Data Collection and Analysis." Each of these aspects encompasses novel embodiments of the invention which can be used alone or together.

For example, a specific method comprises the preparation of an array of samples, each of which is held in a sealed container; exposing the samples to a condition, such as heat or cold, for a particular amount of time; imaging the samples to determine, for example, whether they produced or contain a solid or liquid; and collecting and analyzing spectroscopic data obtained from one or more of the samples. FIG. 1 provides a general illustration of this method and a system that can be used to implement it. Briefly, one or more tubes 50 are placed in an array of wells in a thermally conductive block 60. Next, chemical ingredients 52 for each experiment are dispensed into tubes 50. Optionally, a cap 54, possibly including a seal 64, is placed on tube 50 to prevent leakage, evaporation, or contamination of the contents. The tubes are then optionally processed using a controlled thermal cycling system 56. Following inspection of the contents of tubes 50 (e.g., using automated imaging equipment), experimental specimens or samples of interest are identified. The samples of interest are then optionally separated from other samples for further analysis or processing.

The other embodiments of the invention can be understood from the more detailed discussions of its Sample Containment and Preparation, Sample Handling and Processing, Sample Imaging, and Spectroscopic Data Collection and Analysis aspects provided below.

4.1. Sample Containment and Preparation 4.1.1. Tubes and Blocks

High throughput preparation and analysis of samples is aided by the assembly of arrays of samples, each of which can be the same or different from other samples in the array. In specific embodiments of this invention, arrays of samples are prepared in removable containers (e.g., vials or tubes), which fit in holes, wells, or depressions in a holder, or what is referred to herein as a "block." This system is referred to herein as "tubes and blocks" or "tubes in blocks."

A wide variety of containers known to those skilled in the art can be used to hold the individual samples in an array. Because preferred embodiments of the invention are directed to the high-throughput preparation, processing, and/or testing of samples that contain relatively small amounts of the compound-of-interest, preferred containers are sufficiently small so that many of them can be fit into a block. Preferred containers are also optically transparent or translucent to allow visual inspection of their contents, are chemically inert (e.g., will not chemically react with the compounds they contain), and can withstand physical conditions (e.g., thermal processing) to which it will be exposed. Specific containers are made of glass or polypropylene. Preferred containers can be sealed or closed. For example, a septum that can be pierced by a needle or other device that can add fluids to the container or remove fluids from the container is used in a preferred embodiment. Containers may also be closed with a closure (e.g., a cap or top) that allows light to pass through into the container to illuminate its contents. Moreover, the closure may be used to imprint or otherwise provide an identifier to a single tube or a sub-block. Such an identifier may be in addition to or in lieu of an identifier associated with each block.

Figures 2A, 2B:
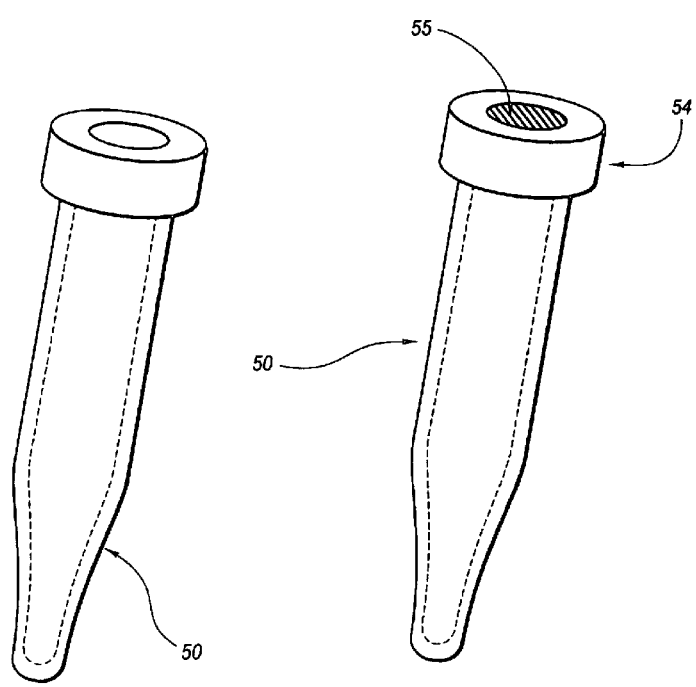
FIGS. 2A and 2B are views of a tube in its open and capped configurations, respectively.

FIG. 2 provides a view of a tube container in its open and capped configurations. The specific closure 54 shown in the figure can be crimped, is made of aluminum or some other suitable material, and incorporates a polymer septum 55.

Figure 3A:
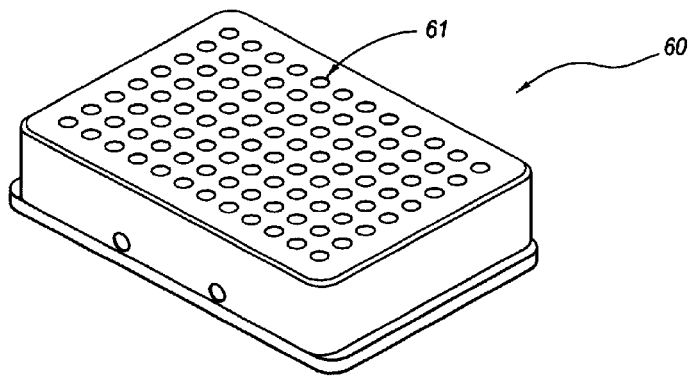
FIGS. 3A and 3B are top and bottom perspective views of a block, respectively.
Figure 3B:
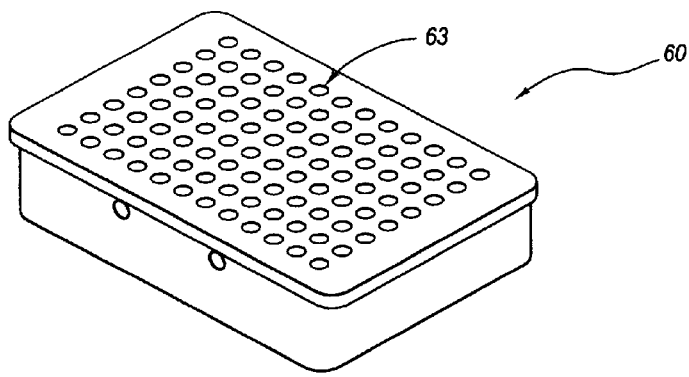
Figure 3C:
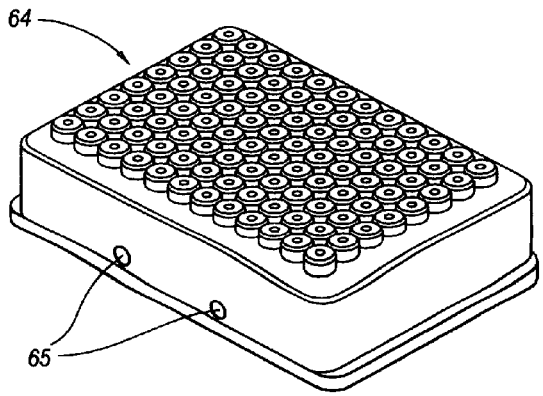
FIG. 3C is a top perspective view of the block filled with capped tubes.

The blocks that hold the containers preferably allow for the automated removal and insertion of the containers. For example, a particular block has holes with top openings large enough to accommodate containers and smaller bottom openings that allow the containers to be pushed out of their holes with a rod or pin. Such blocks can be used with particular systems of the invention that comprise a lifter mechanism capable of protruding through the access hole in the blocks to elevate one or more containers until at least partially removed from the block. Preferably, the block is thermally conductive and is made from metal (e.g., copper, steel, or aluminum), although other materials, such as plastic, may also be used. As shown in FIGS. 3A–3C, a specific block 60 is made of aluminum, and has 96 holes 61 into which containers will fit. Block 60 provides thermal transfer between the tubes and a controlled means for temperature regulation. Block 60 incorporates a set of bottom access holes 63 that provide for physical and optical access to each individual vial. Optionally, block 60 has one or more indents 65 on two opposing sides of block 60 to provide means for preventing slipping or dropping of the block 60 when automated handling, such as by a robotic arm, is used to move block 60.

The geometry, size, and materials from which a block is made can be readily adapted for use with particular containers, processing conditions, and sample and block handling devices. For example, the holes in a block may be counter-bored, counter-sunk, stepped, tapered, or more complex-shaped to fit different tube and seal shapes, although in FIG. 3 they are simply shown as illustrative straight through holes.

The tube and block system has several distinct advantages over alternative ways of performing parallel experiments. First, the use of individual containers, instead of using a plate, format allows for the individual handling of each sample, or experiment, in an array. This makes it possible to re-array containers to separate those that show desired properties from the rest, in order to perform further processing or analysis of only some of the experiments. In addition, for experiment samples or products that can exhibit different properties depending on orientation (e.g., samples that contain crystals), the containers can be precisely oriented with respect to an analysis instrument, such as a Raman spectrometer or X-ray diffractometer.

The invention also encompasses the use of various tube materials, including the use of different types of glass such as amber glass vials, which can protect their contents from degradation due to exposure to light during processing. Optical inspection of the contents of each vial is possible by illuminating the samples with light source having a wavelength able to penetrate the vial walls, and using a detector (camera) for imaging light at that wavelength.

Second, a translucent, transparent, semitransparent, or clear container allows for optical inspection of the experiment from multiple angles, generally perpendicular to the axis of the container, but also from underneath through optional access holes in the block. Also, the use of such containers, including but not limited to, glass or clear polypropylene tubes, allows for optical inspection methods such as machine vision or microscopy. In addition, clear plastic tubes, or tubes fabricated from quartz or any other optically transparent, translucent, or clear material can be used. Chromacol Ltd. (2 Little Mundells, Wellwyn Garden City, Herts AL7 1EW, UNITED KINGDOM) offers many examples of the variety of available vial shapes and materials. The ability to visually inspect each experiment in an array, from all angles, allows analysis of the contents, such as solids or precipitates, in a number of ways, including without limitation, estimating size, color, shape, orientation and location in the container.

Third, because containers can be of any shape, the tubes and blocks system enables the testing of a wide range of experimental volumes. By selecting the shape of the containers, small volume experiments (e.g., about 2 μl) are still clearly visible in the narrow, preferably conical, tip of the preferred container, while larger volume experiments (greater than 100 μl) may also be tested due to the larger diameter top section of the tubes. Also, the container geometry in the preferred embodiment permits the use of a tightly sealing cap. An airtight seal isolates the contents of the experiments from the environment and prevents evaporation, leakage or contamination of, or changes to, the components in the containers.

Fourth, many containers can be capped. The use of a cap with an integral translucent frit or septum allows for the ability to probe, add, or remove components to/from the experiment, as well as the ability to illuminate the container's contents through the septum. This lighting of the samples in the containers though the septa can be accomplished through the use of light sources such as fiber optic light guides or light-emitting diodes (LEDs).

Fifth, the use of thermally conductive blocks allows for quick heat transfer between a heating or cooling source and the containers, as well as a large thermal mass to maintain the containers at the desired temperature when temporarily not in contact with a heat/cooling source. As noted previously, many metals, plastics, and a variety of other materials can used to build the blocks. Although aluminum does not exhibit the best thermal conductivity or heat capacity, it is preferred in view of additional considerations such as weight, cost, corrosion-resistance, and ease of manufacturing.

Sixth, the chosen geometry of the block offers certain advantages. For example, the access holes at the bottom of each container hole allows for physical access to the containers, so that they can be partially or fully removed from the block for inspection or rearranging purposes. In addition, the holes also provide a window for optical inspection of the containers from the underside of the block that can be used alone or in conjunction with top lighting of the containers, e.g., through translucent septa, to image the experiments in the containers in a block.

4.1.2. Sample Preparation

The composition of a particular sample in an array will depend on the use to which the particular method or device of the invention is put. For example, if an array is used to provide crystalline forms of a compound-of-interest, each sample might contain one or more solvents or solvent mixtures in addition to the compound-of-interest (which could be evaporated) or to which other solvents (e.g., antisolvents, reagents that affect pH, counterion concentration, or the ionic character of the solvent) or materials (e.g., nucleation promotors) could be added during the processing of the samples. The specific composition of each sample in an array might be the same (to allow redundancy) or different (to allow the simultaneous testing of numerous crystallization conditions). However, the invention also encompasses the use of arrays to attempt the crystallizations of compounds-of-interest from melts, in which case the samples might only contain solid compound-of-interest.

In another example, the array is used to determine various characteristics of a compound-of-interest, or how they change when exposed to particular conditions (e.g., those described below in the Sample Handling and Processing section). Examples of characteristics include, but are not limited to, form, chemical composition, solubility, physical and/or chemical stability, and hygroscopicity.

Whatever the purpose to which an embodiment of this invention is put, each container (apart from any containers used as controls, or blanks), will comprise a controlled amount of the compound-of-interest and, optionally, one or more additional compounds (e.g., solvents, excipients, or nucleation agents). The containers may also contain a stirbar or other device to facilitate stirring, uniform heating, or anything else that is deemed necessary for the partcular use to which the invention is being put. All of these materials are preferably added to containers in an automated fashion. For example, compounds-of-interest and solvents can be deposited into the vials in a variety of ways, ranging from hand-pipetting to automated liquid and/or solid dispensing. Dispensing of chemicals into the vials is preferably accomplished with an automated reagent dispensing apparatus, such as Cartesian Technologies' PreSys model (available from Cartesian Technologies Inc., 17851 Sky Park Circle, Suite C, Irvine, Calif. 92614, USA), and multiple-channel liquid dispensers, such as those available from Tecan Group Ltd. (Tecan Group Ltd., Seestrasse 103, 8708 Männendorf, SWITZERLAND). Other models and brands of liquid dispensers can also be used. Solid compounds and compositions can also be dispensed by hand or by automated means known in the art. For example, a solution comprising a compound-of-interest can be dispensed into sample containers, after which the solvent can be removed to provide a controlled amount of the compound-of-interest (e.g., in a milligram or microgram quantity).

After samples have been prepared, the containers that hold them are preferably sealed to prevent leakage, contamination, and evaporation (unless otherwise desired), as well as to prevent outside factors (e.g., humidity changes) from affecting the samples. Preferred containers are vials which can be sealed using crimpable metal caps or compliant gaskets, such as a silicon frits or septa. Other means of sealing containers include, but are not limited to, wax plugs, threaded caps, caps that snap over the vial opening, and compression or adhesive seals. Preferred septa allow for the illumination of the contents of a container from the top, and also allow for the addition or withdrawal of materials or components to/from the tube. The capping or sealing of the containers is preferably accomplished using an automated means, such as a Wheaton Crimpmaster Crimping Station (Wheaton Science Products, 1501 No. 10$^{th}$ Street, Millville, N.J. 08332, USA) pneumatically powered crimper. Alternatively, hand powered crimper tools (also Wheaton Science Products) may be used.

The invention encompasses the labeling of either the vial itself or the crimped seal cap that allows the ready identification of individual samples. Both crimp caps and glass vials may be labeled, for instance, through laser and inkjet marking, by using human-readable, alphanumeric codes, as well as using machine-readable codes such as DataMatrix 2-D codes. Such codes may advantageously be scanned and tracked with optical readers. Similarly, other types of barcodes and marking technologies may be used without limitations.

4.2 Sample Handling and Processing

Particular embodiments of the invention encompass exposing the samples in an array to one or more conditions such as, but not limited to, pH, ion concentration, solvent, temperature, and light for a particular amount of time. A typical condition is temperature, and one embodiment of the invention encompasses a thermal cycling system capable of processing many blocks simultaneously. This system comprises one or more shelves, preferably thermally conductive, onto which blocks can be placed, and heating and/or cooling means such as, but not limited to, chillers, baths (e.g., water), dry baths, hot plates, temperature-controlled rooms, ovens, thermoelectric devices, such as devices employing Peltier-effect cooling and/or joule-heating, and environmental chambers. The temperature of the samples can be controlled by heating or cooling the thermally conductive shelves.

The thermal cycling system can be used to simply incubate an array of samples at a specific temperature for a particular time (isothermal incubation), or can be used to cycle their temperatures, e.g., to vary their temperature as a function of time. When employed, thermal processing comprises varying the temperature of the contents of each vial in a controlled cycle, usually a heating period followed by a cooling period. Heat transfer through the blocks that hold the arrays of containers changes the temperature of the containers. Thus, when thermal processing is used to process the samples, the blocks used should allow heat transfer between a heating/cooling source (e.g., thermally controlled shelves) and the sample containers (e.g., vials).

Figure 4A:
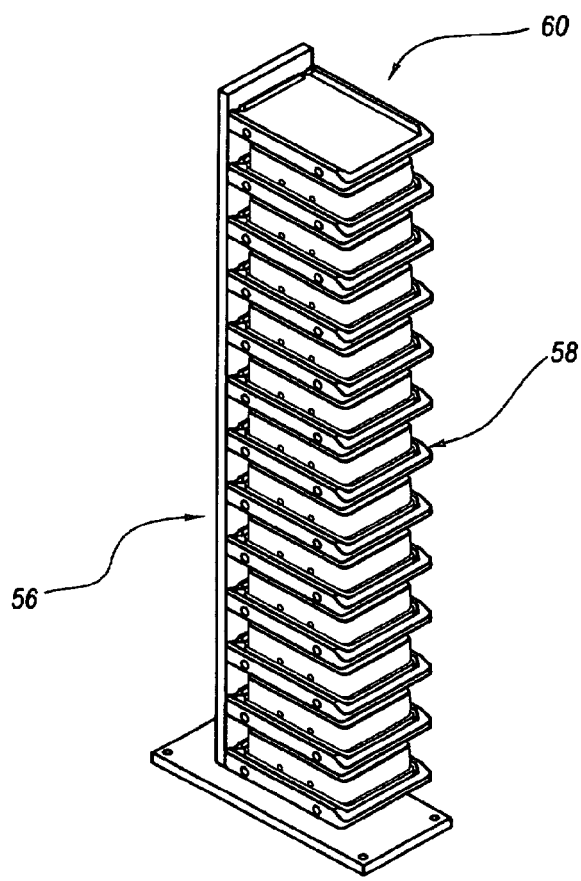
FIG. 4A is a drawing of a temperature-controlled shelf assembly, or "hotel," loaded with twelve blocks.
Figure 4B:
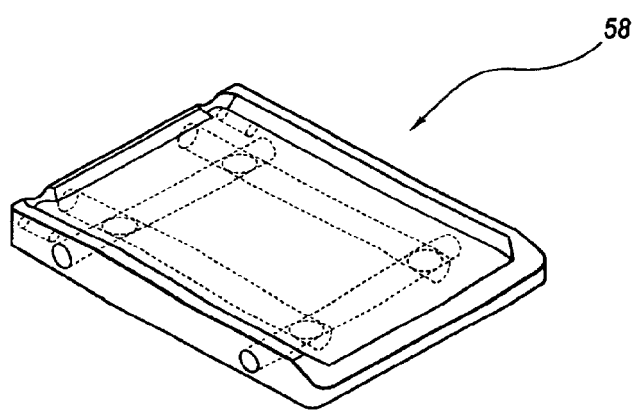
FIG. 4B is a drawing of a shelf equipped for use with a heating/cooling loop (e.g., using water, ethylene glycol, or another solvent) shown as dotted lines.
Figure 5:
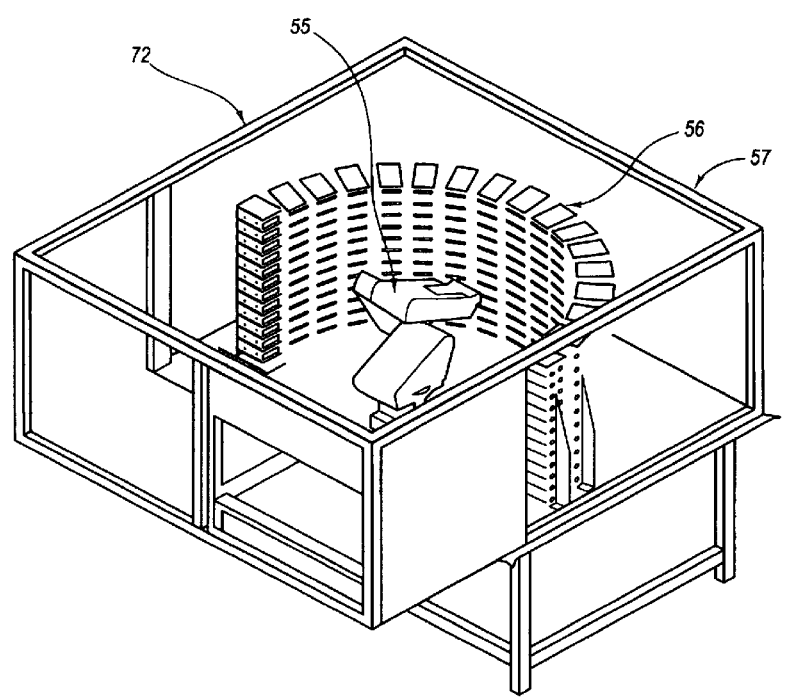
FIG. 5 shows a drawing of a thermal cycling system top-level assembly, including an environmental enclosure. In this arrangement, 18 hotels in a semi-circular pattern around a robotic arm are shown.

FIGS. 4A–4B illustrate a specific example of a thermal cycling system, which comprises temperature-controlled shelf assemblies 56, which are also referred to herein as "hotels." A number of hotels can be arranged to a number of different blocks. FIG. 5 provides an illustration of one example of a thermal cycling system, which comprises 18 hotels 56 in a semi-circular arrangement around a robotic arm 55. In a preferred embodiment, a hotel comprises twelve shelves 58 arranged in a vertical fashion as shown in FIG. 4A, held in place with supporting members and incorporating locating features for securing the assembly in the desired position. In a preferred embodiment, each individual shelf 58 contains an internal loop through which a liquid, such as water, is circulated to control the shelf temperature. The loops are piped to a bath, e.g., a water bath acting as the cooling/heating source. Finally, the thermal cycling system can optionally include an environmental-control enclosure 57 that regulates the humidity and/or ambient temperature of the air surrounding the blocks, preventing condensation on the containers and other components. One embodiment of an environmental control system 57 is shown in FIG. 5. Alternatively, the thermal cycling system can be located in an environmentally-controlled room.

In a specific embodiment of the invention, different water baths (which may also employ various other fluids for conducting heat or cold to the samples) allow for the processing of multiple blocks at different temperatures. The blocks are located in hotels that are connected to the baths, the temperatures of which are computer controlled. In this embodiment, computers also record the heating/cooling time and temperature for each assembly of shelves, or "hotel." Because each block contains a plurality of sample containers, each of which is identifiable by is location in the block and/or the use of a bar code or other identifier, the conditions to which each sample in a given hotel is exposed is recorded and tracked by computer.

The processing of samples or arrays of samples can involve more than simply subjecting the samples to a particular temperature or range of temperatures. For example, the samples can be exposed to other environmental conditions, such as humidity, using an environment-controlled room. As shown in FIG. 5, environment control is achieved in one embodiment of the invention using an enclosure 57 that surrounds the shelf assemblies 56, and is connected to a supply of air that has been treated to provide the desired humidity level inside the enclosure.

Samples in an array can be processed in any number of ways. For example, samples in an array can all be subjected to the same temperature for the same amount of time, or can be processed individually using, for example, robotic techniques. For example, a solvent or antisolvent can be added to just one or a few of the containers held in a block with the aid of automated dispensing devices and robotic arms, such as that shown in FIG. 5.

Samples can also be subjected to a combination of different processes. For example, in what is referred to as a "mixed-mode" crystallization process, more than one processing mode is applied to samples in an array either serially or in parallel. For instance, thermal processing (described above), followed by anti-solvent addition to the container(s) and/or partial or complete evaporation of the volatile contents of the container(s) can be used to facilitate crystallization of a compound-of-interest. Here, the term "anti-solvent" refers to a solvent in which the compound to be crystallized has very low solubility. An evaporation process entails allowing the sample solvent systems to evaporate and may involve flowing a dry, inert gas over the samples and/or heating the samples to an extent and for a time sufficient to effect concentration of the compound-of-interest in the sample. In a specific example of mixed-mode processing, a thermal process is followed by an evaporative step in which the sample vessels are opened (uncrimped) and dry nitrogen is blown over the surface of the samples to promote evaporation of the solvent to an extent and for a time sufficient to allow crystallization. In another example of mixed-mode processing, a thermal process is followed by addition of an anti-solvent to the sample vessels in an amount sufficient to allow crystallization. In still another example of mixed-mode processing, a thermal process is performed on duplicate sets of sample formulations followed by an evaporative step on one set and anti-solvent addition to the other set. A mixed-mode crystallization process may conclude with an incubation step, where the samples are incubated at a temperature and for a time sufficient to allow crystallization. Any combination of individual process steps (e.g., thermal, anti-solvent addition, and evaporation) may be used in serially or sample arrays may be split to allow different process modes to be used in parallel.

Visual inspection of the samples is preferably done at least once during their processing (i.e., their exposure to one or more chemical or environmental conditions). Such inspection can occur at any time before, during, or after the processing of the samples, and is preferably done using automated means. For example, a robotic arm 55 as shown in FIG. 5 can be used to removed the blocks 60 from the shelves 58 and transfer them to an imaging, or vision station, such as that which is described below in Section 4.3 and elsewhere herein. Depending on the result of the imaging, the block can then be replaced onto a shelf in the thermal cycling system, or its containers can be separated, rearranged into new blocks, or removed entirely for more detailed (e.g., spectroscopic) analysis. As mentioned above, the location and processing history of each sample is preferably tracked and recorded, so that it can be located, analyzed, and reproduced at any time. Because each container can be imaged separately from others in the array to which it belongs, this invention allows the rapid identification of samples that can be further processed or removed for detailed analysis even when such samples are just a few of hundreds or even thousands of samples being processed.

In one embodiment of the invention, the processing of one or more samples in an array is stopped at a specific time using what is referred to herein as a "quenching station." It is at such a station that the condition(s) to which a sample is exposed are removed. For example, if the condition to which a compound-of-interest has been exposed involves contact with a particular solvent, the samples can be quenched by extracting any fluid component that remains in each container. This can be accomplished by puncturing the seal of the container, or tube, with a needle that can extract the liquid from the tube and provide a relief path through which air can flow into the tube, so as not to create a vacuum. In addition, samples can be air-dried after removal of the liquids in a vial by using a similar needle assembly to punch through the septum and inject dry air into the vial for a specific amount of time. The dry air (or other gases) removes remaining liquids from the sample through evaporation, and vents them outside the vial. As with sample preparation, quenching can be automated, and can be triggered by a human operator or by computer.

4.3. Sample Imaging

A result of conducting a large number of small scale experiments using various processing methods creates the need to interrogate or inspect each of the samples in the containers for the presence (or absence) of solid forms or other products of interest. Although visual inspection can be done manually, preferred embodiments of the invention utilize what is referred to herein as a "vision station," which is an automated system that allows for the rapid and efficient imaging and screening of samples. Preferred vision stations are designed for the analysis of samples contained in tubes and blocks-type arrangements, as discussed above in Section 4.1 and elsewhere herein.

In one embodiment of the invention, the vision station comprises a device for capturing an image of small particles, such as a microscope/camera system with a highly magnifying lens to capture images of small (down to sub-micron) particles onto a CCD such as the Canty Particle Size Vertical Imaging Microscope (JM Canty Inc., Buffalo, N.Y. USA). Another example is the published report from December 2000 on image analysis of protein crystals: *An optical system for studying the effects of microgravity on protein crystallization*, Alexander McPherson et al., application note from American Biotechnology Laboratory, December 2000 issue, which is incorporated herein in its entirety by reference.

Depending on the use to which the invention is put, sample imaging can be used to determine the presence of a solid form in a sample or container. Alternatively, the absence of solids can be also be detected. Consequently, vision stations of the invention can be used to determine the stability of liquid formulations (e.g., drug formulations for intravenous administration to patients) and the stability of a formulation in a simulated body (e.g., gastric) fluid.

Samples can be imaged at any time after their preparation. Consequently, imaging information can be used to determine whether or not a sample should be processed, how it should be processed, and whether or not it should be subjected to more detailed, (e.g., spectroscopic) analysis.

A typical vision station of the invention comprises a light source and a camera. A suitable camera can be any unit capable of yielding photographic images of the contents of containers, e.g., the presence or absence of solids or solid forms, but is preferably capable of digital capture. In a preferred embodiment of this invention, a charge coupled device (CCD) camera provides adequate sensitivity, but other digital capture devices may also be used. The light source is selected based on the types of containers being used and the design of the experiment. Examples of light sources include, but are not limited to, visible light, laser light of varying wavelengths, monochromatic laser, plane-polarized, or circularly polarized light. In an example embodiment, the light source is white light from one or more tungsten lamps. Depending on the mode of application of the vision station, light can be brought in from the top of the array, the bottom, or from the side. Blocks containing removable containers allow improved access by light to the sample due to the ability to elevate the containers from the block, either by hand, or using an automated means.

In one embodiment, the vision station system is adapted for use with the tubes and blocks system. In this embodiment, the vision station system comprises a camera, a light source, and, optionally, a mechanism to elevate containers (e.g., tubes) from a block, thus presenting the containers to the camera. The mechanism to elevate containers from a block can lift containers out of a block individually, or in groups, including without limitation, lifting all the containers in one or more rows or columns of a block at the same time, and preferably, lifting all the containers in one row or column at the same time. Additionally, the system can employ software to capture, store, and analyze images and digitally flag or select tubes containing contents of interest, e.g., solid forms, in a series of images. Furthermore, the vision station system may optionally comprise a database for warehousing of the results and collation of information on the identity, composition and history of samples in order to allow further detailed analysis of the combined data.

Ultimately, the vision station system enables the automatic selection of specific samples (or containers containing samples) from an array based on their appearance. Advantages of the vision station system include, but are not limited to, speed of acquisition coupled with the details of the solid form, such as gross crystal habit, color, form, and location of solids (e.g., crystals) in a container. Such information about where solid formation occurs (such as where a crystal nucleates, e.g., at the air-liquid interface or in the bulk solution), and shape of the crystals or precipitate is useful in studying and controlling crystallization. The vision station also provides many automation opportunities (both in hardware as well as in software analysis of images) and the ability to capture a variety of data regarding the detailed physical form of the compound-of-interest (e.g., its crystallinity, amorphous character, physical stability, and size range information). In terms of speed, embodiments of the vision station system can observe 96 sample tubes in less than one minute, and the image capture is rapid (on the order of 30 milliseconds with current digital camera technology).

In a specific embodiment of the invention, the vision station system can accept different arrays or blocks of containers for analysis in rapid succession. Using the vision station system, the information obtained can include: (1) detection of solids based on illumination (e.g., white light) and image capture; (2) observation of birefringence (backlit crystalline samples seen with the help of cross-polarized light); (3) observation of nanoparticle presence (using laser beams at various angles to the camera lens); and (4) temporal information (nucleation kinetics and kinetic stability of colloidal suspensions toward growth and phase separation are two examples). In addition, automated exemplary and example machine vision algorithms further enhance the utility of the system by obviating the need for a user to manually select tubes that are of interest.

Figure 6:
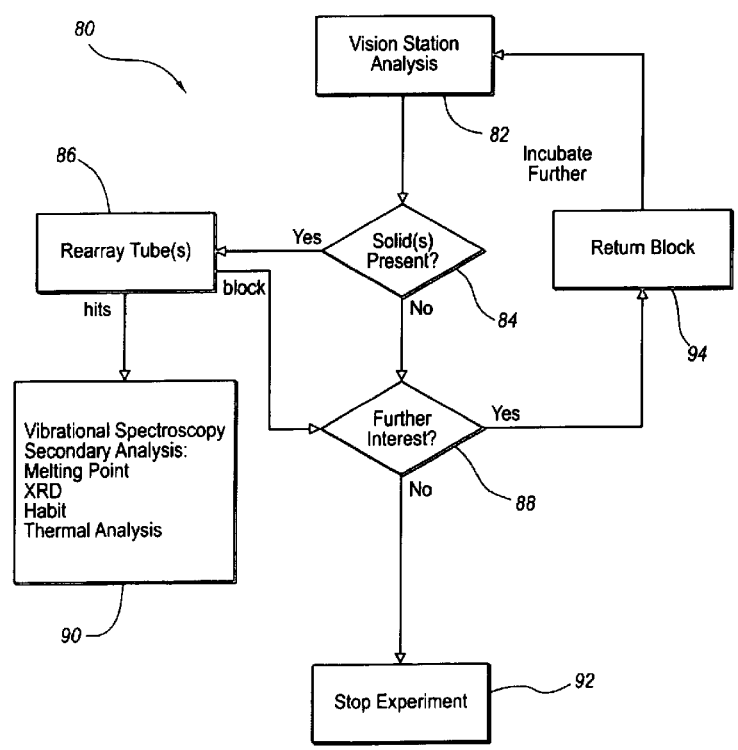
FIG. 6 shows a flowchart depicting an example of the logic for addressing solid form generation using the vision station approach.

In another specific embodiment, the vision station system is adapted to process blocks that contain about 96 containers in an arrangement of 8 rows of 12 columns. FIG. 6 illustrates the logic used in one embodiment to address solid form generation using the vision station approach. The embodiment in the flowchart 80 involves tubes in blocks, but the process can be adapted for use with other container systems. This embodiment comprises a vision station analysis 82, which includes optical inspection of vials holding samples. If no solids are detected 84 in the vial, a determination is made whether or not that particular reaction is of further interest 88. If it is not of further interest, the experiment may be stopped 92 for that particular vial. If a sample in a vial is still of interest, it may be returned to the block 94 and sent back for further processing, such as in the thermal cycling system. The process may then be repeated as to that vial. Alternatively, it may be removed without further processing. If the experiment is designed to detect solids, vials that contain solids are sent to a re-arraying process 86 whereby multiple vials with solids present are grouped together in the same output block. At every step, the address of each vial is tracked and updated if necessary. Such tracking can be done using various methods known to the skilled artisan, including without limitation using bar codes. Optionally, the entire output block can then be sent for detailed (e.g., spectral) analysis 90. The output block is preferably entirely filled, but it need not be.

Figure 7A:
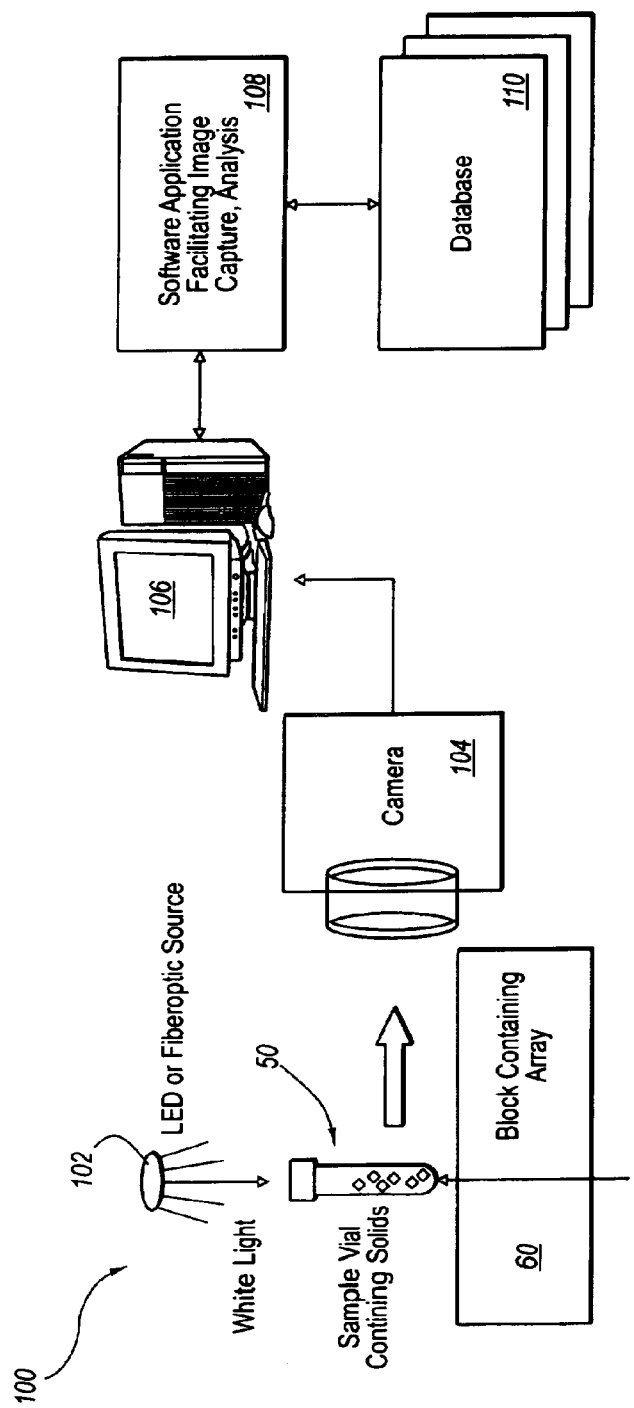
FIG. 7A is a schematic diagram of a specific vision station.
Figure 7B:
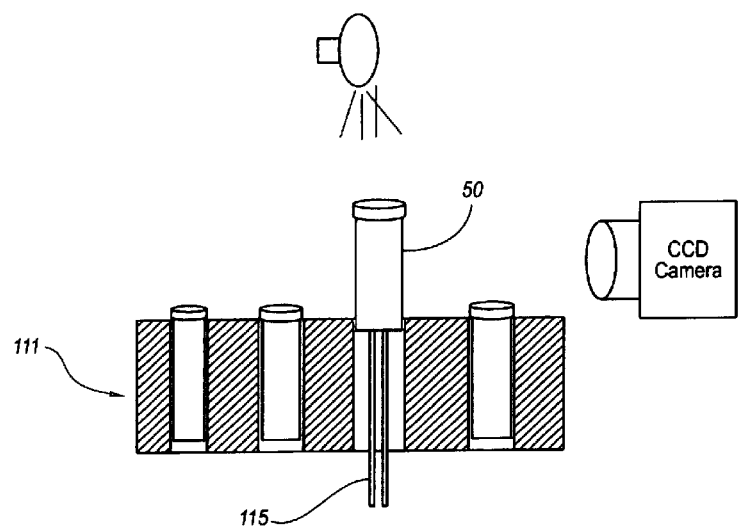
FIGS. 7B and 7C are drawings of a vision station in operation, showing a side view (FIG. 7B) and a perspective view (FIG. 7C) of the block wherein a lifting mechanism lifts an entire row of vials at the same time. The light source can be positioned on top of the samples (e.g., normal to the CCD camera) or opposite the samples.
Figure 7C:
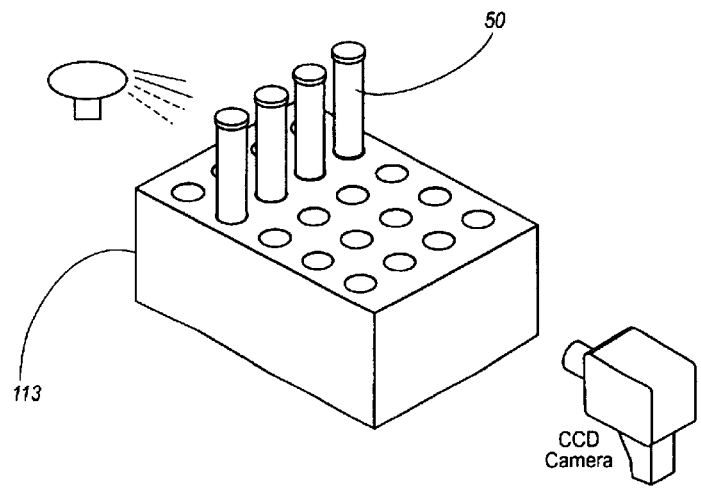

FIG. 7A shows a schematic diagram 100 of a vision station. A block 60 containing an array of vials 50 is placed before an imaging device 104. While it is recognized that a camera can be oriented underneath the block so as to be capable of viewing the contents of the vials through the access holes in the bottom of the block, the preferred embodiment contemplates raising the vials at least partially out of the blocks into view of the imaging device. Thus, FIGS. 7B and 7C are drawings of a vision station in operation, showing a side view 111 (FIG. 7B) and a perspective view 113 (FIG. 7C) of the block 60, wherein a lifting mechanism 115 lifts an entire row of vials 50 at the same time. Alternatively, vials 50 can be lifted one by one.

As shown in FIGS. 7A–7C, vial 50 is illuminated by a light 102 that can be placed in a variety of locations to light up different portions of the vial 50, depending on where in the vial 50 illumination is desired. The level of illumination is determined by inspecting the resulting images for the desired contrast and is controlled by the operator adjusting the level or voltage until the desired contrast is obtained. Alternatively, the level of illumination can be automatically adjusted using appropriate sensors and/or algorithms. The resulting illumination provides sufficient contrast for an image or picture to be captured. Various software 108 can be used to capture the image, such as Component Works IMAQ Vision (National Instruments). In a preferred embodiment, the image capture software is integrated into a custom VB software. The camera 104 then takes a picture of the vial 50. The picture is then stored on a computer. A hardware card, such as National Instruments Image Capture Card, model number PCI-1422, is used to capture the image in conjunction with image capture software 108. A custom software application then displays the picture of the vial and the vial can then be designated as containing various results, such as, but not limited to, solids, lack of solids, sediment, phase separation. The pictures and the vial 50 designations can then be stored in a database 110. The process is repeated for all of the vials 50 in a block 60, and for all the blocks in a given experiment run or design. The vials can be all processed at one time, or it can be done intermittently.

A preferred embodiment of the vision station system comprises a camera 104, preferably a CCD camera, for example, a CCD camera manufactured by Roper Scientific (model MegaPlus ES:1.0) (now Redlake MASD, Inc., 11633 Sorrento Valley Road, San Diego, Calif. 92121 USA) with an 9×9 mm image array with a total of 1008×1008 pixels. Another suitable source of imaging cameras is Spectral Instruments, Inc., Tucson Ariz. that provides a CCD camera that can be cooled to −50° C. Alternatively, image plate technology based on CMOS can be used for obtaining images, but CCD is the preferred capture mechanism.

In one implementation, an area of the width of roughly 72 mm is observed when 8 tubes (a row at a time) are pushed out of a block for vision analysis, although, for instance, tubes may be viewed in groups of fewer than 8 such as single tubes or two tubes per captured image. This observed area leads to a pixel resolution of about 70 microns/pixel. A resolution range from about 5 to 1000 microns is useful in the many embodiments of this invention, since most organic crystalline materials in a powdery state range in particle size from a few microns to hundreds of microns. Single crystals are often a few hundred microns on the shortest edges, while on the other hand extreme colloidal particles, such as titania ($TiO_2$) and silica ($SiO_2$) can be stably prepared in the nanometer size range.

The vision station can be used to identify amorphous, as well as crystalline, solids. The amorphous form can be of significant interest with regard to certain compounds-of-interest, such as, but not limited to, increased solubility relative to crystalline forms. Generally, amorphous forms of a given compound are thermodynamically unstable compared with crystalline forms, but can be rendered kinetically stable toward physical form change, e.g., as a glass. Amorphous particles are typically irregular in size, and the material lacks the property of optical birefringence. This is defined as the ability of most crystalline materials to interact with polarized light by changing the direction of the polarization as it passes through the crystals. Plane-polarized light is generally rotated upon traveling through a crystalline material. If the light is subsequently sent through an analyzing filter (this is another plane polarized filter where the polarization direction is 90 degrees perpendicular to the first filter) at a right angle to the plane-polarizing filter on the light source, the rotated light escapes the analyzer. Therefore true crystals appear as bright spots on a dark background. Conversely, amorphous disordered materials generally do not rotate plane-polarized light such that minimal light (equal to background) escapes the filter resulting in a dark image. It may be advantageous to look for the presence or absence of crystallinity in this way, and by comparison of birefringence image with the plain image rather than simply looking for the presence of solids.

The lighting used to capture white light images of elevated tubes is flexible, in that it can be brought in (a) from the top of the tubes (if the top is either open or any seal is transparent), and (b) from the side of the tubes, behind the camera. The latter is referred to as backlighting and this approach is required when one wants to capture birefringence information. In principle, the light can be brought in at a number of angles, but the preferred orientations are either vertical or horizontal. The lighting can be provided by fiber optics (for example, NT39-366 from Edmund Industrial Optics, 101 East Gloucester Pike, Barrington, N.J. 08007), although white light strips (for example, Stocker Yale, Imagelite brand) can also be used. Various polarizing filters can be obtained from a number of commercial sources, e.g., polarizing filters, such as NT45-669, are available from Edmund Industrial Optics.

Figure 8:
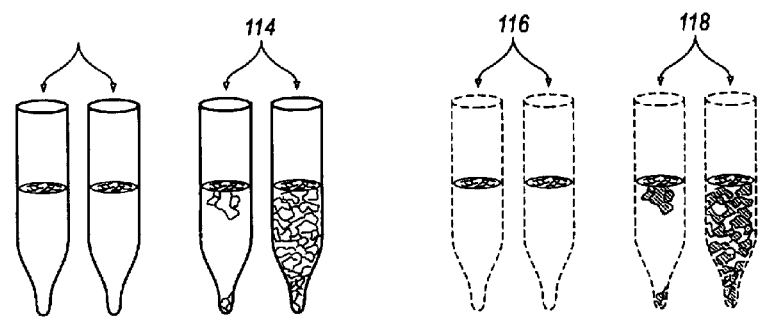
FIG. 8 is a drawing that shows the difference between samples with no birefringence and samples with birefringence.

FIG. 8 illustrates an embodiment of the vision station adapted for the detection of birefringence. On the left side, a pair of tubes with water 112 and another pair of tubes with varying amounts of glycine crystals 114 are shown with backlighting without a polarizing filter on the camera lens. On the right are the same samples 116 and 118 with a polarizer in place. With use of color images, one can capture polychromism (i.e., multi-color crystals) information from the experiment with a suitable camera, or simply run the analysis with black and white images and look for bright pixels. In addition, a quarter-wave retarder filter can be used to confirm the presence of crystals by causing a color shift when the filter is applied.

Figure 9:
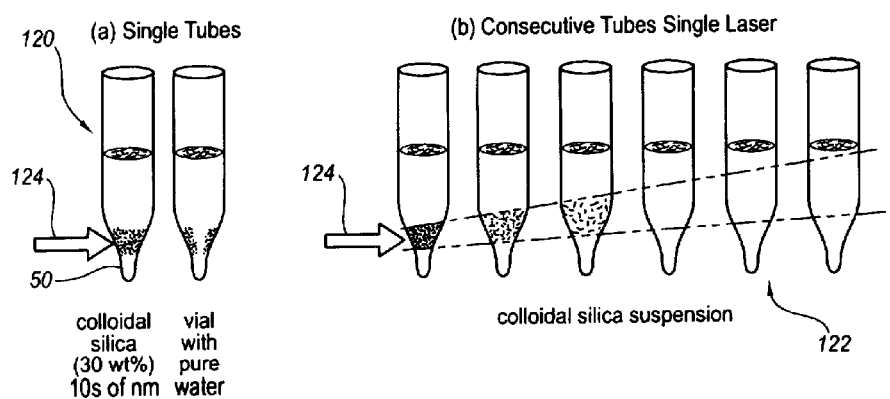
FIG. 9 is a drawing showing the scattering and diffusion of laser light pointed at a single tube and consecutive tubes.

FIG. 9 shows the use of a combination of white light and laser scattering. A laser beam 124 (which can be of any color, such as red, green, or blue) can be brought into proximity with a tube or vial 50. Single tube analyses are typically preferred, due to some scattering and diffusion of the laser beam in cases where one attempts to send the beam 124 through several tubes consecutively (FIG. 9B). The laser beam, which can be generated by any number of laser devices such as with a He—Ne Class II laser pointer at <1 mW power, will interact with sub-micron particles inside the tubes and the radiation is scattered, resulting in a contiguous trail of laser light through the tube. If no significant colloidal component is present (the sample is a true solution) no such trail of laser light will be observed in the image. Using this application, the vision station system with the laser beam can be used to obtain kinetic information regarding colloidal stability (i.e., how long it takes a suspension to settle or ripen to microcrystals), solution physical stability (how stable is a solution toward nucleation), or phase segregation.

Figure 10:
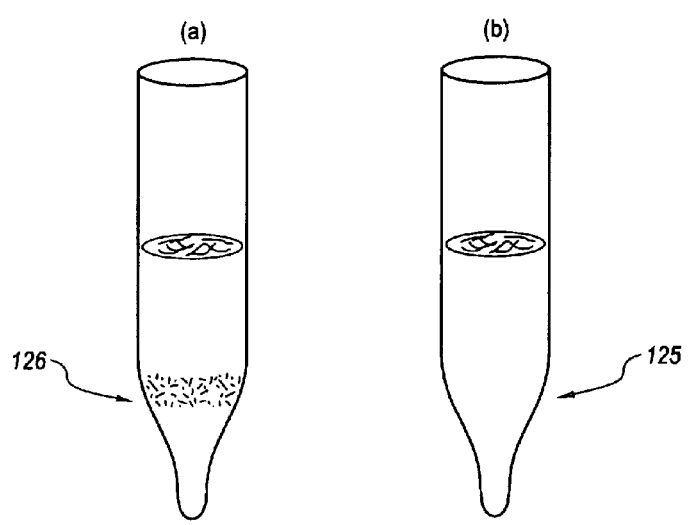
FIG. 10 is a drawing that shows the effect of illuminating of a tube containing a colloidal suspension (a) compared to a tube containing pure water (b).

Another embodiment of the invention utilizes laser light at an angle different from 90 degrees (e.g., at a 45 degree angle) relative to the camera lens. This is shown in the example of FIG. 10, where the image 126 in panel (a) clearly shows a contiguous path of laser light due to the presence of the colloids. In contrast, the image 128 in panel (b) shows a single point of scatter on the right side of the tube (where the laser beam hits the tube). This effect is due to partial scattering of the laser light by the glass, and becomes more pronounced in the image as the angle between the camera lens and the laser beam is decreased.

Figure 11:
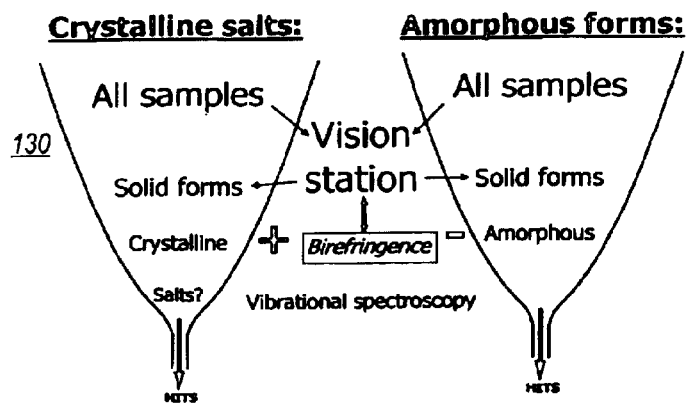
FIG. 11 is a flow diagram depicting the use of the vision station to detect birefringence in crystalline solid forms, or to differentiate crystalline versus amorphous solid forms by the observance of birefringence.
Figure 12:
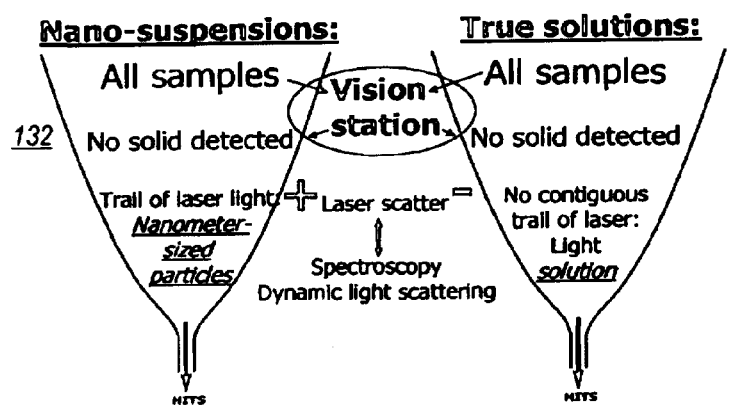
FIG. 12 is a flow diagram depicting the use of the vision station for laser light interrogation of samples. Shown are diagrams of nano-suspension compared to true solutions.

FIGS. 11 and 12 show flow charts for the logic used in specific vision station systems for the detection of birefringence 130 and laser light interrogation 132, respectively. The funnel widths roughly represent the number of samples at a given stage of the experimental workflow. The charts illustrate how a vision station system can facilitate analysis of crystallinity or lack thereof in a set of solid forms (FIG. 11), and also allows analysis of nano-particulate and true solutions along with the stability of each (FIG. 12).

In a preferred embodiment, the analysis of images obtained by the vision station is automated. For example, software (e.g., National Instruments IMAQ VISION software) is employed in image acquisition and analysis. When image analysis is performed manually, an operator flags the samples that satisfy the criteria used in the particular experiment (e.g., which ones contain a solid) using a software interface. Such software can perform a variety of function, such as, but not limited to, automated capture and storage of images, creating and storing logic for each sample (e.g., which ones contain solid, was a sample in solution at the start of the experiment), and ultimately containing algorithms for time-based measurements as well as automated isolation of containers that satisfy given criteria. Such software can also inform the user which samples are of interest, and facilitates the re-array of hit tubes from the source block into a destination block for further off-line processing or characterization. Preferred software provides an actual image of vials that allows a user to observe and manually select vials of interest for further processing.

In another specific embodiment of the invention, the vision station system further comprises a means of determining the optimal laser light configuration relative to the tubes for interrogation of colloidal suspensions (e.g., as to the size of the particles they contain). In another embodiment, the vision station system comprises a means of optimizing the capture of birefringence information, including the investigation using a quarter wave plate and other filters in concert with plane or other polarizers to ensure that light scattering is not interfering with image analysis and interpretation.

In a specific embodiment of the invention, once a number of blocks have been processed through the vision station system, there will be one or more output blocks holding vials containing solids. Optionally, in a preferred embodiment, these blocks are then processed further (e.g., moved to a quenching station) as described above in Section 4.2 and elsewhere herein.

4.4. Spectroscopic Data Collection and Analysis

In a typical embodiment of the invention, one or more samples in an array are analyzed using spectroscopic techniques. In preferred embodiments of the invention, the sample(s) that are analyzed have been screened or selected (e.g., using the methods or devices described above in Section 4.3) from an original array of samples. For example, the vision station can be used to identify samples that contain solids, and the contents of those samples are then analyzed further using spectroscopic techniques.

The specific analysis done will depend on the purpose to which a particular embodiment of the invention is put. For example, if the invention is used to prepare solid forms of compound-of-interest, the solids that have been identified in samples can be analyzed to determine their chemical and physical form, e.g., whether they are salts or solvates (e.g., hydrates) of the compound-of-interest, whether or not they are crystalline, and, if they are crystalline, the nature of their crystal form (e.g., their crystal structures). Spectroscopic analysis can also be used to determine if any of the compounds in a sample (e.g., the compound-of-interest) decomposed or reacted with other compounds in that sample.

Spectroscopic techniques can also be used to identify samples that share one or more characteristics. For example, if a solid compound-of-interest can exist in more than one solid form, and each of a plurality of samples comprises solid compound-of-interest, it may be desirable to identify which samples contain compound-of-interest of which form. The grouping of samples as a function of a particular characteristic (e.g., a spectral characteristic unique to a particular solid form) is referred to herein as "binning." Such binning provides a means of avoiding unnecessary duplication of further experiments. For example, if a group of samples are binned based on a particular spectral characteristic which corresponds to a previously unknown solid form of the compound-of-interest, further analysis of that solid form need not require a detailed analysis of each sample in the group.

Examples of spectroscopic techniques that can be used to bin or analyze samples are numerous, and will be readily apparent to those skilled in the art. Some specific examples include, but are not limited to, optical absorption (e.g. UV, visible, or IR absorption), optical emission (e.g., fluorescence or phosphorescence), Raman spectroscopy (including resonance Raman spectroscopy), nuclear magnetic resonance spectroscopy (e.g., single and multi-dimensional $^1$H and $^{13}$C), X-ray diffraction (e.g., powder X-ray diffraction), neutron diffraction, and mass spectroscopy. For the sake of convenience, other methods of analysis are encompassed by the term "spectroscopic technique," as it is used herein, include, but are not limited to, microscopy (e.g., light and electron microscopy), second harmonic generation, circular dichroism, linear dichroism, differential scanning calorimetry (DSC), thermal gravimetric analysis (TGS), and melting point. Preferred embodiments of the invention utilize Raman spectroscopy.

4.4.1. Raman Spectroscopy

The use of Raman spectroscopy for the high-throughput screening and/or analysis of multiple samples is believed to be novel, particularly in view of the relatively low intensity of Raman scattering as compared to other spectroscopic techniques. When coupled with the devices and techniques disclosed herein, however, Raman spectroscopy has been found to be particularly useful in the high-throughput screening and analysis of samples.

The Raman spectrum of a compound can provide information both about its chemical nature as well as its physical state. For example, Raman spectra can provide information about intra- and inter-molecular interactions, inclusions, salts forms, crystalline forms, and hydration states (or solvation states) of samples to identify suitable or desirable samples, or to classify a large number of samples. With regard to the hydration states of molecules, methods and devices of this invention, particularly the binning methods discussed in more detail below, allow their determination in situ.

Raman spectroscopy can also be used in this invention to examine kinetics of changes in the hydration-state of a sample or compound-of-interest. Moreover, the ability of Raman spectroscopy to distinguish, in certain situations, forms with different hydration states is comparable to X-ray diffraction, thus promising specificity and sensitivity. The lack of a strong Raman signal from water, a common solvent or component in preparations allows collection of Raman data in-situ in a manner relevant to many applications.

This invention also encompasses the use of Raman spectroscopy to determine the amount of a compound-of-interest that is dissolved in a particular sample. Advantageously, it has been discovered that for many compounds-of-interest and solvents, a correlation between the amount of compound-of-interest dissolved in a liquid sample and certain characteristics of its Raman spectrum can be obtained using one solvent, yet can be applied to the high-throughput analysis of samples prepared using a variety of other solvents.

These and other aspects of the invention are made possible by the utilization of several devices and methods described herein, which overcome problems inherent to Raman spectroscopy that would otherwise limit its usefulness as a high-throughput analytical technique. Examples of such problems include, but are not limited to, weak signals, background (e.g., solvent) emissions, and signals due to other solids or liquids in a sample, as well as the sample container itself.

Improvements in reproducibly obtaining Raman spectra for samples of interest include rapid and sensitive spectra acquisition and rejection of background noise. The strength of Raman emissions is improved by the use of lasers to excite the target substance. Use of a carefully selected wavelength also results in resonance Raman spectra. Sample preparation techniques resulting in adsorbing of a target to a surface further increase Raman signals, although such preparation is not always possible or desirable in the case of in-situ data collection. Since the strength of the Raman signal can vary depending on many factors, it is important to use on-line data analysis in order to determine when a sufficient quality and quantity of data have been collected to meet the goals of the measurement (e.g. a prescribed signal-to-noise threshold). Of course, optical amplifiers further improve sensitivity and specificity. Each of these techniques or process steps may be used alone or in combination.

Filtering techniques encompassed by the invention that can be used to reject noise include but are not limited to temporal, spatial, and frequency domain filtering. Spatial filtering requires collecting emissions from a small area to reject noise from surrounding sources. Such confocal techniques, for instance with the target in the focus of an objective and/or using a pinhole arrangement, allow scanning of a target to reduce unwanted noise due to emissions from the material surrounding the target area.

The invention also encompasses temporal filtering, which rejects or accepts signals received in a particular time window. In the case of Raman spectra, temporal filtering relies on the different times taken for emission of Raman spectra and the background fluorescence spectra. Notably, Raman emissions, although weak, can be detected much earlier than fluorescence following excitation. Furthermore, fluorescent radiation continues over a significantly longer period, thus making possible selection of time windows for collecting Raman signal with a higher S/N ratio than otherwise. An example of such filtering is provided by Matsousek et al. in "*Fluorescence suppression in resonance Raman spectroscopy using a high-performance Picosecond Kerr Gate*," in *J. Raman Spectroscopy*, vol. 32, pages 983–988 (2001). The Kerr gate realized by Matousek et al. exhibits a response time of about 4 picoseconds, thus allowing collection of Raman emissions during a window of 4 picoseconds following an exciting laser pulse. This example should be regarded as illustrative and not limiting as to temporal considerations in collecting and filtering spectra in possible embodiments since other gates, including virtual gating techniques are also intended to be within the scope of the claimed invention. Such filtering techniques, which can be used separately or together, can be augmented with mathematical filtering, e.g., convolution with the characteristic shape of a Raman line to further reduce the noise and reject unwanted frequencies and emissions.

In another aspect, the invention encompasses the use of polarized excitation and detection. Raman scattering emissions are sensitive to the orientation of the polarization of the exciting light relative to the molecules being examined. If the exciting light (typically from a laser) is polarized and the molecules in a crystal have fixed orientations, the Raman signal varies as a function of the orientation of the crystal. This property, while useful for detecting and evaluating crystalline samples, presents challenges in collecting representative Raman spectra due to the change in the amplitude of individual lines. The use of spectral binning, which is discussed elsewhere herein in more detail, can be used to overcome such challenges. Following the collection of a plurality of spectra that are, optionally, preprocessed to remove contaminating signals, as described more fully below, it is possible to identify peaks in each of the spectra. Optionally, from these identified peaks of the spectra it is possible to generate, for instance, a peak height or binary spectra reflecting the peak positions. The use of binary spectra reduces the computational overhead in binning and otherwise interpreting the data while taking into account variations due to orientation and the like. Filtered raw spectra, peak height spectra generated from identified peaks of filtered raw spectra, or binary spectra may be used to calculate similarity scores using any suitable metric, and the similarity scores allow binning of the spectra in accordance with various clustering techniques.

4.4.2. Data Collection

Spectroscopic data can be obtained for one or more samples by manually removing the containers that contain them from the block holding them, and presenting the containers to the particular analytical device being used (e.g., Raman spectrometer). Preferably, a mechanical system (such as an automated robotic arm) is used to select, or "cherry-pick," particular containers (e.g., those identified as satisfying certain criteria by the vision station) from the block(s) that contain them.

In a specific embodiment of the invention used to detect and/or characterize solid forms of compounds-of-interest, a container is presented to a Raman spectrometer, and is imaged down the centerline at predetermined x, y positions. At each x, y position, two predetermined z positions are selected in order to focus imaging on the upper and lower inside face of the container (e.g., the upper and lower inside glass faces of a glass tube). Preferably, at least one position is used to focus imaging. This image acquisition step is repeated for different angles of rotation of the container until the entire inside surface of the container (e.g., glass tube) is imaged. After each image capture, an analysis is performed to determine where the "areas of interest" in a container are, where "areas of interest" can include solids or solid forms (e.g., crystals), and in some instances, any remaining droplets of solution or solvent.

A vision algorithm designed to automatically detect areas of interest (e.g., solid forms) in a container carries out the following: 1) locates or recognizes the presence or absence of a container; 2) locates the meniscus, if any, of the sample in a container; and 3) searches the area between the meniscus and the bottom of the container for particles, solids, solid forms, or other areas of interest.

After identifying areas of interest in a container, the Raman stage is moved to the center of the excitation source (e.g., laser) on to each of areas of interest in a container, and the Raman detection apparatus is focused using manual or automated means.

In one embodiment, auto-focusing of the Raman spectrometer can be performed. One way in which auto-focusing can be performed is by taking a series of Raman spectra at various z positions (to change the focus), for each x, y position representing an area of interest in a container. The one with the "best" Raman signal is marked, wherein the "best" Raman signal is defined by predetermined criteria, including, for example, by filtering each spectrum for a location and taking the maximum peak other than the normal peak associated with the effects of the container (e.g., glass tube). The resulting series of "best" Raman spectra for various areas of interest in a container can then be sorted based on similarities, and clustered into bins with spectra from other containers in an experiment. Automated focusing of a Raman spectrometer can result in a series of "best" Raman spectra for various areas of interest. These spectra can be sorted to distinguish droplets of solution or solvent from solids and clustered with data (spectra) from the other containers in the experiment.

When multiple spectra are obtained, one or more of the following can be also done: (1) find the one "best" spectra of a set of spectra for an area of interest or a solid form, with best being defined in a predefined way, including without limitation, highest peak signal, highest average signal, best S/N ratio, most peaks, and the like; (2) construct an average spectrum of all the spectra for an area of interest or a solid form, and use this spectrum in further processing; (3) construct an "agglomerated spectrum" that contains the highest peak of the set for every peak window, wherein a peak window is defined as a region in which peaks are considered to be the same; and/or (4) keep all of the spectra and perform downstream analysis on all of the spectra.

In processing (e.g., sorting and clustering) spectral data, the knowledge that several spectra come from each sample can used to score the clustering results, or the labeled spectra can be used to influence the clustering run. For example, a k-means clustering run can be altered in the following manner: for each step of the k-means run, cluster assignments are made in the traditional sense, such that each point is assigned to the cluster with the nearest centroid, resulting in precluster assignments that are not the final assignments for the step; the precluster assignments for all points coming from the area of interest or solid form are then compared, and the most popular cluster assignment is assigned to all of the points in the group as the final assignment; and new centroids are determined from these final cluster assignments.

4.4.3. Data Analysis

In particular embodiments of the invention, spectroscopic data is processed using what is referred to herein as a "spectra binning system," which allows the rapid analysis and identification of samples in an array by creating, for example, a family or similarity map. Preferred embodiments of the spectra binning system comprise a hardware-based instrumentation platform and a software-based suite of algorithms. The computer software is used to analyze, identify and categorize groups of samples having similar physical forms, thus identifying a group from which the operator, or scientist, can then select a few samples for further analysis. This selection can be performed independently by the scientist or using an automated means, such as software designed to automatically select samples of interest. Although, many applications made possible by the spectral binning system will be apparent to those skilled in the art, preferred systems of this invention is used to identify and characterize samples or compounds-of-interest. Particular binning and analytical methods useful in the invention are disclosed in U.S. patent application Ser. No. 10/142,812, filed May 10, 2002, the entirety of which is incorporated herein by reference.

The spectral binning system is generally used in this invention to detect similarities in the properties of a plurality of samples by observing their binning behavior. Thus, the number of forms of a substance can be estimated by binning spectra. The plurality of samples are examined with a device for generating a corresponding spectrum of acceptable quality, i.e., sufficient S/N ratio. Spectral peaks or other features are next identified to obtain a binary fingerprint. Advantageously, the spectra are compared pairwise in accordance with a metric to generate a similarity score. Other comparisons that use more than two spectra concurrently are also acceptable, although possibly complex.

One or more clustering techniques can be used to generate bins that are preferably well defined, although this is not an absolute requirement since it is acceptable to generate a reduced list of candidate forms for a given substance as an estimate of the heterogeneity of the substance's structure. Advantageously, the generation of bins facilitates the ready evaluation of structure heterogeneity among samples. For instance, frequency, frequency shift, amplitude, and other similar measurements based on Raman spectra are often limited by the lack of suitable standards. However, the number of bins generated from evaluation of Raman spectra obtained by sampling a substance of interest is a measure that does not directly depend on having a good standard.

The invention also encompasses the use of hierarchical clustering to represent the data in the form of a similarity matrix having similar spectra/samples listed close together. Such a similarity matrix may be sorted to generate similarity regions along a diagonal. The resulting sorted similarity matrix may be used as a basis for setting the number of clusters for k-means clustering or other clustering techniques based on a specified number of clusters such as Gaussian Mixture Modelling.

Advantageously, although the clusters are actually in higher dimensional space, they can be projected into 2 or 3 dimensional space and visualized. Therefore, the binning procedure allows for both steady state and kinetic evaluation of states (e.g., hydration states, crystalline states, and other states, or forms, that can vary over time). This method is well suited for such measurements since individual Raman spectra can be collected rapidly (e.g., in a few seconds). Preferably, the turn-around time for generating a spectrum and assigning the spectrum to a bin is less than about two minutes, one minute, ten seconds, or one second. Moreover, limited real time processing is often possible if an acquired spectrum is to be assigned to existing bins, or, in a preferred embodiment of the invention, a library of binned spectra is updated with newly acquired spectra. In a preferred embodiment, newly acquired spectra from a single sample may all be binned into a single bin based on a majority of them being more related to the single bin in accordance with a metric, such as those discussed below and elsewhere herein.

Once the spectra from all of the samples to be analyzed have been collected, they are processed by a series of algorithms. These algorithms facilitate the binning of sample spectra according to one or more spectral features. Examples of such features include, but are not limited to, the locations of peaks, peak shoulders, peak heights, and peak areas. In a preferred embodiment, the spectral binning process bins spectra based on the locations of their scattering peaks and peak shoulders, expressed as wavelength or Raman shift ($cm^{-1}$).

In the spectra binning system, the collected spectra can be binned using the raw or filtered spectra, peak height spectra generated using peaks selected from the raw or filtered spectra, and binary spectra generated using the raw or filtered spectra.

Figure 15:
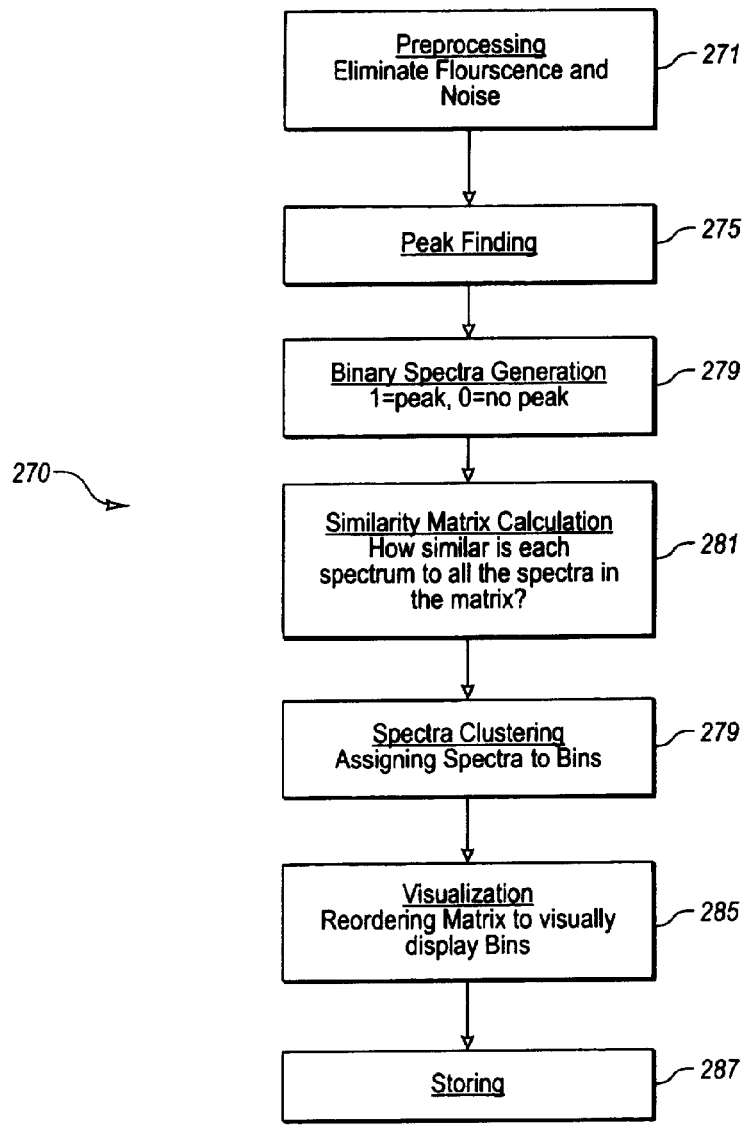
FIG. 15 is a flowchart depicting six stages of a computational binning process of one embodiment of the invention, and one optional stage in such a process.

FIG. 15 represents the computational process applied by a specific embodiment of the spectra binning system. As shown in the flow chart 270, the process can be divided into preprocessing 271, peak finding 275, similarity matrix calculation 281, spectral clustering 283, and visualization 285 stages An optional binary spectra generation stage 279 can also be used. Each of these stages, which are applicable to the analysis of data obtained using a variety of spectroscopic techniques. For the sake of convenience, however, each is discussed in more detail below in reference to Raman spectroscopy.

4.4.3.1. Preprocessing

In specific embodiments of the invention, preprocessing is used to eliminate artifacts of the Raman spectra that are not caused by Raman scattering. Preprocessing can also be used to make the Raman scattering peaks as sharp as possible. Raman spectra often contain large fluorescence peaks spread over a broad spectral range and much smaller, narrower peaks caused by scattering from containers (e.g., glass) and instrument noise. Several different filtering techniques can be used to eliminate such noise including, but not limited to, Fourier filtering, wavelet filtering, matched filtering, and averaging. A preferred method uses a matched filter approach, wherein the filter kernel is a zero-mean, symmetric product of sinusoids matched approximately to an average Raman peak width. The specific form of the matched filter is given by the following equation:

$$k[n] = \sin\left(\frac{3\pi n}{N-1}\right) \cdot \sin\left(\frac{\pi n}{N-1}\right)$$

where N is the length of the kernel. Preferably, the matched filter equation includes a normalization term:

$$k[n] = -\sqrt{\frac{4}{N-1}} \sin\left(\frac{3\pi n}{N-1}\right) \cdot \sin\left(\frac{\pi n}{N-1}\right)$$

The normalization factor ensures that the magnitude of the "passed" peaks in a filtered signal are about the same as the magnitude of the original peaks, and that all peaks point in the right direction. In one embodiment, filtered points having a value less than zero are automatically set to equal zero.

In a specific embodiment of the invention, the bandwidth of the main kernel peak is set to be equal to or slightly smaller than the bandwidth of an average Raman peak. When matched filters of this type are viewed in the Fourier domain, they perform as bandpass filters, almost completely attenuating low and high frequency spectral components. Furthermore, with the bandwidth of the filter kernel chosen to be equal to or slightly smaller than the average Raman peak bandwidth, this filter detects peaks that are very close to each other. A raw, unfiltered spectrum will often display two close peaks as a main peak with a "shoulder" on one of its sides. After a matched filtering step, though, the shoulder will often be distinguished as a separate peak. This separation is useful for the selection, or finding, of peaks used for binning.

Figure 16A:
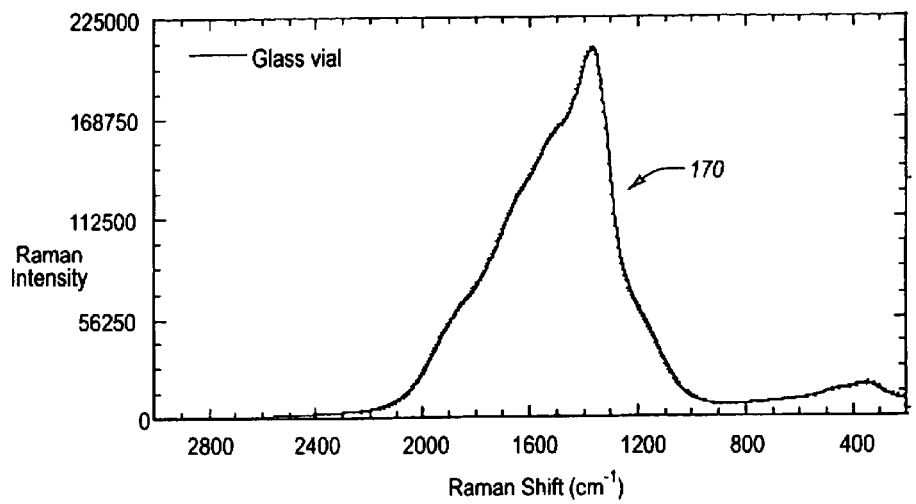
FIG. 16A is a graph showing Raman intensity plotted as a function of Raman shift ($cm^{-1}$) for an empty glass vial.
Figure 16B:
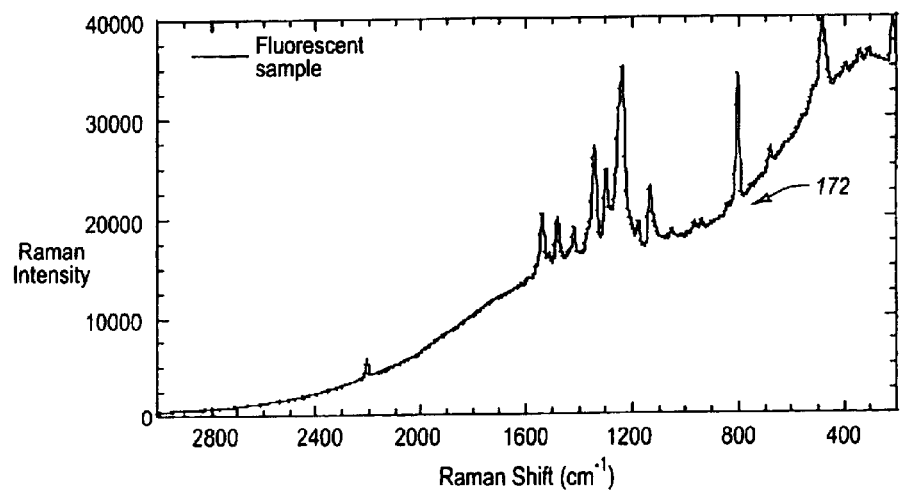
FIG. 16B is a graph showing Raman intensity plotted as a function of Raman shift ($cm^{-1}$) for a fluorescent sample.
Figure 16C:
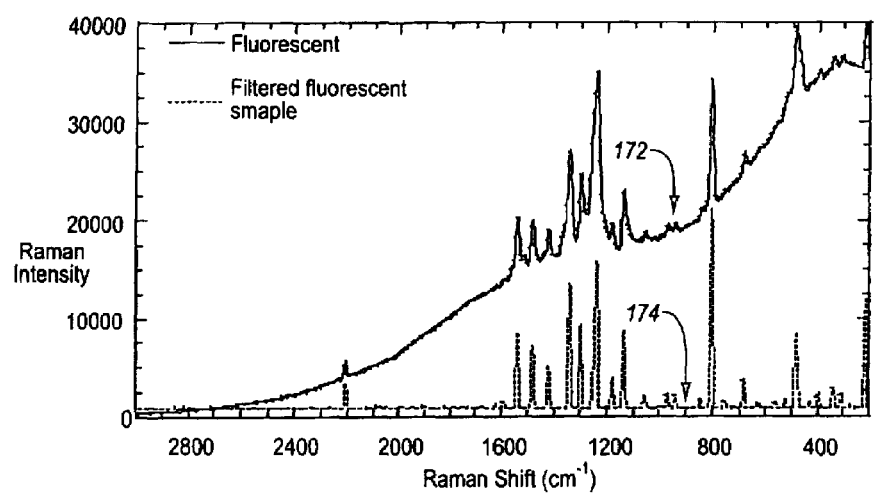
FIG. 16C is comparative graph showing Raman intensity plotted as a function of Raman shift ($cm^{-1}$) for the pre-filtered sample of FIG. 17B compared to the corresponding filtered spectra after the fluorescence has been removed.

An example of the effect of such filtering means is provided in FIG. 16. Specifically, FIG. 16A shows Raman intensity plotted as a function of Raman shift (cm$^{-1}$) for an empty glass vial. The resulting waveform shows the pattern of absorbance present. FIG. 16B shows a Raman intensity of a fluorescent sample as a function of Raman shift. FIG. 16C shows the same pre-filtered plot as that of FIG. 16B, but also shows the corresponding filtered spectra after the fluorescence has been removed.

4.4.3.2. Peak Finding

The process of finding peaks in a spectrum is an essential aspect of many spectral processing techniques, so there are many commercially available programs for performing this task. The many variations of peak finding algorithms can be found in the literature. An example of a simple algorithm is to find the zero-crossings of the first derivative of a smoothed or unsmoothed spectrum, and then to select the concave down zero-crossings that meets certain height and separation criteria. In a specific embodiment, the peak finding function available in the software provided with the Almega dispersive Raman spectrometer (Thermo Nicolet, OMNIC software) is used. This function allows the threshold and sensitivity values to be set by the user. The threshold sets the lowest peak height that will be counted as a peak, and the sensitivity controls how far apart each peak must be to count as a separate peak.

In an optional step, once the peaks have been found for all of the spectra, binary spectral representations are created for all of the initial spectra. These binary spectra are essentially vectors of ones and zeros. Each zero represents the absence of a peak feature and each one represents the presence of a peak feature. A peak feature is simply a peak that occurs within a certain spectral range, usually a few wave numbers. The vectors for all of the spectra are the same length and corresponding elements of these vectors correspond to peak features occurring at nearly the same locations in the spectra.

In order to create these binary spectra, peaks are clustered into ranges of peak features. The process used to perform this peak clustering is a modified form of a 1-dimensional iterative k-means clustering algorithm. The process begins with the peaks picked from a single spectrum. These peak positions are used to define the centers of the spectral bins, peak feature bins, for the creation of the binary spectra. A spectral bins cover a range of wave numbers that may be specified by the operator (in one embodiment, the default is five wave numbers). The rest of the spectra are then iteratively added to the peak feature representation. At each step, any peak that fits into a pre-existing peak feature bin is added to that bin. For any peak that does not fit into a bin, a new bin is created. The centers of the bins are not permitted to move resulting in overlapping peak feature ranges. Then, the centers of all of the ranges are re-calculated, optionally with a modified range of wave numbers, and the peak feature bins are re-defined relative to the new centers. This process can leave some peaks outside of an existing peak feature range. In this case, a new range is created for these peaks. This process creates a matrix with each row of the matrix corresponding to a binary spectrum specified in terms of the bins in which its peaks fall. An example of such a matrix for five spectra is given below in TABLE 1.

TABLE 1

| | Peak Position | | | | |
|---|---|---|---|---|---|
| | 270 | 350 | 390 | 430 | 510 |
| Spectrum 1 | 1 | 1 | 0 | 1 | 1 |
| Spectrum 2 | 1 | 0 | 0 | 1 | 1 |
| Spectrum 3 | 1 | 1 | 0 | 0 | 0 |
| Spectrum 4 | 0 | 1 | 1 | 1 | 0 |
| Spectrum 5 | 1 | 1 | 0 | 1 | 1 |

In this matrix, Spectrum 1, for example, has a peak in each of the bins corresponding to wave numbers 270, 350, 430 and 510, but does not have a peak in the bin associated with wave number 390. This optional step of binary spectra generation has several benefits over "spectrum to spectrum" or peak height spectra comparisons, which include, but are not limited to, yielding data on differences between spectra that is useful in refining spectra collection and peak-finding algorithms, and reducing or removing orientation-dependent peak amplitudes from the spectra.

From either the spectra themselves, the peak height spectra, or from binary spectra such as those generated using the process described above, similarity between all of the spectra in the matrix can be calculated. This similarity measure is utilized to identify and create cluster boundaries. Illustrative, but not limiting, similarity measures include Hamming or Euclidean distance, or non-metric similarity indices such a the Tversky similarity index (or its derivatives such as the Tanimoto or Dice coefficients) or functions thereof.

In order to describe a spectra-to-spectra similarity matrix, the following notation can used: $N_{mn}$=number of peak values in a first spectrum falling in the same peak feature bin in a second spectrum; $N_m$=number of peak values in the first spectrum; and $N_n$=number of peak values in the second spectrum. Similarity can then be calculated using various methods, e.g., $$\text{Tanimoto}(m, n) = \frac{N_{mn}}{N_m + N_n - N_{mn}}$$

Figure 17A:
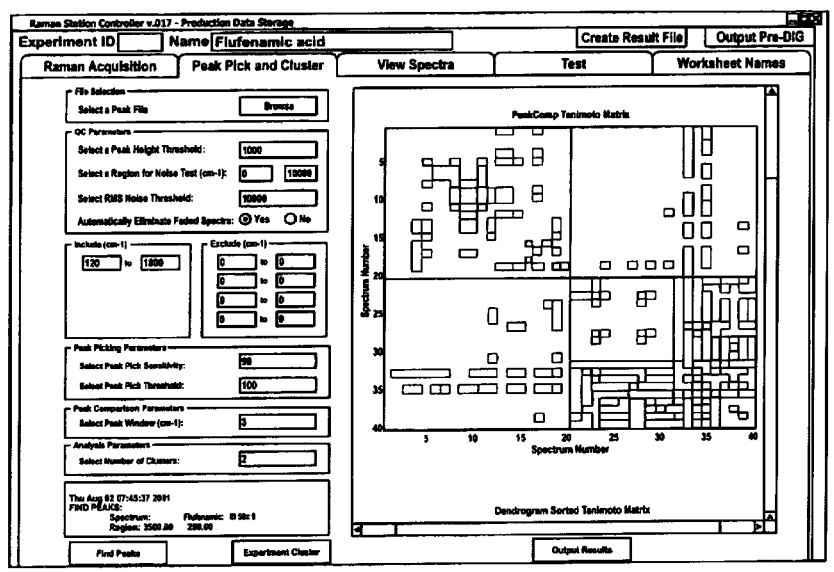
FIG. 17A is a screen shot showing the output from the binning software captured during the binning procedure for the flufenamic acid sample set.
Figure 17B:
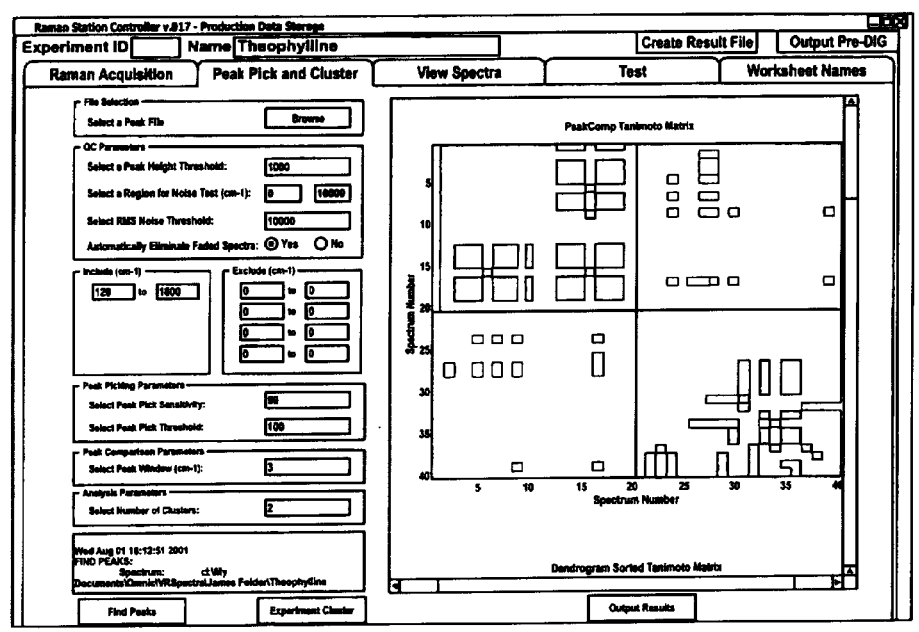
FIG. 17B is a screen shot showing the output from the binning software captured during the binning procedure for the theophylline sample set.

The matrices shown in FIGS. 17A and 17B were generated using this foregoing method.

For similarity matrices based on binary spectra, the following notation can be used: a=number of 1's in a first spectrum that are zeros in a second spectrum; b=number of 1s in a second spectrum that are zeros in the first spectrum; and c=number of 1s in the first spectrum that are ones in the second spectrum. These values can be calculated in the following manners:

| Hamming distance: | $d = a + b$ |
|---|---|
| Euclidean distance: | $d = \sqrt{a+b}$ |
| Tversky index: | $t = \dfrac{c}{\alpha a + \beta b + c}$ |

Some of these metrics are related. For instance, the Tanimoto coefficient is equal to the Tversky index with α and β equal to 1. The Dice coefficient is equal to the Tversky index with α and β equal to 0.5. In a preferred embodiment, 1—Tanimoto coefficient is used as the (dis)similarity measure. It should be noted that additional metrics, including metrics based on other metrics, may be used in alternative embodiments of the invention.

Once a particular way of measuring the similarity of sample spectra has been selected, the similarity of the spectra is determined. This determination typically results in a symmetric similarity matrix with each element (i,j) of the matrix representing the similarity between spectra i and j.

Using the similarity matrix or the binary spectra matrix, several different clustering methods can be employed to assign spectra into bins. Hierarchical clustering, k-means clustering, Gaussian mixture model clustering, and self-organizing map (SOM) based clustering are just some of the methods that can be used. These and other methods are well described in the literature. See Kohonen, T., "Self-organizing Maps", Springer Series in Information Sciences, Vol. 30, Springer, Berlin, Heidelberg, New York, $3^{rd}$ Extended Edition (2001); Duda, R., Hart, P., and Stork, D., "Pattern Classification", John Wiley & Sons, $2^{nd}$ Edition (November 2000); and Kaufman, L., Rowseeaww, "Finding Groups in Data", John Wiley & Sons, (1990). In a preferred embodiment, hierarchical clustering is used as a first-pass method of data analysis.

Using the information from the hierarchical clustering run, k-means clustering is then performed with user-defined cluster numbers and initial centroid positions. In another embodiment, the number of clusters can be automatically selected in order to minimize some metric, such as the sum-of-squared error or the trace or determinant of the within cluster scatter matrix. See Duda, R., Hart, P., and Stork, D., "Pattern Classification", John Wiley & Sons, $2^{nd}$ Edition (November 2000).

Hierarchical clustering produces a dendrogram-sorted list of spectra, so that similar spectra are very close to each other. This dendrogram-sorted list can be used to present the similarity matrix in a coded manner, wherein similarity indicia are used for each similarity region, including without limitation different symbols (such as cross-hatching), shades of color, or different colors. In a specific embodiment, the coded similarity matrix is presented in a color-coded manner, with regions of high similarity in hot colors and regions of low similarity in cool colors. Using such a visualization, many clusters become apparent as hot-colored square regions of similarity along the matrix diagonal. These square regions represent the high degree of similarity between all of the spectral (i,j) pairs in those regions. However, it should be noted that the failure of the coded similarity matrix to present a diagonal form is to be expected with some types of samples, although the matrix is still useful in representing more complex similarity relationships. Furthermore, in some cases there can be similarity regions along more than one possible diagonal that correspond to different rearrangements. Such rearrangements result in off-diagonal similarity square regions becoming part of the diagonal similarity square regions.

Along with the matrix representation of the cluster data, it is also useful to show where all of the spectra and the cluster boundaries lie in a dimensionally reduced space (usually 2-dimensions). There are several ways to perform this dimensionality reduction. In a preferred embodiment, a linear projection is made of a binary spectra matrix onto its first two principal components. Alternatively, the chosen similarity matrix could be used in order to create a map of the data using multidimensional scaling.

Figure 18:
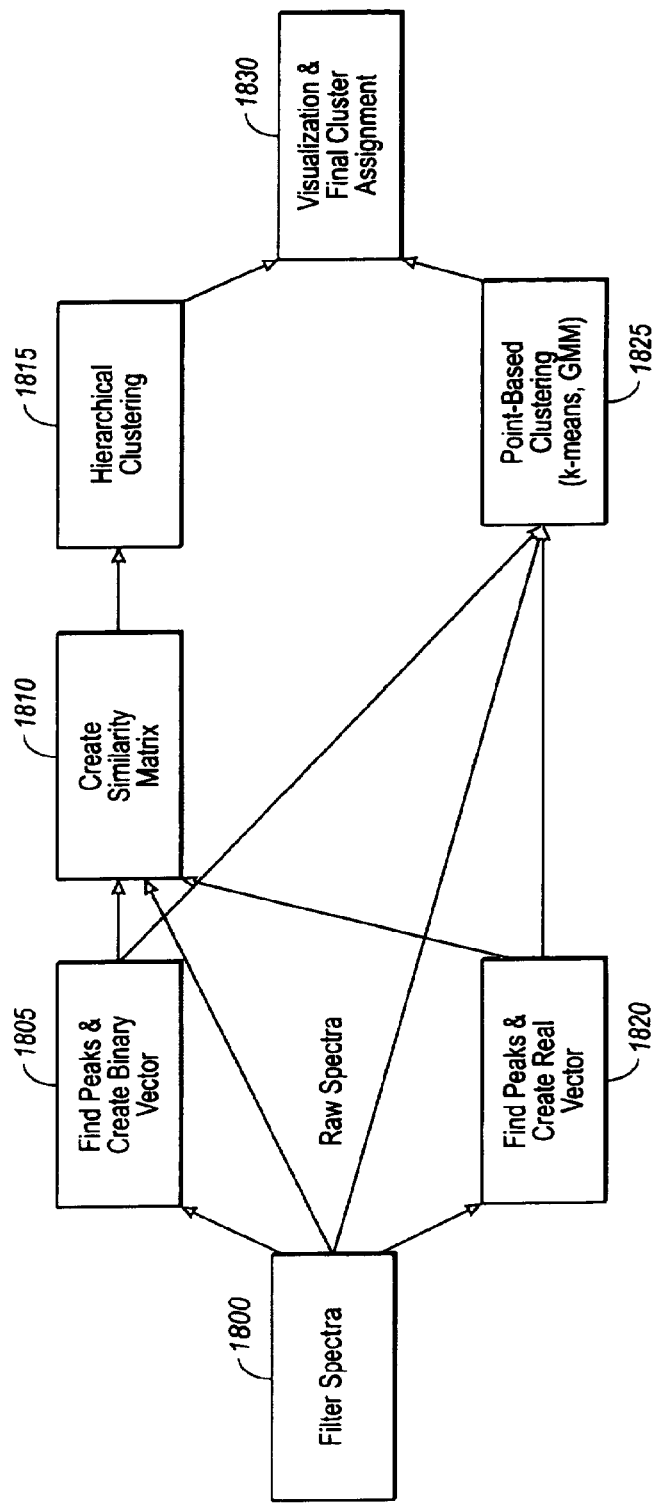
FIG. 18 illustrates an implementation of the binning procedure.

FIG. 18 illustrates an implementation of the binning procedure. At step 1800 the filter spectra are obtained. In one branch of the possible procedure, the peaks are located and corresponding binary spectra constructed in step 1805. The binary spectra are used to create the similarity matrix during step 1810. Next, hierarchical clustering results from sorting the similarity matrix to place similar spectra close to each other during step 1815. This matrix is suitable for visualization during step 1830. In one of the many alternative ways of processing the raw spectra of step 1800, the peaks are located and instead of binary vectors of step 2405, peak height vectors are generated during step 1820. Control can flow to step 1810 for the construction of a similarity matrix or directly point based clustering may be performed during step 1825 followed by visualization of the results in step 1830. Other alternative embodiments include control flowing from step 1805 following generation of binary vectors to point based clustering in step 1825 and then onto visualization in step 1830.

An example Raman binning application is written in Visual Basic (VB). This VB program allows a user to select a group of spectra and set processing parameters. Preprocessing is performed within the VB application and then the filtered spectra are sent to OMNIC for peak finding through the Macros/Pro DDE communication layer provided by OMNIC. Once peaks are found, binary spectrum and distance matrix generation is performed in the main VB application. Then, the distance matrix is sent to MATLAB through a socket communication layer. Using a program such as MATLAB, clusters are generated and visualizations are created. These visualizations are made available to the main VB application through a web server. The resulting visualization allows for the easy identification of groups of samples that all have similar physical structure.

5. EXAMPLES

Some specific, non-limiting examples of particular features of the invention are provided below.

5.1. Example 1

Raman Data Acquisition System

An automated robotic mechanism has been constructed and integrated with a microscope to facilitate selecting the sample containers (e.g., tubes) from the blocks and positioning the containers under the microscope objective for spectral acquisition. The spectral data collection system comprises a dispersive Raman microscope (Almega dispersive Raman by Thermo Nicolet, 5225 Verona Road, Madison, Wis. 53711, USA), which is a research grade dispersive Raman instrument, combining a confocal Raman microscope and a versatile macro sampling Raman spectrometer. The highly automatable and versatile system offers multiple laser options under software automation, for optimized sensitivity, spatial resolution, and confocal operation. The Almega dispersive Raman spectrometer is capable of housing up to two lasers. Selection of the lasers and control of laser power is accomplished through software. In addition, the appropriate Rayleigh rejection filters, apertures and gratings are automatically selected when the laser excitation wavelength is changed. The high-resolution setting provides better than 2 cm$^{-1}$ resolution for all laser wavelengths. The spectral range of operation for CCD based detection is 400–1050 nm, allowing collection of Raman spectra over the full range for laser wavelengths. The example system is equipped with a 785 nm laser, a 256 k×1024 k CCD detector, and a NTSC video camera to monitor samples in the microscope with a spectral range, when using the 785 nm laser, of 100–3200 cm$^{-1}$.

Figure 13A:
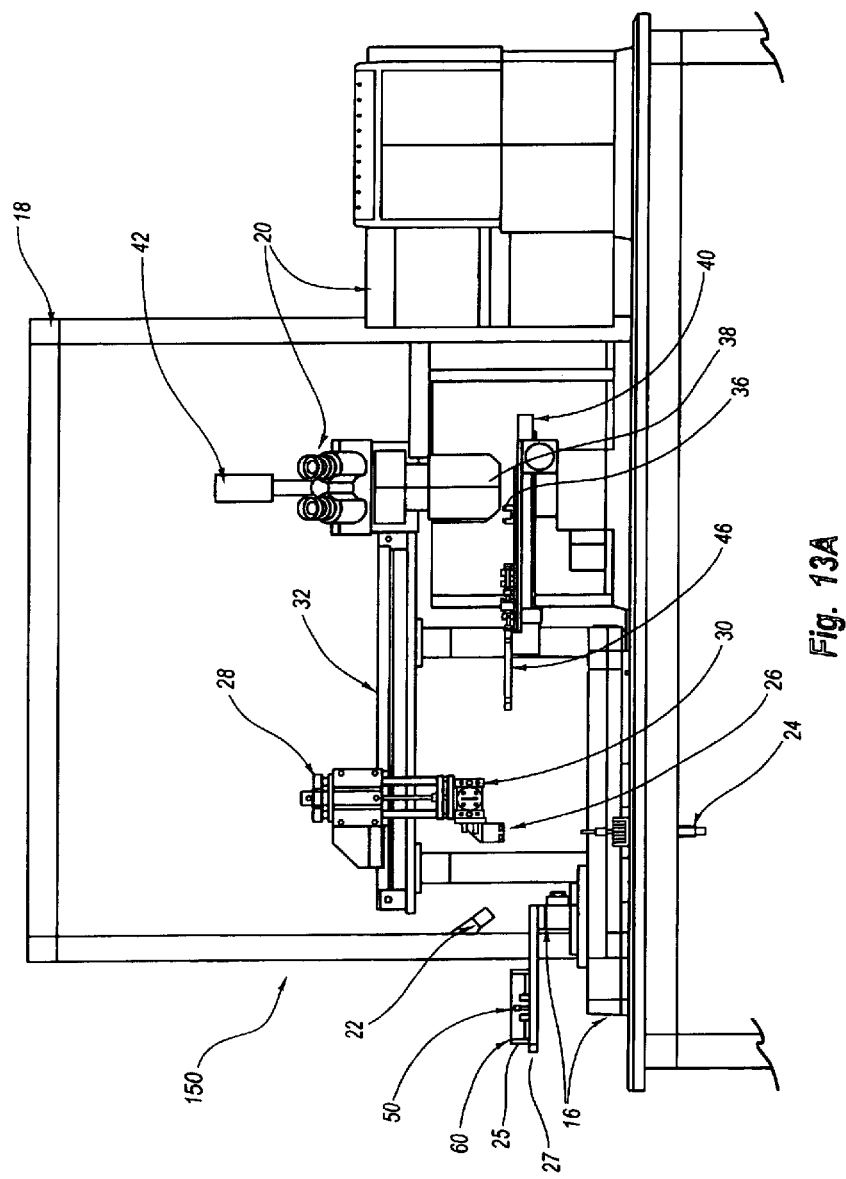
FIG. 13A is a perspective diagram of the Raman system.
Figure 13B:
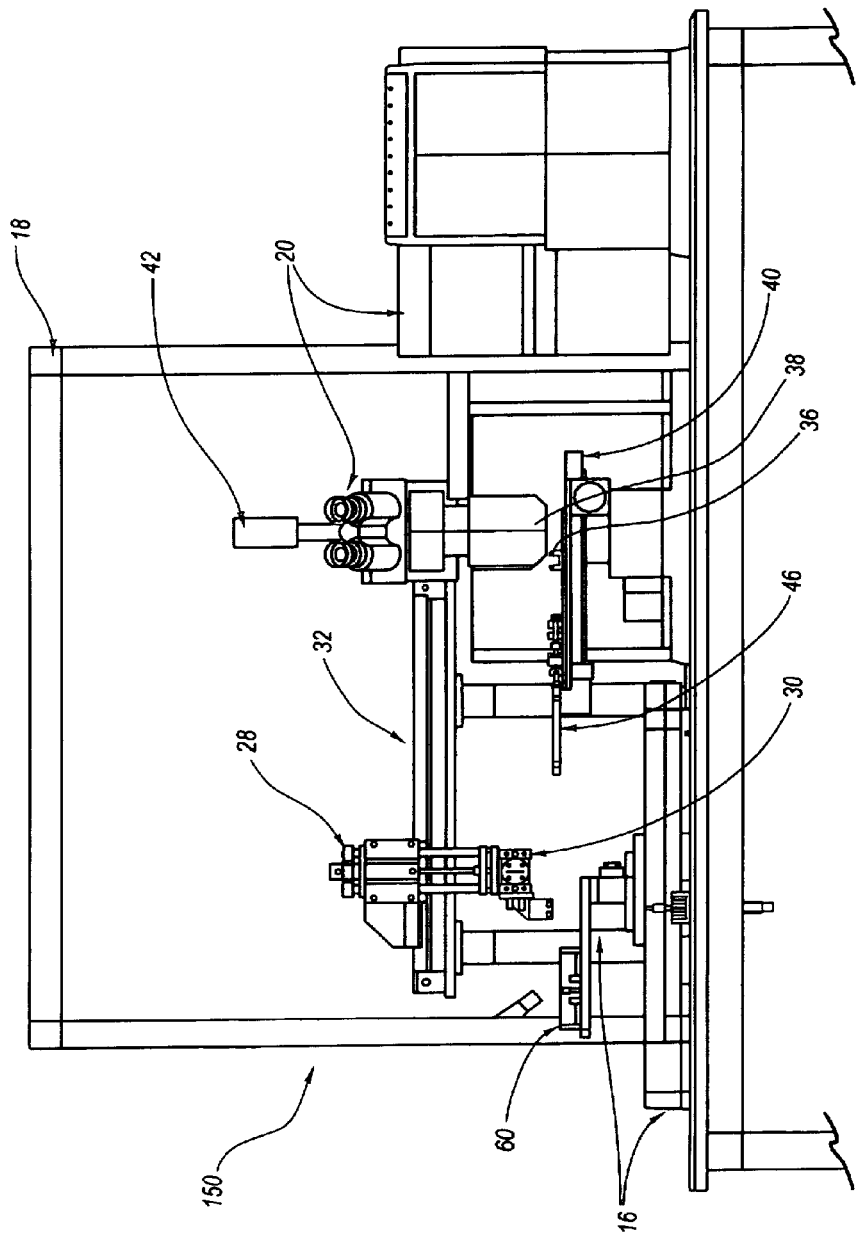
FIG. 13B is a diagram showing a block of tubes being moved inside an enclosure.
Figure 13C:
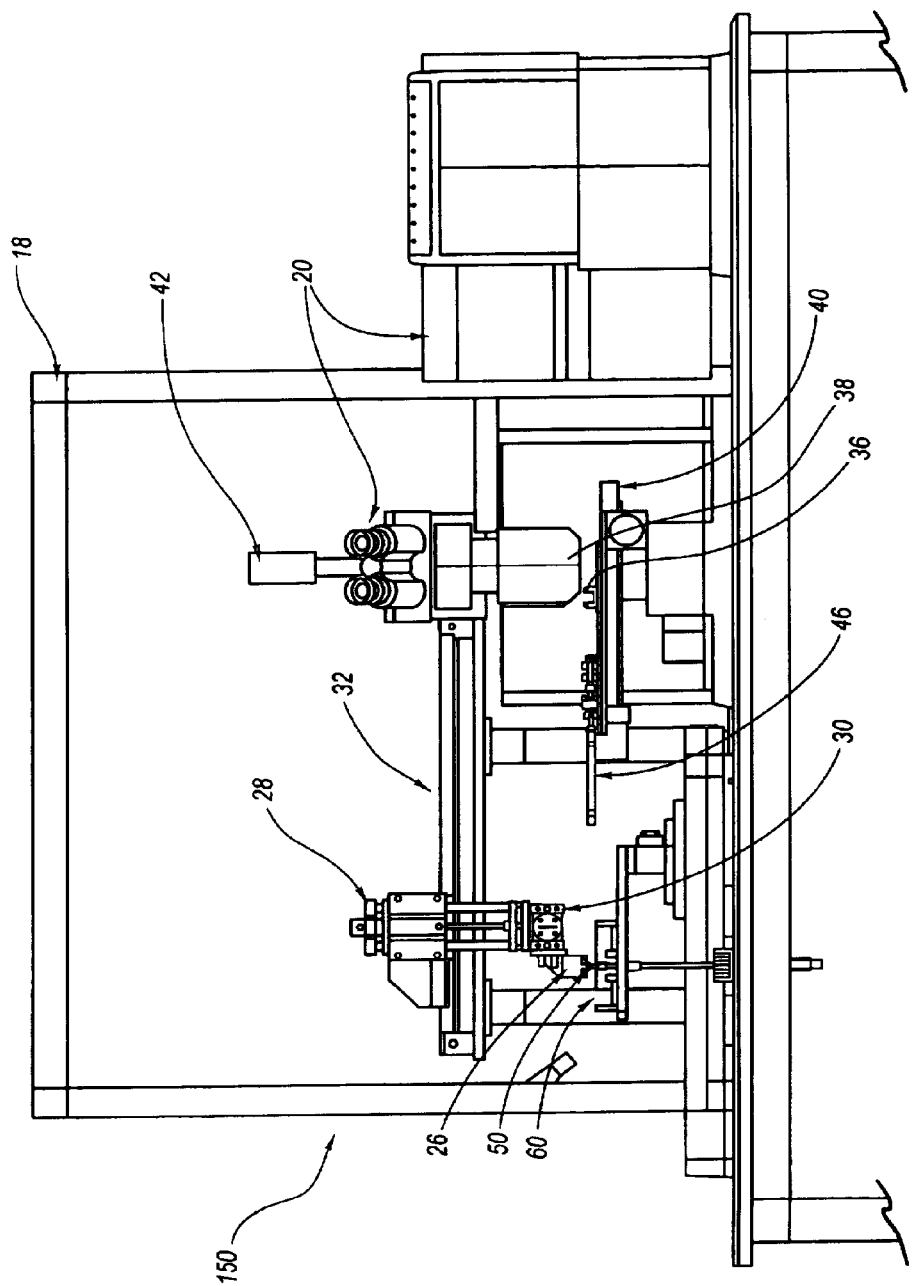
FIG. 13C is a diagram showing the lifting mechanism elevating a tube to be gripped by the tube gripper.
Figure 13D:
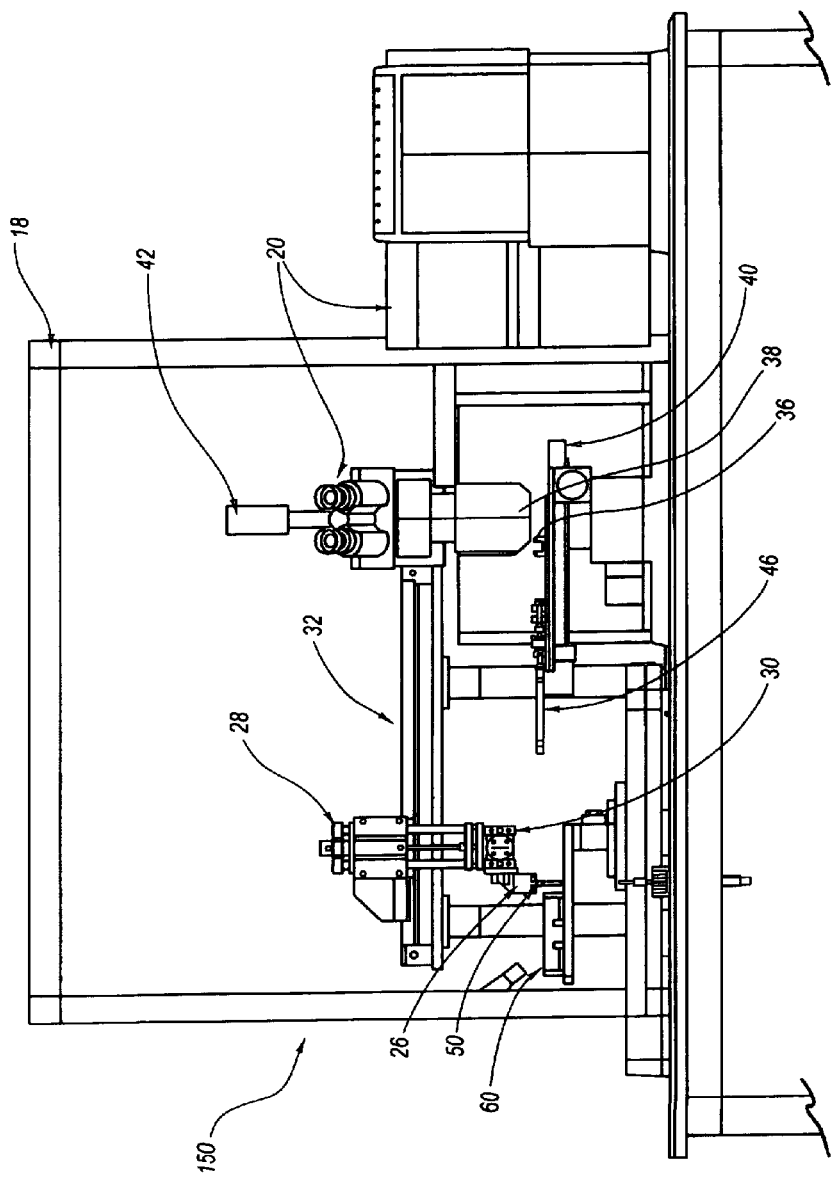
FIG. 13D is a diagram showing the tube gripper and tube having moved in the vertical direction.
Figure 13E:
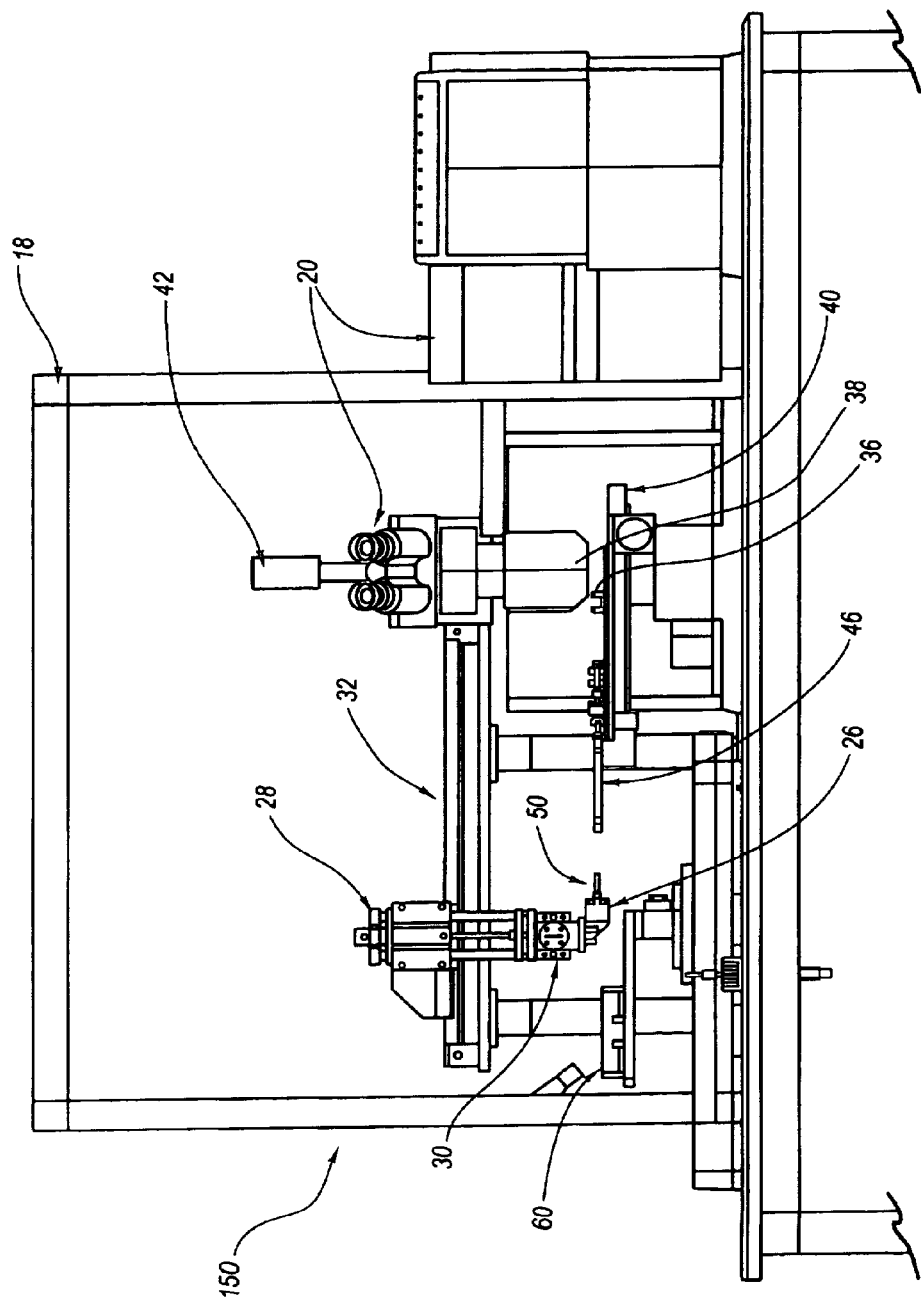
FIG. 13E is a diagram showing the tube gripper and tube having rotated.
Figure 13F:
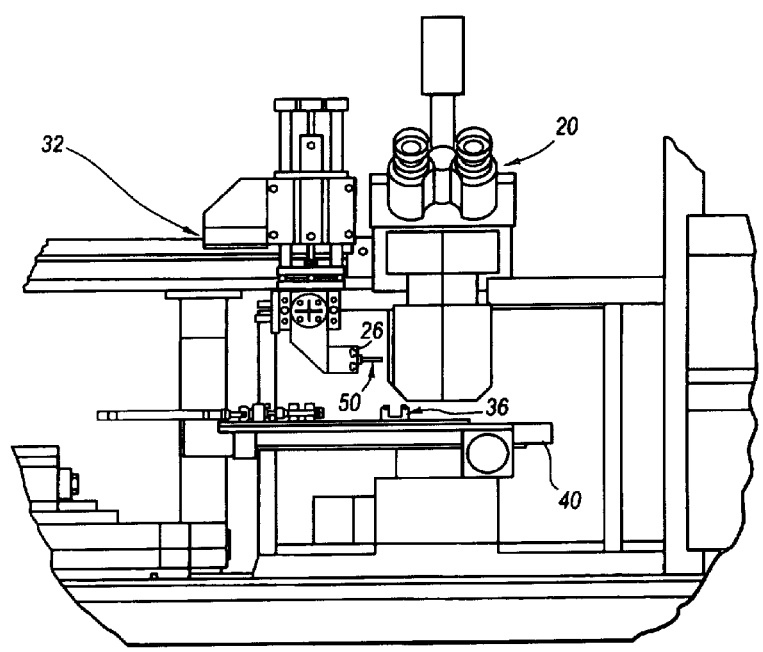
FIG. 13F is an enlarged diagram showing the tube gripper and tube having moved in the horizontal direction to bring the tube closer to the microscope objective.
Figure 13G:
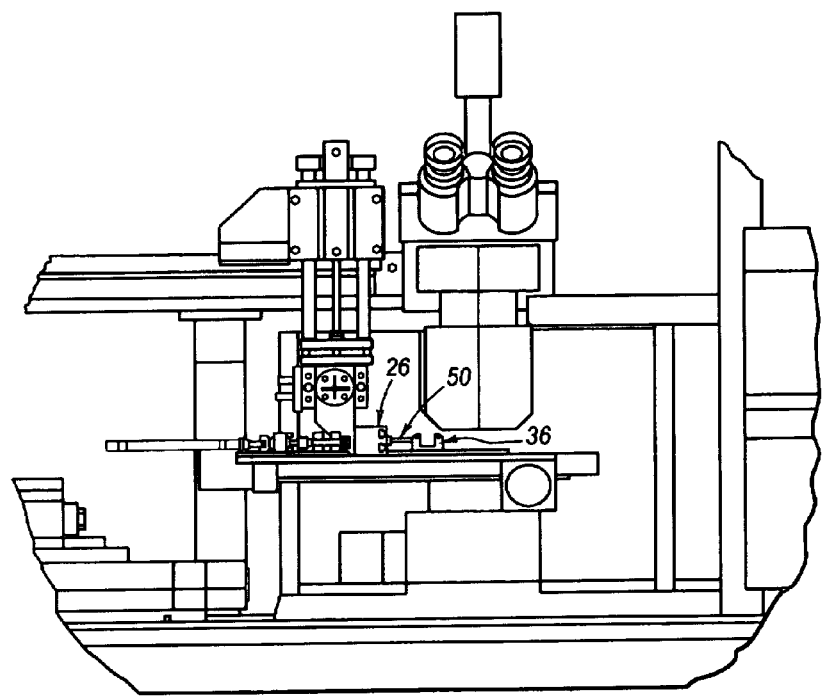
FIG. 13G is an enlarged diagram showing the tube gripper and tube having been lowered to a position near the tube holder.
Figure 13H:
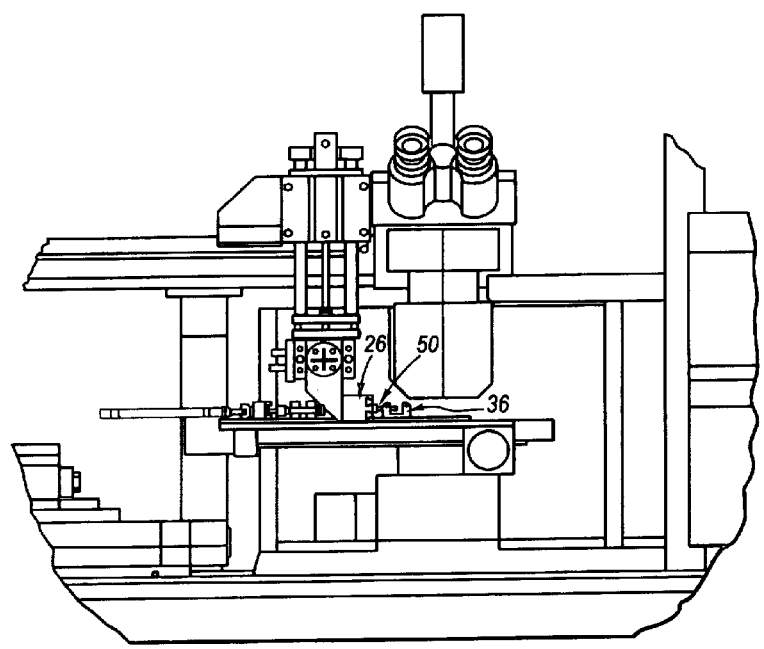
FIG. 13H is an enlarged diagram showing the tube gripper having loaded the tube into the tube holder.
Figure 13L:
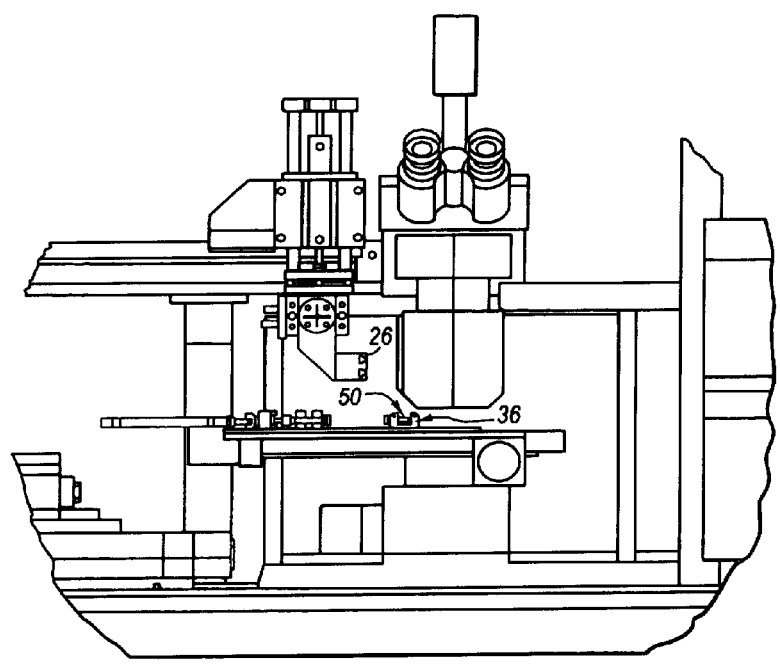
FIG. 13I is an enlarged diagram showing the tube gripper having retracted after loading the tube into the tube holder.
FIG. 13J is an enlarged diagram showing a tube rotator engaging the tube.
FIG. 13K is an enlarged diagram showing the tube being moved under the microscope objective.
Figure 13J:
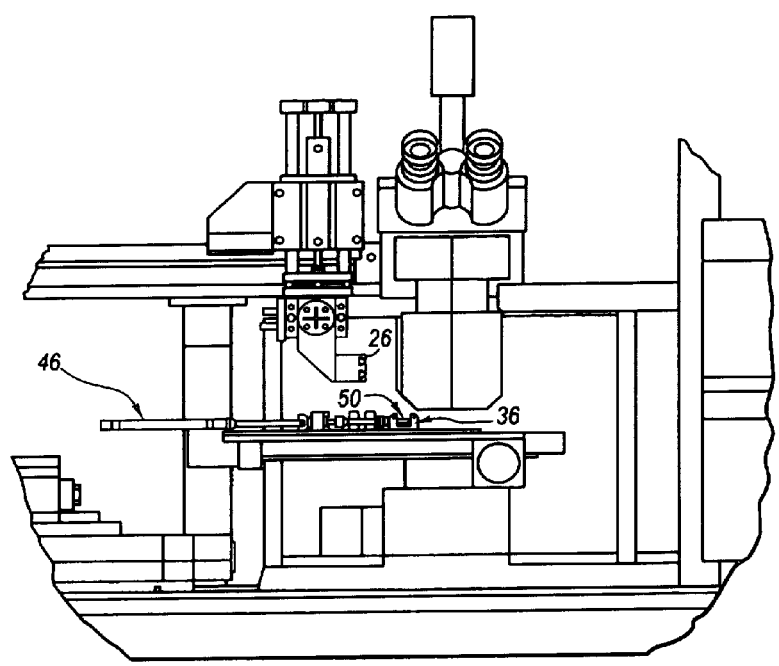
Figure 13K:
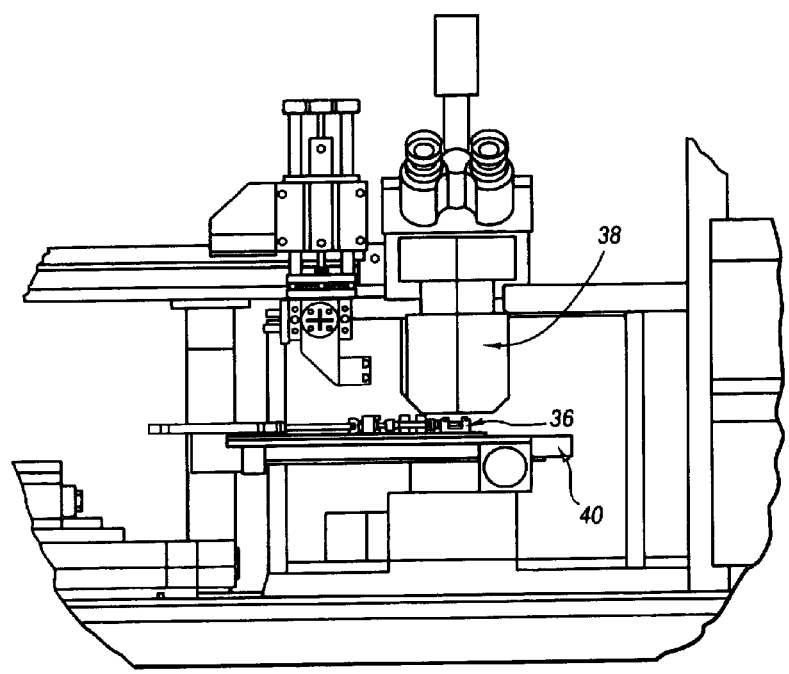

FIG. 13A shows a schematic of an entire automated spectra collection in Raman system 150. Material handling automation has been designed around the microscope to allow automated sample handling in and out of Raman system 150. Operationally, block 60 containing samples, in tubes 50, is placed into block nest 25. Block nest 25 is attached to XY stage 27 (Parker) to allow individual addressing of tubes within the block. XY stage 27 is attached to linear actuator 16 (Parker) that moves in the X direction. When block 60 is placed in block nest 25, a sensor (commercially available from Keyence) is activated, causing linear actuator 16 to move block 60 into light-tight enclosure 18 surrounding the Raman microscope, shown in FIG. 13B. Once inside enclosure 18, bar code reader 22 (commercially available from Keyence) reads the bar code on the sample block in order to track the contents of block 60. Referring to FIG. 13C, lift mechanism 24 presents individual tube 50 to tube gripper 26 by pushing tube 50 up through the access hole in the bottom of block 60. In FIG. 13D, tube gripper 26 and tube 50 are raised vertically from block 60. Tube gripper 26 is attached to linear actuator 32 and rotary actuator 30. FIG. 13E shows rotary actuator 30 rotating 90 degrees counter-clockwise to position tube 50 in a horizontal direction. Tube gripper 26 is then ready to travel horizontally along linear actuator 32 to move tube 50 near tube holder 36 in input stage 40 of microscope 20 as shown in FIG. 13F. FIG. 13G shows tube gripper 26 lowering tube 50 to tube holder 36. Tube 50 is then placed in tube holder 36, as shown in FIG. 13H, and tube gripper 26 is retracted vertically, as shown in FIG. 13I. Tube rotator 46 then engages tube 50 in tube holder 36, shown in FIG. 13J. Finally, in FIG. 13K, microscope input stage 40, under computer control, then actuates tube holder 36 under objective 38 for Raman analysis.

FIGS. 14A–G shows a procedure for focusing the Raman spectrometer on a solid form inside tube 50. The solid form is typically found attached to an inside surface of the tube. Therefore, the Raman spectrometer is preset to first look at that position and depth. This focusing also reduces the noise due to out of focus fluorescent emissions. Although confocal techniques are not used in this example implementation, in alternative embodiments of the invention they provide greater reduction in the noise since only the radiation through a pinhole is used at any time with integration over time to reconstruct the entire image. Naturally, data collection is over longer periods of time.

Figure 14A:
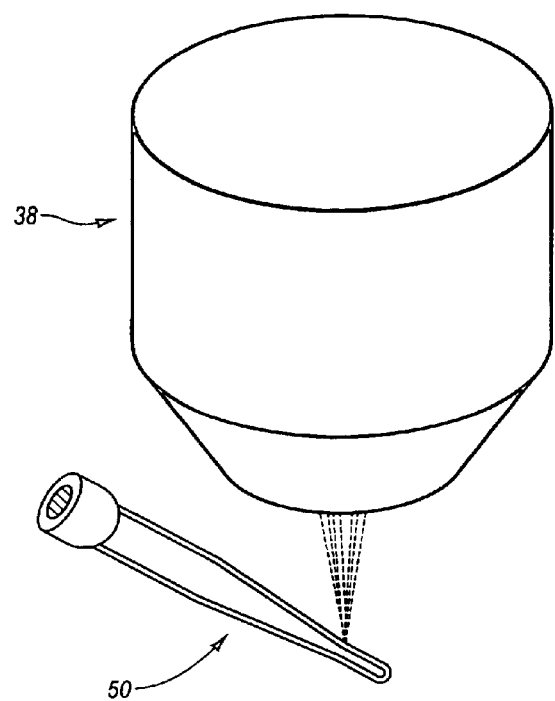
FIG. 14A is a perspective view of a tube and microscope objective. The long axis of the tube is preferably at a 90 degree angle to the axis of the objective.
Figure 14B:
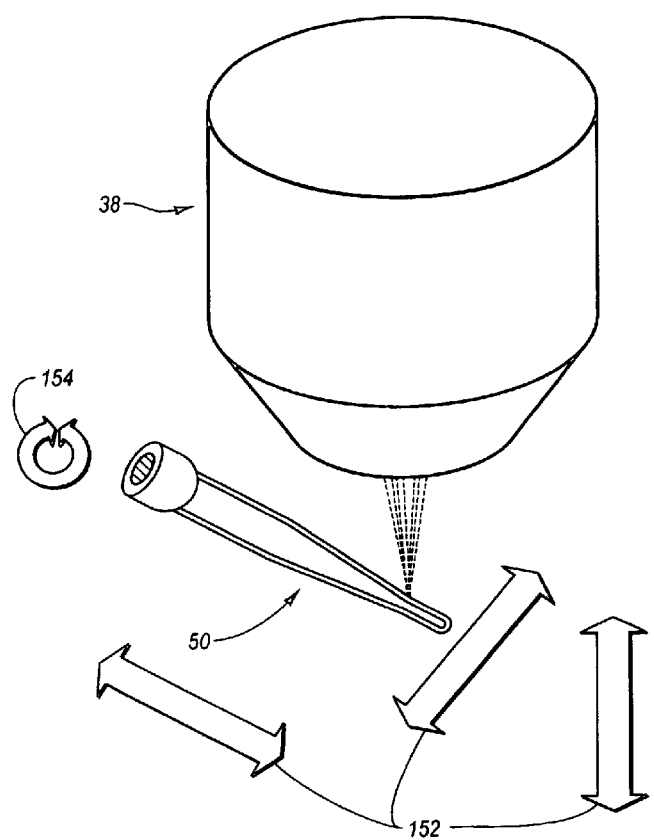
FIG. 14B is diagram of a tube and microscope objective indicating the available axes of motion for the tube.

Returning to the described embodiment, it becomes necessary to properly position the tube beneath objective 38 of the microscope so that the solid form is at the right depth. As shown in FIG. 14B, this is accomplished by moving the entire microscope stage (not shown) supporting the tube holder (tube holder 36, as shown in FIG. 14K) in the X, Y and Z directions, as indicated by arrows 152, as well as rotating tube 50, as shown by arrow 154, to present the solid form at the depth expected by the spectrometer. In a preferred embodiment, tube 50 has the geometry as shown in FIG. 2, where the top half of tube 50 is cylindrical, but the bottom half of tube 50 is tapered. If the solid form is located in the tapered portion of the tube, then moving the tube in the XY plane to position it under the objective will also result in changing the Z-height of the sample with respect to the spectrometer, thus the need for controlling the Z-height of the stage as well.

Figure 14C:
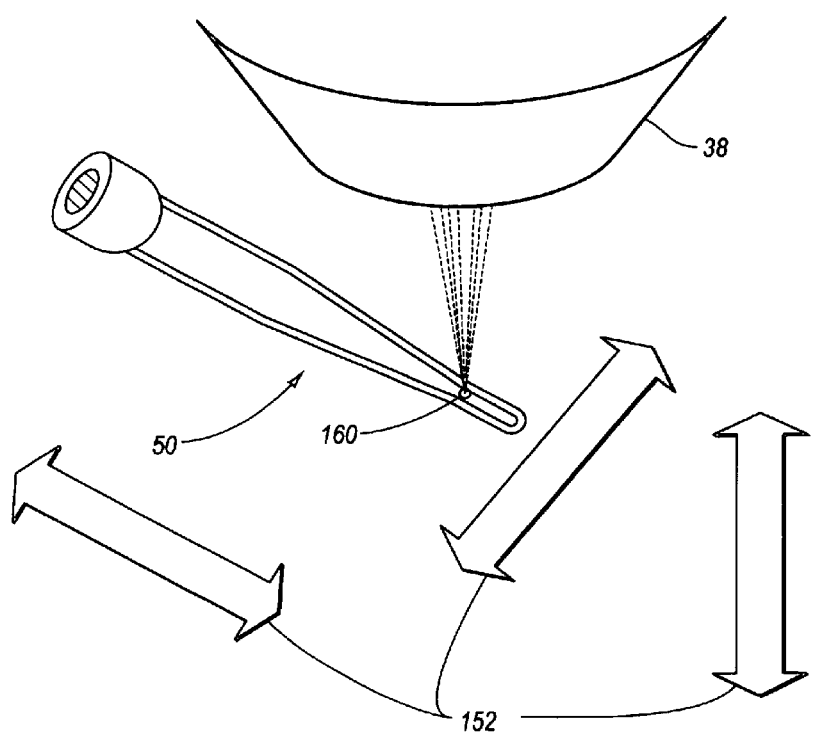
FIG. 14C is a closer view of a tube with a crystal inside that is in an out-of-focus position with respect to the microscope objective. This figure also indicates the available axes of motion for the tube.
Figure 14D:
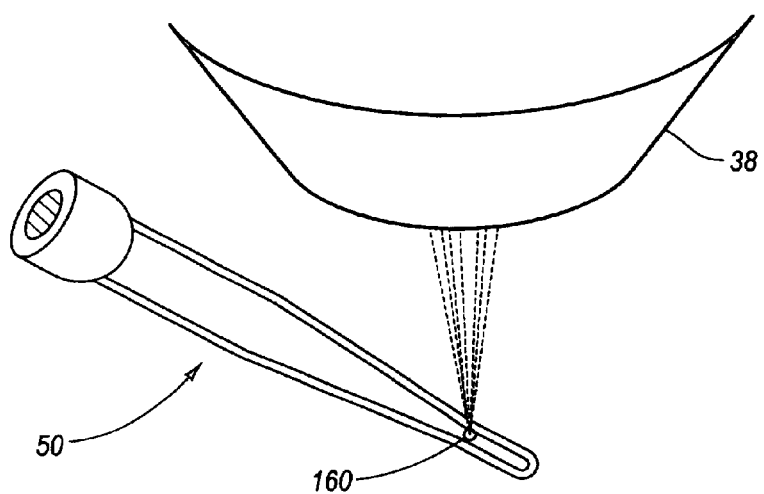
FIG. 14D is a detailed view of a tube with a solid, such as a crystal, inside that is located toward the narrow end of the tube and on the bottom surface with respect to the microscope objective.
Figure 14E:
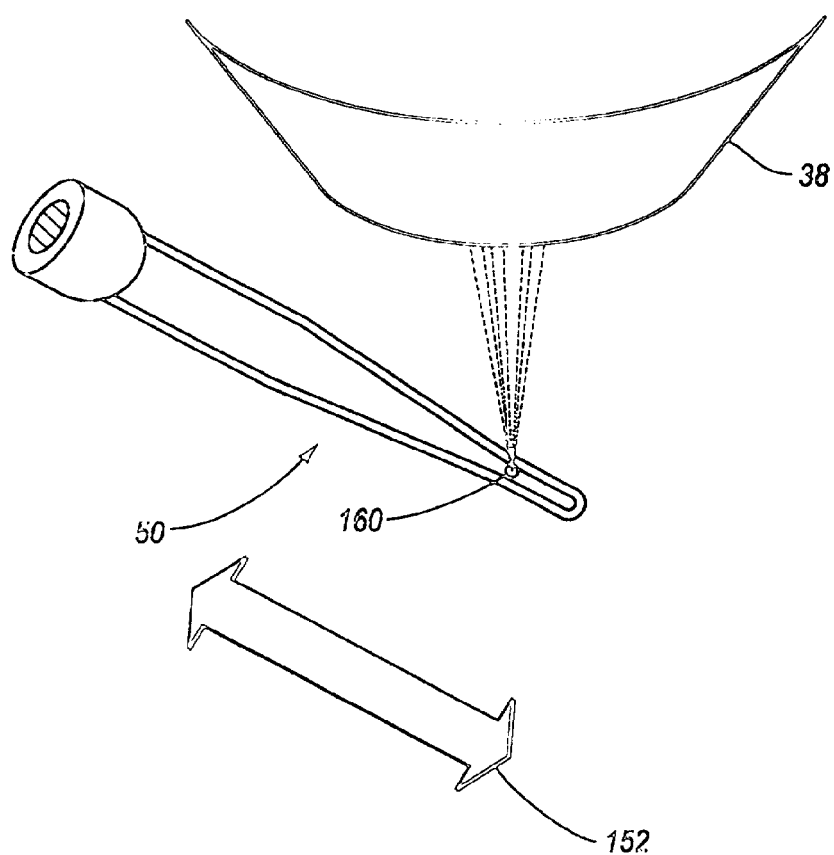
FIG. 14E is a detailed view of a tube with a solid, such as a crystal, inside that is being moved in the horizontal direction to bring it closer to the in-focus position beneath the microscope objective.
Figure 14F:
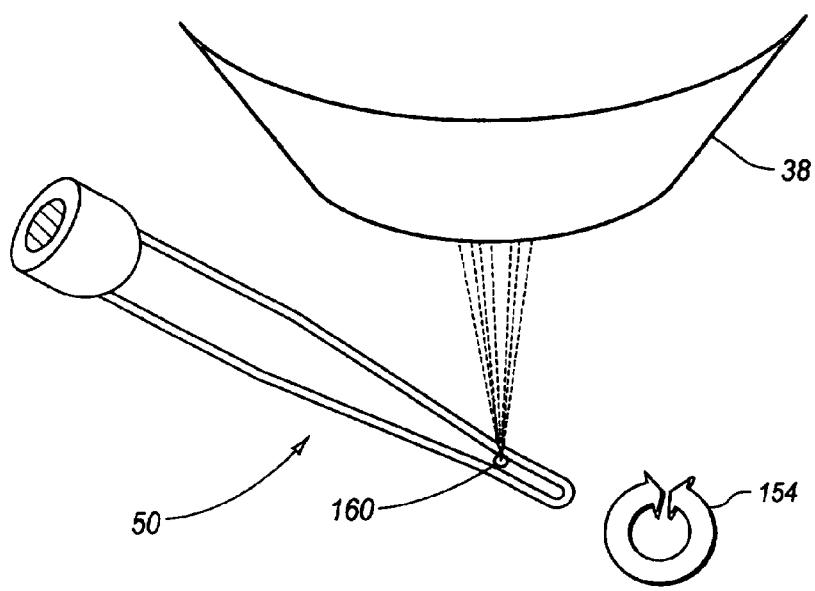
FIG. 14F is a detailed view of a tube with a solid, such as a crystal inside that is being rotated to bring it closer to the in-focus position beneath the microscope objective.
Figure 14G:
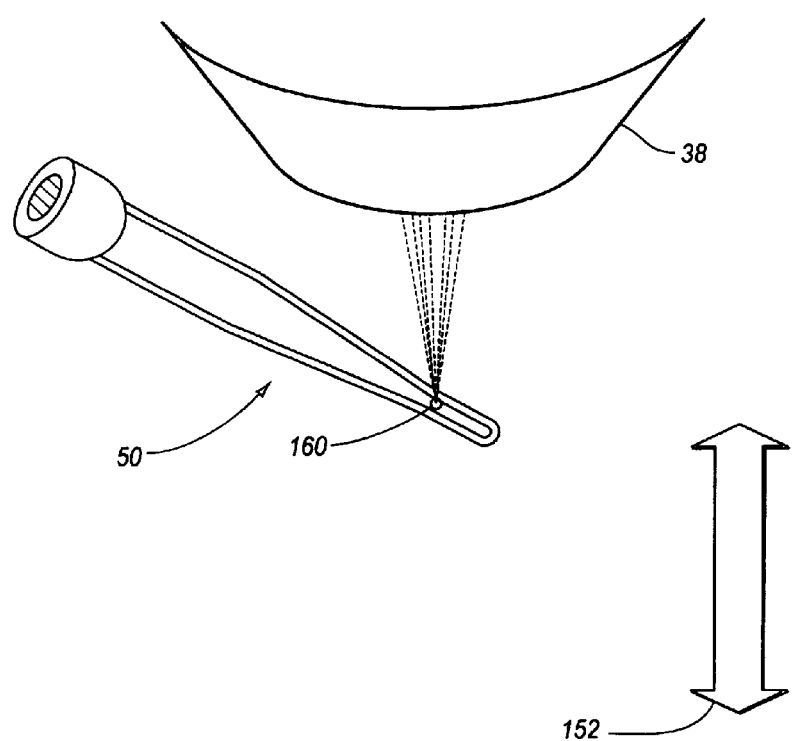
FIG. 14G is a detailed view of a tube with a solid, such as a crystal, inside that is being moved in the vertical direction to bring it to the in-focus position beneath the microscope objective.

FIG. 14C shows a detailed perspective view of solid 160 inside tube 50 in an out-of-focus position and indicates the available axes of motion 152 and 154. FIG. 14D shows a solid 160 that is out of focus because it is attached to the inside bottom (with respect to objective 38 located above) wall of tube 50 and is also located closer to the end of tube 50 than where the objective is focused. FIG. 14E shows how the microscope (not shown) stage is moved in the horizontal direction to bring solid 160 closer to the focal position. FIG. 14F then shows how tube 50 is rotated 154 to bring solid 160 closer to the focal position. However, after this rotational movement, solid 160 is now closer to the focal point and needs to be lowered. FIG. 14G shows how tube 50 is moved in vertical direction 152 to complete the process of bringing solid 160 into focus just below the inner surface of tube 50.

Using spectral signal intensity feedback from the Raman CCD, focal distance is "auto-focused" by computer controlling the XY position and the Z-height between the tube and the microscope objective. This auto-focus capability allows for the automated collection of Raman spectra once the tube is in place under the objective. Additionally, the NTSC video camera on the Raman allows for video capture and frame grabbing of the sample as it is being analyzed. This feature further allows for a spatial "history" to be created whereby the exact location of laser on the tube can be associated with a specific Raman spectrum. In order to implement the previously mentioned auto-focus capability, the tube holder has a computer controlled, motorized rotation axis. This controllable rotation allows the system, again under feedback control, to rotate the tube under the microscope objective in order to scan the entire inside surface of the tube.

When this feature is used, it is often not quite as important to pre-align the samples in the tube so that the sample is in the field of view as discussed above. Moreover, this feature allows for rotation during collection of a Raman spectrum. This is important to minimize so-called orientation effects that are sometimes observed in Raman spectra from anisotropic crystalline samples. Orientation effects exist when a sample has two or more unequivocal crystallographic "faces" that can be targeted by the laser source. Depending on the analyzed face, different spectra are generated, although the sample is physically unchanged. These different spectra might cause one to draw the conclusion that two or more different samples were present.

Once the sample in the tube is analyzed, the tube gripper removes the tube from the tube holder and returns it to the original location in the tube block followed by the XY stage indexing to the next tube to be analyzed.

5.2. Example 2

Data Collection and Binning

The effectiveness of binning was demonstrated using two test sets that included the Raman spectra of a polymorphic material and a material with two hydration states. First, the authenticity of the samples was validated. Next, Raman spectra for each sample under varying acquisition conditions were collected. The spectra were then filtered and binned using the previously described algorithms and method. Finally, the results were cross-checked by comparison of the known sample identification to the bin/cluster assignment. Each of these steps is outlined below.

Authentic polymorphic forms (polymorphs) and anhydrate/hydrate forms for a given material each exhibit a unique x-ray powder diffraction pattern and melting transition. Such criteria were deemed sufficient evidence to verify authenticity of each sample. Representatives of each of the forms of sample sets 1 and 2 were therefore characterized using x-ray diffraction (XRD) and differential scanning calorimetry (DSC), generating x-ray powder diffraction patterns and thermal transition data to determine sample uniqueness. Aliquots of samples from set 2 were further characterized using thermo-gravimetric analysis (TGA) to confirm the hydration state (i.e., water content) of the samples.

5.2.1. Materials and Experimental Methods

Two test sets were used to demonstrate the binning procedure for Raman spectra. Set 1 had two polymorphic forms of Flufenamic acid (2-[[3-(Trifluoromethyl)phenyl]amino]benzoic acid), and set 2 had the anhydrate and monohydrate of theophylline (3,7-Dihydro-1,3-dimethyl-1-H-purine-2,6-dione). Anhydrous theophylline was obtained from Fluka Biochemica (Lot & Filling Code 403967/113700). The monohydrate was prepared by suspending 4.0 g of anhydrous theophylline in 20 ml of methyl alcohol. While stirring, 20 ml of de-ionized water was added to the suspension and the as-diluted suspension was warmed to approximately 40° C. to promote conversion to the hydrated form. The resulting suspension was continuously stirred and allowed to cool to 25° C. under ambient conditions. An aliquot of the suspension was collected by filtration after 6 hours and allowed to air dry. The solid obtained was characterized as described below to verify its hydration state.

All x-ray powder diffraction patterns were obtained using the D/Max Rapid X-ray Diffractometer (Rigaku/MSC, The Woodlands, Tex., U.S.A.), which uses as its control software RINT Rapid Control Software, Rigaku Rapid/XRD, version 1.0.0 (©1999 Rigaku Co.), equipped with a copper source (Cu/K 1.5406), manual x-y stage and 0.3 mm collimator. Samples were loaded in to 0.3 mm quartz capillary tubes supplied by Charles Supper Company by tapping the open end of the capillary into a bed of the powdered sample. The loaded capillary was mounted in a holder that was placed into the x-y stage. Diffractograms were acquired under ambient conditions at a power setting of 46 kV at 40 mA in transmission mode, while oscillating about the omega-axis from 0–5 degrees at 1 degree/s and spinning about the phi-axis at 2 degrees/s. Exposure times were 30 minutes unless otherwise specified. The diffractograms obtained were integrated over 2-theta from 2–60 degrees and chi (1 segment) from 0–40 degrees at a step size of 0.02 degrees using the cyllnt utility in the RINT Rapid display software version 1.18 provided by Rigaku with the instrument. No normalization or omega, chi or phi offsets were used for the integration.

5.2.2. Results and Discussion

Figure 19A:
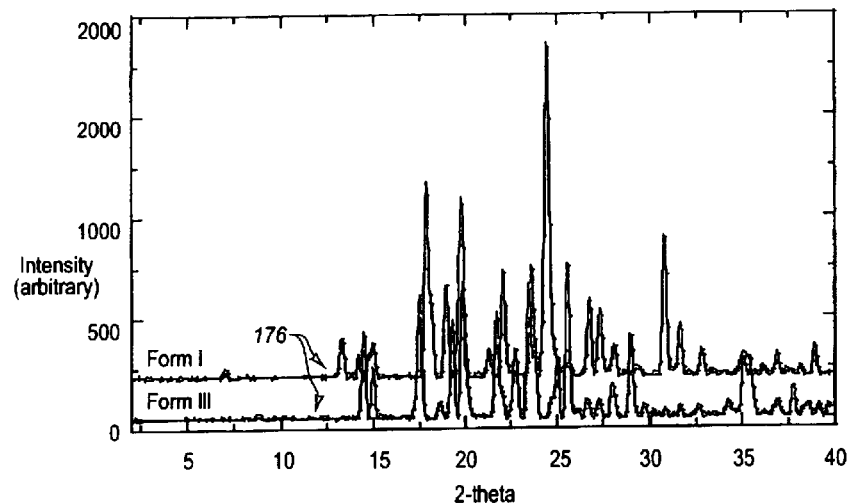
FIG. 19A is a comparative graph of X-ray powder diffraction patterns for Form I and Form III of flufenamic acid.
Figure 19B:
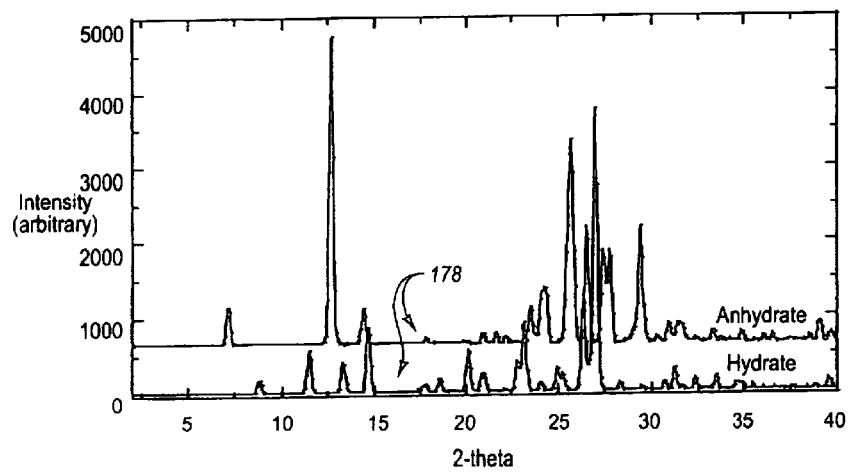
FIG. 19B is a comparative graph of X-ray powder diffraction patterns for anhydrous and monohydrate forms of theophylline.

The resultant X-ray powder patterns, plotted as intensity (arbitrary units) as a function of 2-theta (degrees), are shown in FIGS. 19A and 19B for the flufenamic acid 176 and theophylline 178 samples, respectively. Comparison of the x-ray powder patterns within each set clearly shows unique reflections (e.g., shifted peaks) in each pattern, indicating structural differences between the samples within each set and hence, validating the authenticity of the samples. Note, comparable x-ray powder patterns for the anhydrous and monohydrate forms of theophylline have been reported by Zhu et al. (*International Journal of Pharmaceutics*, 135: 151–160 (1996))).

Further confirmation of the authenticity of the test sets was provided by DSC thermal analysis. An aliquot of each sample was weighed into an aluminum sample pan obtained from TA Instruments (pan number 90078.609, lid number 900779.901). Pans containing flufenamic acid samples were crimped closed, whereas pans containing theophylline samples were fit pressed to avoid pressure build up due to potential water vaporization. Sample pans were loaded into the apparatus and thermograms were obtained by individually heating the samples at a rate of 10° C./min from 20° C. to 350° C. using an empty crimped aluminum pan as a reference.

Figure 20A:
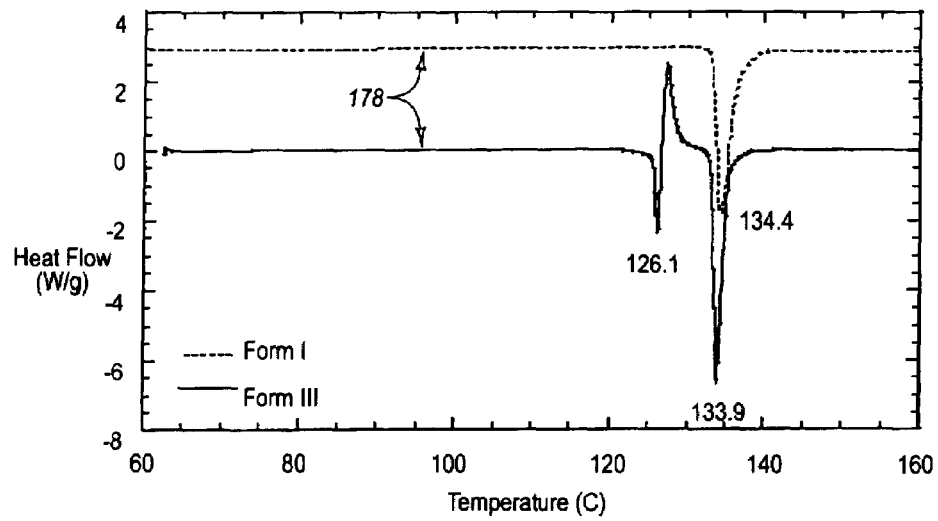
FIG. 20A is a comparative graph of DSC thermograms for Form I and Form III of flufenamic acid where heat flow (W/g) is plotted as a function of temperature (° C.).
Figure 20B:
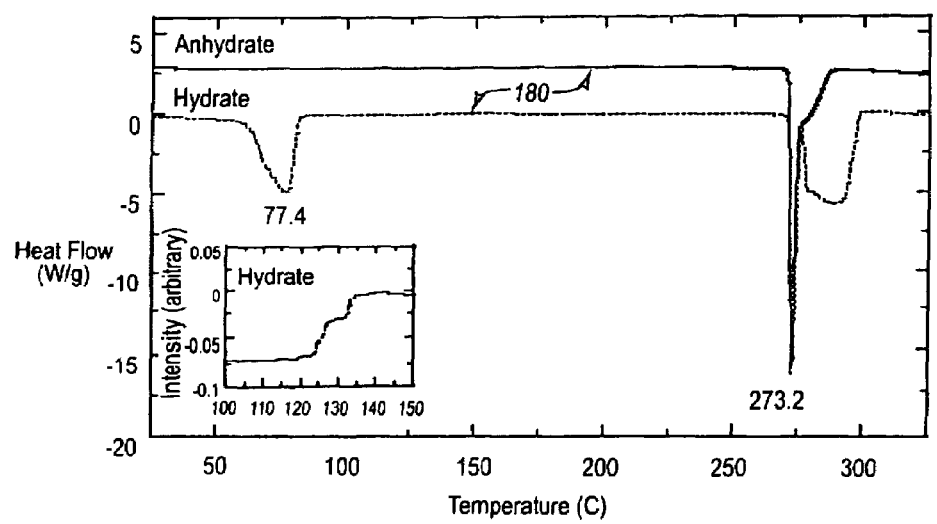
FIG. 20B is a comparative graph of DSC thermograms for anhydrous and monohydrate forms of theophylline where heat flow (W/g) is plotted as a function of temperature (° C.).

The DSC thermograms for the flufenamic acid 178 and theophylline 180 sample sets are shown in FIGS. 20A and 20B, respectively, where heat flow (W/g) is plotted as a function of temperature (° C.). The melt transition (peak temperature) of flufenamic acid samples was observed at 134.4° C. for Form I showing it to be pure Form I, whereas Form III exhibited a melt at 126.1° C., followed by recrystallization and another melt at 133.9° C. indicating the conversion of Form III (melting point=126.1° C.) to Form I upon heating. The DSC thermogram for anhydrous theophylline shows a single sharp endotherm at 273.1° C. corresponding to the melting transition of the sample. The DSC curve for the hydrated sample exhibits two endotherms, the first occurring at a peak temperature of approximately 77.4° C. where dehydration of the sample is expected. This is followed by an endotherm at 273.1° C., where the anhydrous form melts.

Thermo-gravimetric analysis (TGA) was performed on samples from set 2 to verify water content. An aliquot of each sample was transferred into a platinum sample holder obtained from TA Instruments (#952019.9061) and loaded in to the apparatus. Thermograms were obtained by individually heating the samples at 10° C./min from 25° C. to 300° C. under flowing dry nitrogen (balance purge 40 ml/min; sample purge 60 ml/min).

Figure 21:
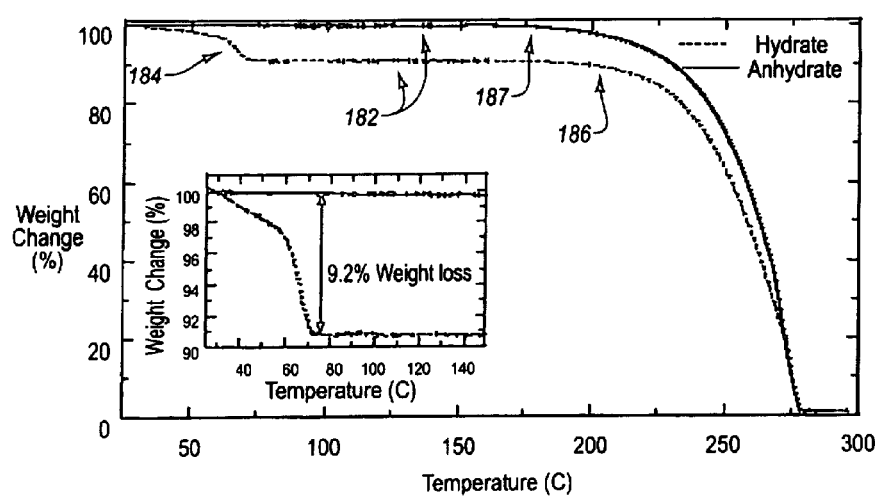
FIG. 21 is a graph showing thermograms obtained for the anhydrous and hydrous forms of theophylline. An inset graph shows an enlargement of the same thermograms between 35° C. and 150° C.

The thermograms obtained for the anhydrous and hydrous forms of theophylline are shown in FIG. 21, where the weight change (%) is plotted 182 as a function of temperature (° C.). As illustrated in FIG. 21, the hydrated sample undergoes a two-step weight loss. The first weight loss 184 of 9.2% begins at approximately 25° C. and continues until approximately 70° C. This weight change is associated with loss of loosely bound water from the hydrate structure and corresponds to a water mole fraction of 0.50, indicating the sample is a monohydrate of theophylline. For comparison, the theoretical water content for the monohydrate of theophylline is 9.09%. The small deviation in the measured sample is attributed to surface absorbed water, typically ranging from 0.0–0.3%. At approximately 172° C., the second weight loss 186 indicative of decomposition of the compound is observed. Note, the anhydrous theophylline sample exhibits only one weight loss 187 corresponding to decomposition beginning at approximately 172° C.

5.2.3. Reference Raman Spectra

For reference, Raman spectra were collected for each of the samples in sets 1 and 2. An aliquot of the sample was transferred to a glass slide that was positioned in the sample chamber. The measurement was made using the Almega™ Dispersive Raman system fitted with a 785 nm laser source. The sample was manually brought into focus using the microscope portion of the apparatus with a 10× power objective, thus directing the laser onto the surface of the powdered sample atop a glass slide. The spectra were acquired using the parameters outlined in the following table:

TABLE 2

Raman spectral acquisition parameters

| Parameter | Setting Used |
|---|---|
| Exposure time (s) | 2.0 |
| Number of exposures | 10 |
| Laser source wavelength (nm) | 785 |
| Laser power (%) | 100 |
| Aperture shape | pin hole |
| Aperture size (μm) | 100 |
| Spectral range | 105–4252 |
| Grating position | single |
| Temperature at acquisition (° C.) | 24.0 |

Figure 22A:
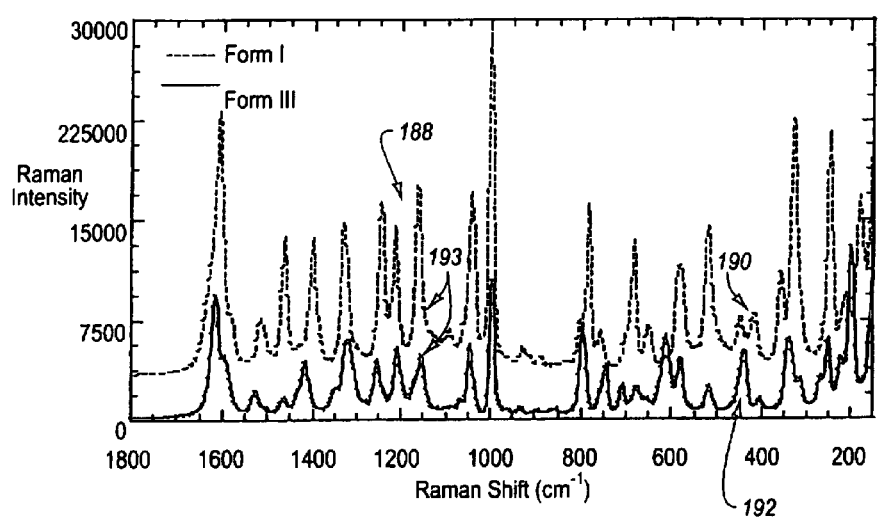
FIG. 22A is a graph showing Raman intensity (arbitrary units) plotted as a function of Raman shift ($cm^{-1}$) for Form I and Form III of flufenamic acid.
Figure 22B:
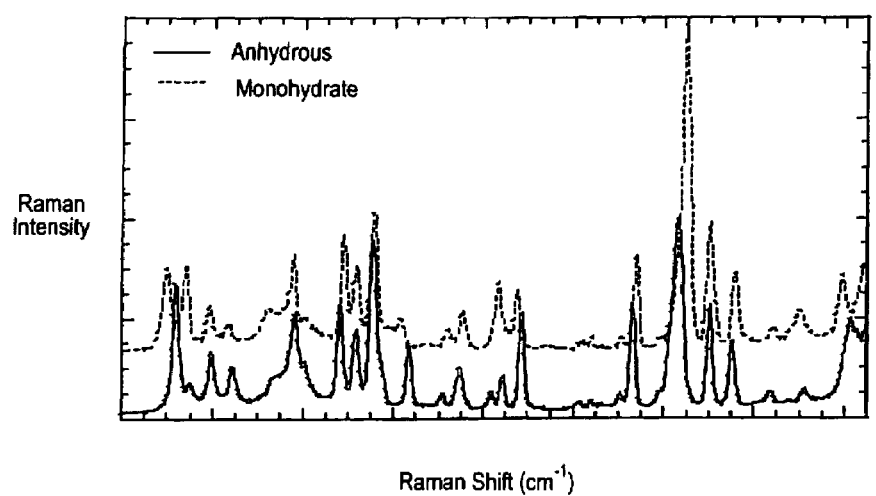
FIG. 22B is a graph showing the Raman intensity (arbitrary units) plotted as a function of Raman shift ($cm^{-1}$) for anhydrous and monohydrate forms of theophylline.

The unfiltered Raman spectra generated for each sample are shown in FIGS. 22A and 22B, where the Raman intensity (arbitrary units) is plotted as a function of Raman shift ($cm^{-1}$). Note that the appearance or disappearance of peaks and/or shifts in peak position between the samples within a set was observed. For example, the spectra shown in FIG. 22A for flufenamic acid polymorphs of sample set 1 show a doublet 190 centered around 450 $cm^{-1}$ for form I and a singlet 192 for form III at that position, as well as significant shifting of the three peaks 193 in the 1150–1250 $cm^{-1}$ range. Such peak appearance/disappearance and/or shifts in peak position indicate a unique crystal packing configuration, thus differentiating the forms and showing that the Raman spectra can be used as a unique signature for a given form.

5.2.4. Filtering of Raman Spectra

Evaluation of the filtering and binning algorithms was carried out by acquiring at least 20 spectra for each of the samples from sets 1 and 2, filtering the spectra to remove background signals, and binning the spectra. To collect the Raman spectra, an aliquot of each sample was transferred onto a glass slide or into a glass vial. Measurements were made by directing the laser onto the surface of the powdered sample atop the glass slide (theophylline) or through the glass vial (flufenamic acid). The acquisition parameters used are provided in TABLE 2 with the exception that half of the spectra collected for each polymorph of set 1 (flufenamic acid) were collected using the 50× microscope objective rather than the 10× objective. The sampling location was varied either by moving the glass slide or rotating the glass vial.

All spectra were filtered to remove background signals, including glass contributions and sample fluorescence. This is particularly important as large background signal or fluorescence limit the ability to accurately pick and assign peak positions in the subsequent steps of the binning process. Such background contributions to the Raman spectra are shown in FIGS. 16A and 16B for representative glass and fluorescent samples, respectively. Spectra from all samples of test sets 1 and 2 were filtered using a matched filter of feature size 25. An example of the original and filtered spectra for a fluorescent sample is shown in FIG. 16C.

5.2.5. Binning of Raman Spectra

Filtered spectra were binned using the algorithm described above under the peak picking and binning parameters given in TABLE 3 and screen shots showing the output from the binning software captured during the binning procedure are provided in FIGS. 17A and 17B for the flufenamic acid and theophylline sample sets, respectively.

TABLE 3

Peak picking and binning parameters used.

| Parameter | Setting Used for Binning |
|---|---|
| QC Parameters | |
| Peak Height Threshold | 1000 |
| Region for noise test ($cm^{-1}$) | 0–10000 |
| RMS noise threshold | 10000 |
| Automatically eliminate failed spectra | yes |
| Region of Interest | |
| Include ($cm^{-1}$) | 120–1800 |
| Peak Pick Parameters | |
| Peak Pick Sensitivity | 99 |
| Peak Pick Threshold | 100 |
| Peak Comparison Parameters | |
| Peak Window ($cm^{-1}$) | 3 |
| Analysis Parameters | |
| Number of clusters | 2 |

Figure 23A:
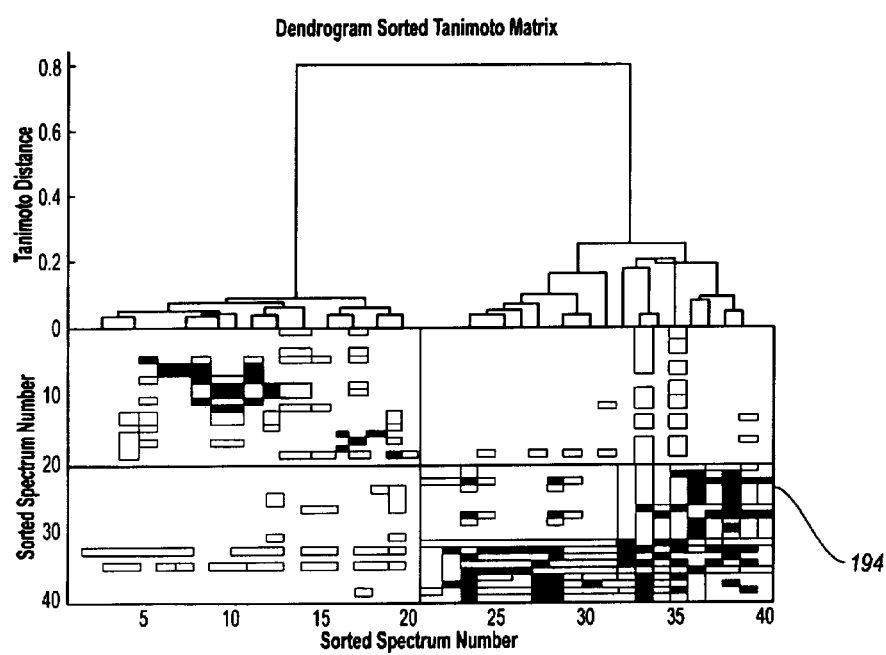
FIG. 23A is the output after clustering illustrating sorted cluster diagrams for the flufenamic acid sample set.
Figure 23B:
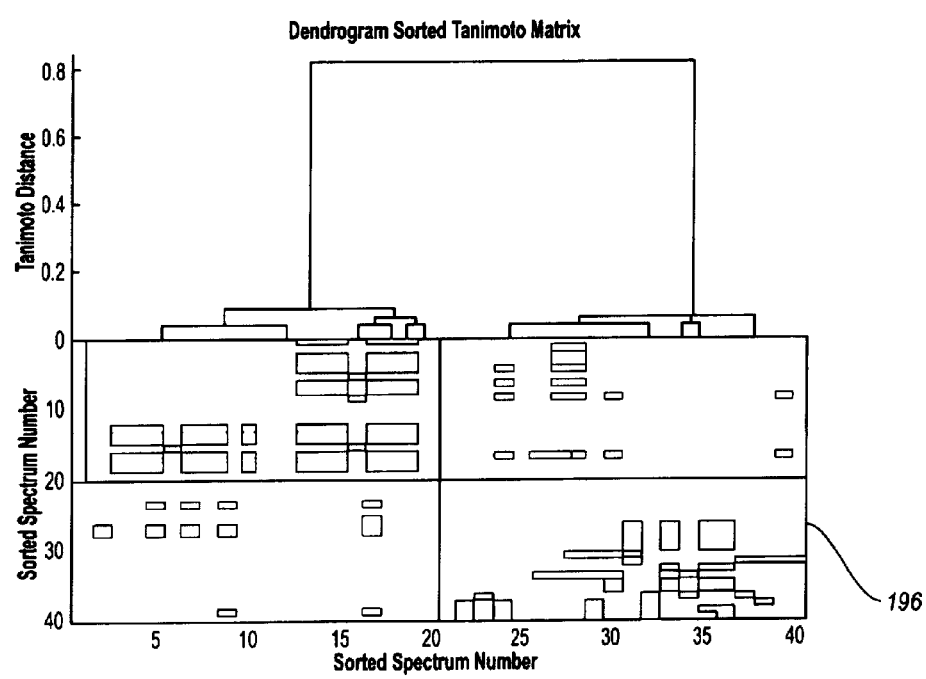
FIG. 23B is the output after clustering illustrating sorted cluster diagrams for the theophylline sample set.
Figure 24A:
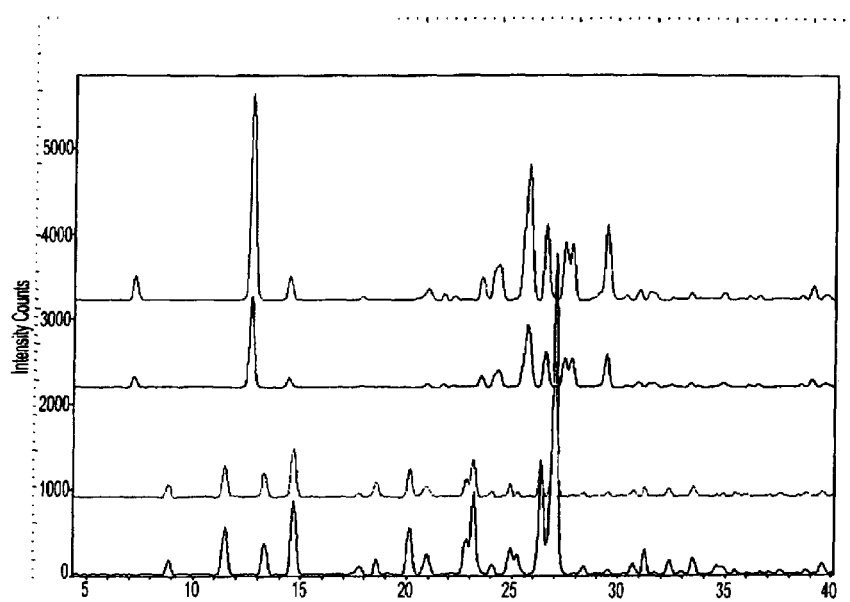
FIG. 24A illustrates X-ray crystal diffraction spectra corresponding to the anhydrate and the hydrate forms of Theophylline.
Figure 24B:
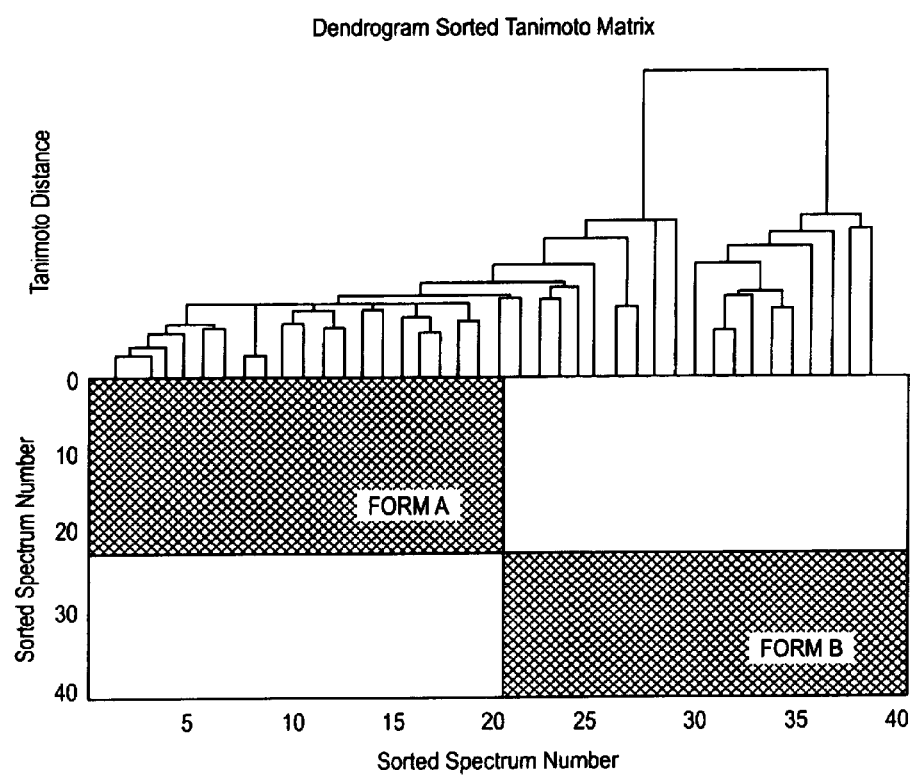
FIG. 24B illustrates the binning of Raman Spectra corresponding to Hydrate distinctly from Anhydrate form of Theophylline.

The sorted cluster diagrams 194 and 196 showing the output for each sample set are illustrated in FIGS. 23A and 23B and the corresponding cluster assignments for each spectral file are provided in TABLES 4 and 5, respectively.

TABLE 4

Cluster assignments for each spectral file for flufenamic acid sample set.

| File Name | Cluster Number | Original Number | Sorted Number |
|---|---|---|---|
| Filtered flufenamic I 10x | 1 | 1 | 1 |
| Filtered flufenamic I 10x 10.SPA | 1 | 2 | 5 |
| Filtered flufenamic I 10x 2.SPA | 1 | 3 | 6 |
| Filtered flufenamic I 10x 3.SPA | 1 | 4 | 9 |
| Filtered flufenamic I 10x 4.SPA | 1 | 5 | 4 |
| Filtered flufenamic I 10x 5.SPA | 1 | 6 | 7 |
| Filtered flufenamic I 10x 6.SPA | 1 | 7 | 8 |
| Filtered flufenamic I 10x 7.SPA | 1 | 8 | 15 |
| Filtered flufenamic I 10x 8.SPA | 1 | 9 | 2 |
| Filtered flufenamic I 10x 9.SPA | 1 | 10 | 3 |
| Filtered flufenamic I 50x 1.SPA | 1 | 11 | 16 |
| Filtered flufenamic I 50x 10.SPA | 1 | 12 | 11 |
| Filtered flufenamic I 50x 2.SPA | 1 | 13 | 17 |
| Filtered flufenamic I 50x 3.SPA | 1 | 14 | 18 |
| Filtered flufenamic I 50x 4.SPA | 1 | 15 | 20 |
| Filtered flufenamic I 50x 5.SPA | 1 | 16 | 12 |
| Filtered flufenamic I 50x 6.SPA | 1 | 17 | 19 |
| Filtered flufenamic I 50x 7.SPA | 1 | 18 | 13 |
| Filtered flufenamic I 50x 8.SPA | 1 | 19 | 14 |
| Filtered flufenamic I 50x 9.SPA | 1 | 20 | 10 |
| Filtered flufenamic III 10x 1.SPA | 2 | 21 | 21 |
| Filtered flufenamic III 10x 10.SPA | 2 | 22 | 28 |
| Filtered flufenamic III 10x 11.SPA | 2 | 23 | 29 |
| Filtered flufenamic III 10x 2.SPA | 2 | 24 | 26 |
| Filtered flufenamic III 10x 3.SPA | 2 | 25 | 22 |
| Filtered flufenamic III 10x 4.SPA | 2 | 26 | 23 |
| Filtered flufenamic III 10x 5.SPA | 2 | 27 | 31 |
| Filtered flufenamic III 10x 6.SPA | 2 | 28 | 30 |
| Filtered flufenamic III 10x 7.SPA | 2 | 29 | 27 |
| Filtered flufenamic III 10x 8.SPA | 2 | 30 | 24 |
| Filtered flufenamic III 10x 9.SPA | 2 | 31 | 25 |
| Filtered flufenamic III 50x 1.SPA | 2 | 32 | 33 |
| Filtered flufenamic III 50x 10.SPA | 2 | 33 | 34 |
| Filtered flufenamic III 50x 2.SPA | 2 | 34 | 36 |
| Filtered flufenamic III 50x 3.SPA | 2 | 35 | 35 |
| Filtered flufenamic III 50x 4.SPA | 2 | 36 | 32 |
| Filtered flufenamic III 50x 5.SPA | 2 | 37 | 37 |
| Filtered flufenamic III 50x 7.SPA | 2 | 38 | 39 |

TABLE 4-continued

Cluster assignments for each spectral file for flufenamic acid sample set.

| File Name | Cluster Number | Original Number | Sorted Number |
|---|---|---|---|
| Filtered flufenamic III 50x 8'.SPA | 2 | 39 | 38 |
| Filtered flufenamic III 50x 9.SPA | 2 | 40 | 40 |

TABLE 5

Cluster assignments for each spectral file for theophylline sample set.

| File Name | Cluster Number | Original Number | Sorted Number |
|---|---|---|---|
| Filtered Theophylline Hydrate1.SPA | 1 | 1 | 1 |
| Filtered Theophylline Hydrate10.SPA | 1 | 2 | 14 |
| Filtered Theophylline Hydrate11.SPA | 1 | 3 | 7 |
| Filtered Theophylline Hydrate12.SPA | 1 | 4 | 8 |
| Filtered Theophylline Hydrate13.SPA | 1 | 5 | 9 |
| Filtered Theophylline Hydrate14.SPA | 1 | 6 | 15 |
| Filtered Theophylline Hydrate15.SPA | 1 | 7 | 10 |
| Filtered Theophylline Hydrate16.SPA | 1 | 8 | 11 |
| Filtered Theophylline Hydrate17.SPA | 1 | 9 | 16 |
| Filtered Theophylline Hydrate18.SPA | 1 | 10 | 12 |
| Filtered Theophylline Hydrate19.SPA | 1 | 11 | 17 |
| Filtered Theophylline Hydrate2.SPA | 1 | 12 | 19 |
| Filtered Theophylline Hydrate20.SPA | 1 | 13 | 2 |
| Filtered Theophylline Hydrate3.SPA | 1 | 14 | 3 |
| Filtered Theophylline Hydrate4.SPA | 1 | 15 | 4 |
| Filtered Theophylline Hydrate5.SPA | 1 | 16 | 18 |
| Filtered Theophylline Hydrate6.SPA | 1 | 17 | 13 |
| Filtered Theophylline Hydrate7.SPA | 1 | 18 | 5 |
| Filtered Theophylline Hydrate8.SPA | 1 | 19 | 6 |
| Filtered Theophylline Hydrate9.SPA | 1 | 20 | 20 |
| Filtered Theophylline1.SPA | 2 | 21 | 21 |
| Filtered Theophylline10.SPA | 2 | 22 | 27 |
| Filtered Theophylline11.SPA | 2 | 23 | 33 |
| Filtered Theophylline12.SPA | 2 | 24 | 28 |
| Filtered Theophylline13.SPA | 2 | 25 | 34 |
| Filtered Theophylline14.SPA | 2 | 26 | 29 |
| Filtered Theophylline15.SPA | 2 | 27 | 30 |
| Filtered Theophylline16.SPA | 2 | 28 | 22 |
| Filtered Theophylline17.SPA | 2 | 29 | 31 |
| Filtered Theophylline18.SPA | 2 | 30 | 23 |
| Filtered Theophylline19.SPA | 2 | 31 | 40 |
| Filtered Theophylline2.SPA | 2 | 32 | 36 |
| Filtered Theophylline20.SPA | 2 | 33 | 24 |
| Filtered Theophylline3.SPA | 2 | 34 | 38 |
| Filtered Theophylline4.SPA | 2 | 35 | 25 |
| Filtered Theophylline5.SPA | 2 | 36 | 26 |
| Filtered Theophylline6.SPA | 2 | 37 | 39 |
| Filtered Theophylline7.SPA | 2 | 38 | 37 |
| Filtered Theophylline8.SPA | 2 | 39 | 32 |
| Filtered Theophylline9.SPA | 2 | 40 | 35 |

In each sample set, two distinct clusters are observed represented by sorted spectra numbers 1–20 and 21–40 that correspond to the file names and sample identifications provided in TABLES 4 and 5. In comparing the cluster assignments to the sample identification (by file number), 100% binning accuracy is observed for each test set. For example, all form I samples are binned in cluster 1 and all form III samples are binned together in cluster 2 for flufenamic acid test set 1.

While the invention has been described in connection with what is presently considered to be the practical and preferred embodiments, the invention is not limited to the disclosed embodiments. In particular, it will be clear to those skilled in the art that this invention may be embodied in other specific forms, structures, and arrangements, and with other elements, and components, without departing from the spirit or essential characteristics thereof. One skilled in the art will appreciate that the invention may be used with many modifications of structure, arrangement, and components and otherwise, used in the practice of the invention, which are particularly adapted to specific environments and operative requirements without departing from the principles of this invention. The presently disclosed embodiments are therefore to be considered in all respects as illustrative and not restrictive, the scope of the invention being indicated by the appended claims.

The invention claimed is:

1. A method of screening an array of samples comprising analyzing an array of samples with a system for detecting similarities among a plurality of samples, which comprises
   a) a device for obtaining a spectrum for each sample; and
   b) a computer configured to analyze each of the spectra and to generate a plurality of bins, wherein each bin corresponds to samples sharing at least one spectral feature.

2. The method of claim 1 wherein the spectral feature is unique to a particular form of a compound-of-interest.

3. The method of claim 1, wherein the device is an infrared spectrometer, near infrared spectrometer, NMR spectrometer, X-ray diffractometer, neutron diffractometer, light microscope, electron microscope, second harmonic generator, circular dichroism spectrometer, linear dichroism spectrometer, differential scanning calorimeter, thermal gravimetric analyzer, or melting point analyzer.

4. The system of claim 1 wherein the device is a Raman spectrometer.

5. The system of claim 1 wherein the computer is further configured to generate a binary spectral representation for a spectrum that reflects the presence or absence of a spectral feature.

6. The system of claim 1 wherein the computer is configured to mutually compare a plurality of spectra and generate a hierarchical clustering dendrogram.

7. The system of claim 1 wherein the computer is configured to cluster the plurality of spectra.

8. The system of claim 7 wherein the computer is configured to cluster the plurality of spectra in accordance with iterative k-means clustering.

9. The system of claim 1 wherein the computer is configured to cluster the plurality of spectra such that if a majority of spectra obtained from a single sample are assigned to a particular bin, then all spectra from that sample are assigned to that bin.

10. The system of claim 1 wherein the computer is configured to assign newly obtained spectra to at least one of the plurality of bins.

11. The system of claim 1 wherein the computer is configured to modify, in response to an analysis of newly obtained spectra, at least one of the plurality of bins.

12. The system of claim 1 wherein the computer is configured to add, in response to an analysis of newly obtained spectra, at least one bin to the plurality of bins.

13. The system of claim 1 wherein the computer is configured to generate a similarity matrix representing the similarity between at least two of the plurality of samples.

14. The system of claim 13 wherein the computer is further configured to sort the samples such that they are arranged to reflect their similarity.

15. The system of claim 13 wherein the computer is further configured to sort the similarity matrix such that a diagonal in the matrix represents samples exhibiting the greatest similarity.

16. The method of claim 1 wherein the samples comprise a solid form compound of interest.

17. The method of claim 2 wherein the particular form is a solid form.

18. The method of claim 16 wherein the solid form is a crystalline form.

19. The method of claim 16 wherein the solid form is an amorphous form.

20. The method of claim 16 the particular form is a hydrate.

21. The method of claim 17 wherein the solid form is a crystalline form.

22. The method of claim 17 wherein the solid form is an amorphous form.

23. The method of claim 17 the particular form is a hydrate.

* * * * *

UNITED STATES PATENT AND TRADEMARK OFFICE
CERTIFICATE OF CORRECTION

PATENT NO. : 7,061,605 B2
APPLICATION NO. : 11/051517
DATED : June 13, 2006
INVENTOR(S) : Lemmo et al.

It is certified that error appears in the above-identified patent and that said Letters Patent is hereby corrected as shown below:

<u>Title Page</u>
Page 1, Item 63, Related U.S. Application Data, Column 2, Paragraph 2, Line 6, change "60/235,629" to --60/253,629--

<u>Column 6</u>
Line 13, change "18" to --17--

<u>Column 13</u>
Line 57, change "18" to --17--

<u>Column 15</u>
Line 3, remove "in"

<u>Column 19</u>
Line 66, change "128" to --125--

<u>Column 20</u>
Line 21, change "function" to --functions--

<u>Column 21</u>
Line 35, remove "are"

<u>Column 22</u>
Lines 61-62, change "Mat-sousek" to --Mat-ousek--
Line 63, change "Picosecond" to --picosecond--
Line 64, change "Gate" to --gate--

<u>Column 24</u>
Line 44, after "can" insert --be--

<u>Column 25</u>
Line 8, change "is" to --are--

<u>Column 27</u>
Lines 53-54, change "A spectral" to --Spectral--

UNITED STATES PATENT AND TRADEMARK OFFICE
CERTIFICATE OF CORRECTION

PATENT NO. : 7,061,605 B2
APPLICATION NO. : 11/051517
DATED : June 13, 2006
INVENTOR(S) : Lemmo et al.

It is certified that error appears in the above-identified patent and that said Letters Patent is hereby corrected as shown below:

Column 30
Line 13, change "2405" to --1805--

Column 33
Line 24, change "113700" to --1 13700--

Column 35
Line 59, change "25" to --25--

Column 37
Table 4, first compound, change "8'.SPA" to --8.SPA--

Column 40
Line 5, after "17" insert --wherein--

Signed and Sealed this

Sixth Day of March, 2007

JON W. DUDAS
*Director of the United States Patent and Trademark Office*